US012673921B2

(12) United States Patent
Deng et al.

(10) Patent No.: US 12,673,921 B2
(45) **Date of Patent: *Jul. 7, 2026**

(54) SUBSTITUTED FLUORINE-CONTAINING IMIDAZOLE SALT COMPOUND, PREPARATION METHOD THEREFOR, PHARMACEUTICAL COMPOSITION THEREOF AND USE THEREOF

(71) Applicant: XIAMEN VIVOHEALTHS TECHNOLOGY CO., LTD., Xiamen (CN)

(72) Inventors: Xianming Deng, Xianmen (CN); Shengcai Lin, Xianmen (CN); Chensong Zhang, Xianmen (CN)

(73) Assignee: XIAMEN VIVOHEALTHS TECHNOLOGY CO., LTD., Xiamen (CN)

( * ) Notice: Subject to any disclaimer, the term of this patent is extended or adjusted under 35 U.S.C. 154(b) by 1092 days.

This patent is subject to a terminal disclaimer.

(21) Appl. No.: 17/610,417

(22) PCT Filed: May 8, 2020

(86) PCT No.: PCT/CN2020/089128

§ 371 (c)(1),
(2) Date: Nov. 10, 2021

(87) PCT Pub. No.: WO2020/228596

PCT Pub. Date: Nov. 19, 2020

(65) Prior Publication Data

US 2022/0242828 A1 Aug. 4, 2022

(30) Foreign Application Priority Data

May 10, 2019 (CN) ........................ 201910387619.5

(51) Int. Cl.
*C07D 233/56* (2006.01)
*A61P 3/06* (2006.01)
*A61P 3/10* (2006.01)
*C07D 233/60* (2006.01)
*C07D 233/68* (2006.01)

(52) U.S. Cl.
CPC .............. *C07D 233/68* (2013.01); *A61P 3/06* (2018.01); *A61P 3/10* (2018.01); *C07D 233/60* (2013.01)

(58) Field of Classification Search
CPC .. C07D 233/54; C07D 233/56; C07D 233/61; C07D 233/60; A61K 31/4174
See application file for complete search history.

(56) References Cited

U.S. PATENT DOCUMENTS 8,236,887 B2 8/2012 Komatsu et al.
11,584,722 B2 * 2/2023 Deng ........................ A61P 1/16

FOREIGN PATENT DOCUMENTS

| | | | | |
|---|---|---|---|---|
| CN | 101983057 A | | 3/2011 | |
| CN | 103547154 A | | 1/2014 | |
| CN | 108689939 A | | 10/2018 | |
| WO | 2009109798 A2 | | 9/2009 | |
| WO | WO-2009133923 A1 | * | 11/2009 | ........... C07D 233/06 |
| WO | 2009146146 A2 | | 12/2009 | |

OTHER PUBLICATIONS

Bohm et al. ChemBioChem 2004, 5, 637-643.*
Jeffries et al. J. Med. Chem. 2018, 61, 10602-10618.*
Indian Hearing Notice regarding POD/Application No. /202147057549, issued Jun. 12, 2023, 3 pages.
Uxe, Hong and Shreeve, Jean'ne M., Eur. J. Inorg. Chem, 2005, pp. 2573-2580.
Translation of International Search Report mailed Aug. 10, 2020 in corresponding International Patent Application No. PCT/CN2020/089128.
Extended European Search Report issued May 5, 2023 in corresponding European application No. 20806506.0; 6 pages.
Notice of Non-Final Rejection issued Feb. 8, 2024 in South Korean patent application No. 10-2021-7039481, filed Dec. 1, 2021 (with Eng. translation) (19 pages).
Bastin, R. et al. "Salt Selection and Optimisation Procedures for Pharmaceutical New Chemical Entities" Organic Process Research & Development; 2000, v. 4, pp. 427-435.

(Continued)

*Primary Examiner* — Irina Neagu
(74) *Attorney, Agent, or Firm* — Bayramoglu Law Offices LLC

(57) ABSTRACT

Disclosed in the invention are a type of compounds having activity of activating 5'-adenosine monophosphate-activated protein kinase (AMPK), a method for the preparation thereof, a pharmaceutical composition comprising the same, and use of these compounds in the manufacture of a medicament for reducing fatty acid synthesis, for inhibiting triglyceride and cholesterol synthesis, for preventing and/or treating obesity and type II diabetes, for preventing and/or treating tumor, for preventing and/or treating Parkinson's disease, for preventing and/or treating Alzheimer's disease or for prolonging the lifespan of mammals:

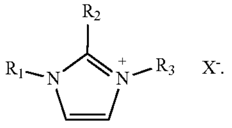

9 Claims, 5 Drawing Sheets

(56) References Cited

OTHER PUBLICATIONS

Reddy et al., "Indium trifluoride: A highly efficient catalyst for the synthesis of fluorine-containing 2, 4, 5-trisubstituted imidazoles under solvent-free conditions", 2012, Journal of Fluorine Chemistry 142, pp. 45-51.
First Examination Report mailed Feb. 14, 2022 in corresponding Indian Patent Application No. 202147057549, 6 pages.
Supplementary European Search Report regarding European application EP 20806506, issued Apr. 21, 2023, 6 pages.
Christmann, U. et al. "Discovery of WLB-89462, a New Drug-like and Highly Selective σ2 Receptor Ligand with Neuroprotective Properties" J. Med. Chem, 2023, 66(17), 12499-12519.
Wehn, P.M. et al. "Design and Activity of Specific Hypoxia-Inducible Factor-2α (HIF-2α) Inhibitors for the Treatment of Clear Cell Renal Cell Carcinoma: Discovery of Clinical Candidate (S)-3-((2,2-Difluoro-1-hydroxy-7-(methylsulfonyl)-2,3-dihydro-1H-inden-4-yl)oxy)-5-fluorobenzonitrile (PT2385)", J. Med. Chem, 2018, 61(21), 9691-9721.
Ching, K. et al. "Structural Optimizations of Thieno[3,2-b]pyrrole Derivatives for the Development of Metabolically Stable Inhibitors of Chikungunya Virus", J. Med. Chem., 2017, 60, 3165-3186.
Benjamin Jeffries, et al., Reducing the Lipophilicity of Perfluoroalkyl Groups by CF2—F/CF2-Me or CF3/CH3 Exchange, J. Med. Chem., 2018, pp. 10602-10618, vol. 61.
Neal O. Brace, Syntheses with perfluoroalkyl radicals from perfluoroalkyl iodides. A rapid survey of synthetic possibilities with emphasis on practical applications. Part one: alkenes, alkynes and allylic compounds, Journal of Fluorine Chemistry, 1999, pp. 1-25, vol. 93.

* cited by examiner

Gly:$C_2H_5NO$
Notes: when calculating MW, it is presumed that the produced metabolite is also hydrochloride

SUBSTITUTED FLUORINE-CONTAINING IMIDAZOLE SALT COMPOUND, PREPARATION METHOD THEREFOR, PHARMACEUTICAL COMPOSITION THEREOF AND USE THEREOF

CROSS REFERENCE TO RELATED APPLICATIONS

The present application is the U.S. National Phase under 35 U.S.C. § 371 of International Application No. PCT/CN2020/089128, filed May 8, 2020, which claims the priority of the Chinese patent application filed with the Chinese Patent Office on May 10, 2019, with the application No. 201910387619.5 and the invention title of "Substituted Fluorine-Containing Imidazole Salt Compound, Preparation Method Therefor, Pharmaceutical Composition Thereof And Use Thereof", the entire contents of each of which are herein incorporated in the present application by reference.

TECHNICAL FIELD

The invention relates to the field of medicinal chemistry, and in particular to a type of compounds having activity of activating 5'-adenosine monophosphate-activated protein kinase (AMPK), a method for the preparation thereof, a pharmaceutical composition comprising the same, and use of these compounds in the manufacture of a medicament for reducing fatty acid synthesis, for inhibiting triglyceride and cholesterol synthesis, for preventing and/or treating obesity and type II diabetes, for preventing and/or treating tumor, for preventing and/or treating Parkinson's disease, for preventing and/or treating Alzheimer's disease or for prolonging the lifespan of mammals.

BACKGROUND ART

5'-adenosine monophosphate-activated protein kinase (AMPK) is the most important molecule for sensing energy levels and regulating metabolic homeostasis in organisms and cells. AMPK is a heterotrimer composed of three subunits, α, β and γ. Under physiological conditions, when cells are in an energy deficient state, AMPK is activated through phosphorylation by its upstream kinase, to trigger a series of downstream reactions, including promotion of hydrolysis of triglycerides in adipocytes, promotion of hepatic uptake and oxidation of fatty acids in the blood, inhibition of production of fatty acid and cholesterol and triglyceride formation, promotion of lipid oxidation and glucose uptake and breakdown in muscle, inhibition of insulin secretion and glycogen synthesis in islet β cells, inhibition of protein synthesis and promotion of autophagy and ketogenesis, etc. (Hardie D G, Ross F A, Hawley S A. *Nat Rev Mol Cell Biol.* 2012 13 (4): 251-62). The result of these actions is to increase the energy-producing metabolism in vivo and reduce the energy-consuming metabolism in vivo, thereby achieving the effect of maintaining energy homeostasis and ensuring normal vital activities of cells. Thus, AMPK activation can have many healthy effects. For example, in a variety of tumor tissues, e.g., melanoma, breast cancer, colon cancer and lung cancer tissues, AMPK expression or activity is strongly inhibited, which further breaks the original balance of anabolism and catabolismin these tissues, exacerbating tumor progression (Shackelford D B, Shaw R J. *Nat Rev Cancer.* 2009 9 (8): 563-75). At the cellular level, there have been numerous studies indicating that AMPK activation can inhibit the anabolism of tumor cells, thereby preventing their proliferation, for example by inhibiting mTORC1 complex (Inoki K, Kim J, Guan K L. *Annu Rev Pharmacol Toxicol.* 2012 52:381-400), and can also inhibit the growth of tumor cells by promoting the viability of p53 leading to growth retardation and apoptosis of tumor cells (Jones R G et al., *Mol Cell.* 2005 18 (3): 283-93). Therefore, AMPK activators play an important role in the prevention and treatment of tumors.

Apart from tumors, AMPK is also closely related to diabetes. It has been found that AMPK viability is significantly inhibited in peripheral tissues of obese mice and type II diabetic patients (Viollet B. et al., *Crit Rev Biochem Mol Biol.* 2010 45 (4): 276-95). The activation of AMPK can promote the transfer of glucose transporter GLUT4 in muscle to cell membrane, and increase the absorption and catabolism of glucose in blood by muscle, thereby lowering blood sugar (Huang S, Czech M P. *Cell Metab.* 2007 5 (4): 237-52). In the liver, AMPK can also promote the enucleation of CRTC2 by phosphorylation, or promote the enucleation of FOXO1 by phosphorylation of deacetylase HDAC4/5/7, both of which result in inhibition of hepatic gluconeogenesis pathways and reduction of blood sugar (Altarejos J Y, Montminy M. *Nat Rev Mol Cell Biol.* 2011 12 (3): 141-51). Meanwhile, the activation of AMPK can also promote fat hydrolysis and fatty acid oxidation of obese mice, thereby achieving the effects of reducing the fat content in the liver, treating fatty liver, or reducing the volume of fat tissues and losing weight (Garcia D et al., *Cell Rep.* 2019 26 (1): 192-208; Pollard A et al., *Nature Metab.* 2019 1:340-349). Therefore, AMPK activators play an important role in the manufacture of a medicament for reducing fatty acid synthesis, for inhibiting triglyceride and cholesterol synthesis, for preventing and/or treating obesity and type II diabetes.

Meanwhile, since AMPK has multifunctional effects on carbohydrate, fat and cholesterol metabolism and biosynthesis, which are closely related to Parkinson's disease and Alzheimer's disease (Nat. Rev. Mol. Cell Biol. 2014, 15, 634-646), and prolongation of lifespan of organisms (Curr. Biol. 2007, 17, 1646-1656, Cell Metab. 2013, 17, 101-112, Cell Metab. 2014 20, 10-25, and Nat. Commu. 2013, 4, 2192), etc., AMPK activators play an important role in the manufacture of a medicament for preventing and/or treating Parkinson's disease, for preventing and/or treating Alzheimer's disease or for prolonging the lifespan of mammals.

However, despite such important associations of AMPK with metabolic regulation and even human health, few AMPK activators are available for clinical use, and currently only metformin is clinically used as a first-line drug for type II diabetes. The target organs of metformin are very limited: it can only act on the liver and the kidney, while having no regulating effect on AMPK in the tissues such as fat and muscle which are closely related to the metabolic regulation. Therefore, the search for a wider range of AMPK activators has been a hot issue in academia and industry, and it is urgent to design and develop AMPK activators having novel structures, high safety and high activity by new ideas.

SUMMARY OF INVENTION

In order to find new AMPK activators, after extensive and in-depth research, the inventors of the present invention have designed and synthesized a series of polysubstituted fluorine-containing imidazole salt derivatives having novel structures, high safety and high activity, and have studied effect on AMPK signaling pathway of this novel type of derivatives.

The present invention provides a compound having the general formula:

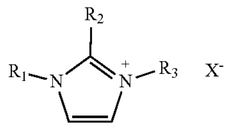

or a stereoisomer thereof, a prodrug thereof, a pharmaceutically acceptable salt thereof or a pharmaceutically acceptable solvate thereof.

The definitions of substituents and symbols are described in detail below.

One object of the present invention is to provide a compound having activity of activating 5'-adenosine monophosphate-activated protein kinase (AMPK) and a stereoisomer thereof, a prodrug thereof, a pharmaceutically acceptable salt thereof or a pharmaceutically acceptable solvate thereof.

Another object of the present invention is to provide a method for the preparation of the above compound.

Another object of the present invention is to provide a pharmaceutical composition comprising the above compound.

Another object of the present invention is to provide use of the above compound and the pharmaceutical composition comprising the compound in the manufacture of a medicament having activity of activating 5'-adenosine monophosphate-activated protein kinase (AMPK).

Another object of the present invention is to provide use of the above compound and the pharmaceutical composition comprising the compound in the manufacture of a medicament for reducing fatty acid synthesis, for inhibiting triglyceride and cholesterol synthesis, for preventing and/or treating obesity and type II diabetes, for, preventing and/or treating tumor, for preventing and/or treating Parkinson's disease, for preventing and/or treating Alzheimer's disease or for prolonging the lifespan of mammals.

DESCRIPTION OF THE DRAWINGS

FIG. 1 shows that the compounds can activate AMPK in mouse embryonic fibroblasts (MEFs). The results show that the tested compounds at 10 nM are effective in activating AMPK, and promoting phosphorylation of AMPK (p-AMPK) and phosphorylation of its downstream substrate ACC1/ACC2 (p-ACC).

FIG. 7 shows that the compound (IB-33) is effective in lowering blood sugar in ip-GTT.

DETAILED DESCRIPTION

Figure 1:
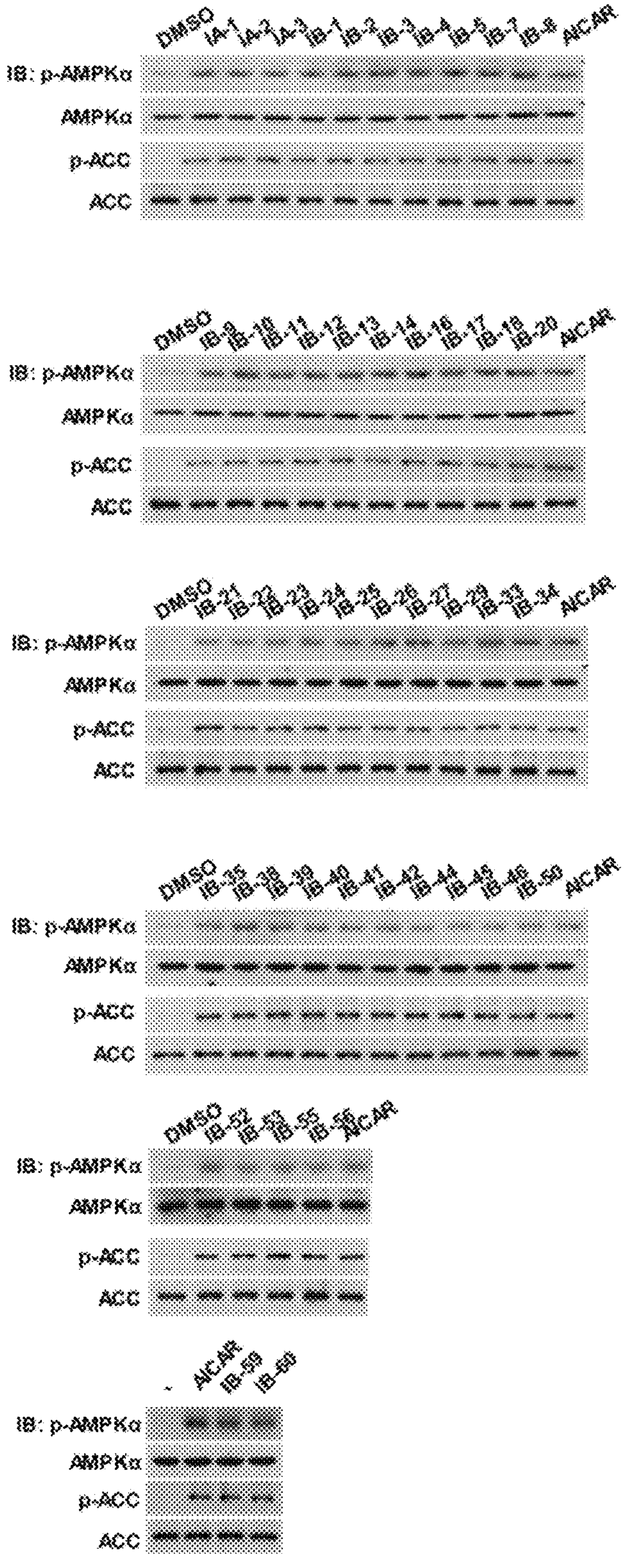
FIG. 1 shows the level of AMPK activation by representative compounds in MEF cells.
Figure 2:
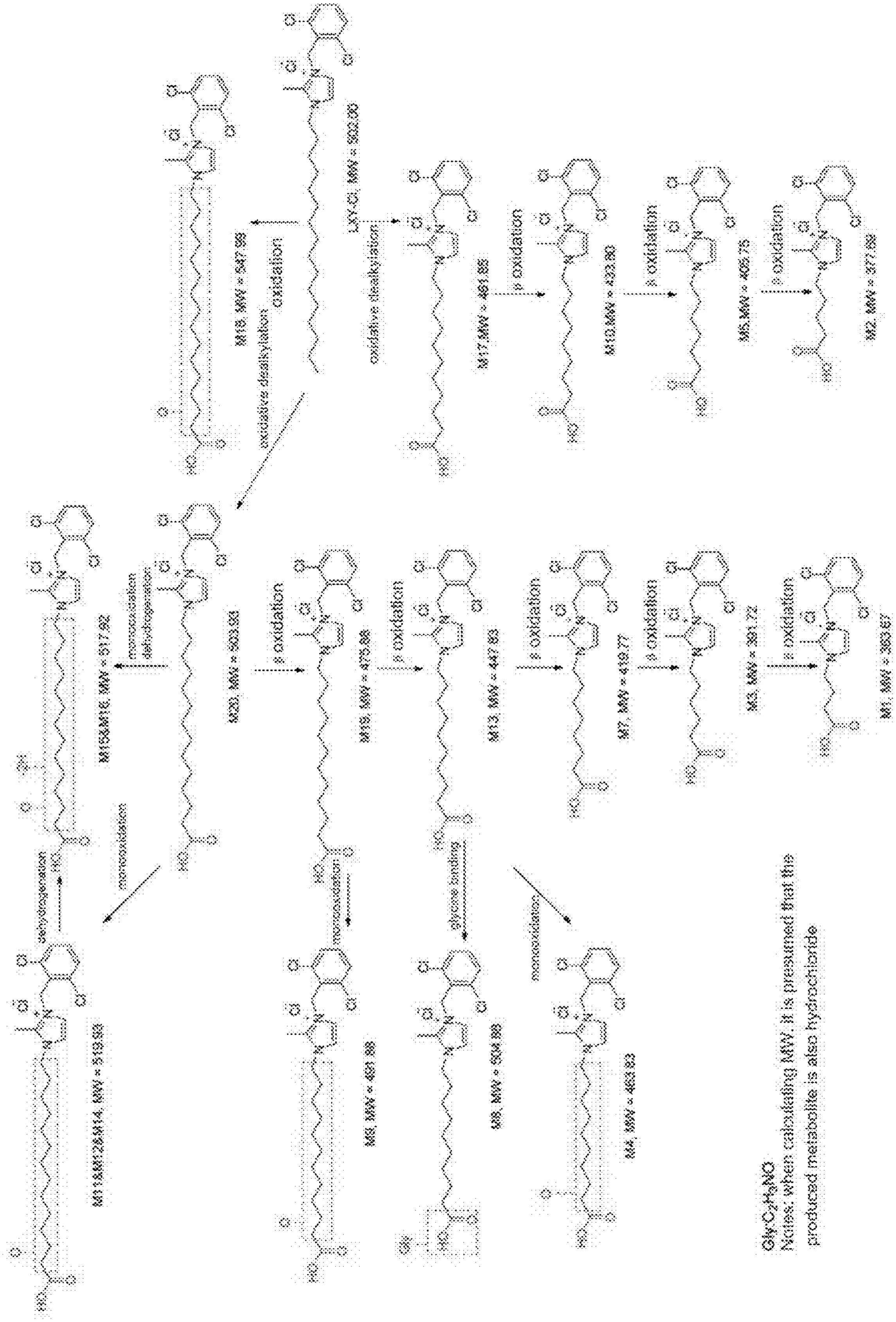
FIG. 2 shows possible metabolic pathways of LXY-CI in human hepatocyte incubation systems. The results show that LXY-CI can be metabolized into various metabolites in human hepatocytes, and the relative content of original drug remained is 21% after incubation for 120 min.
Figure 3:
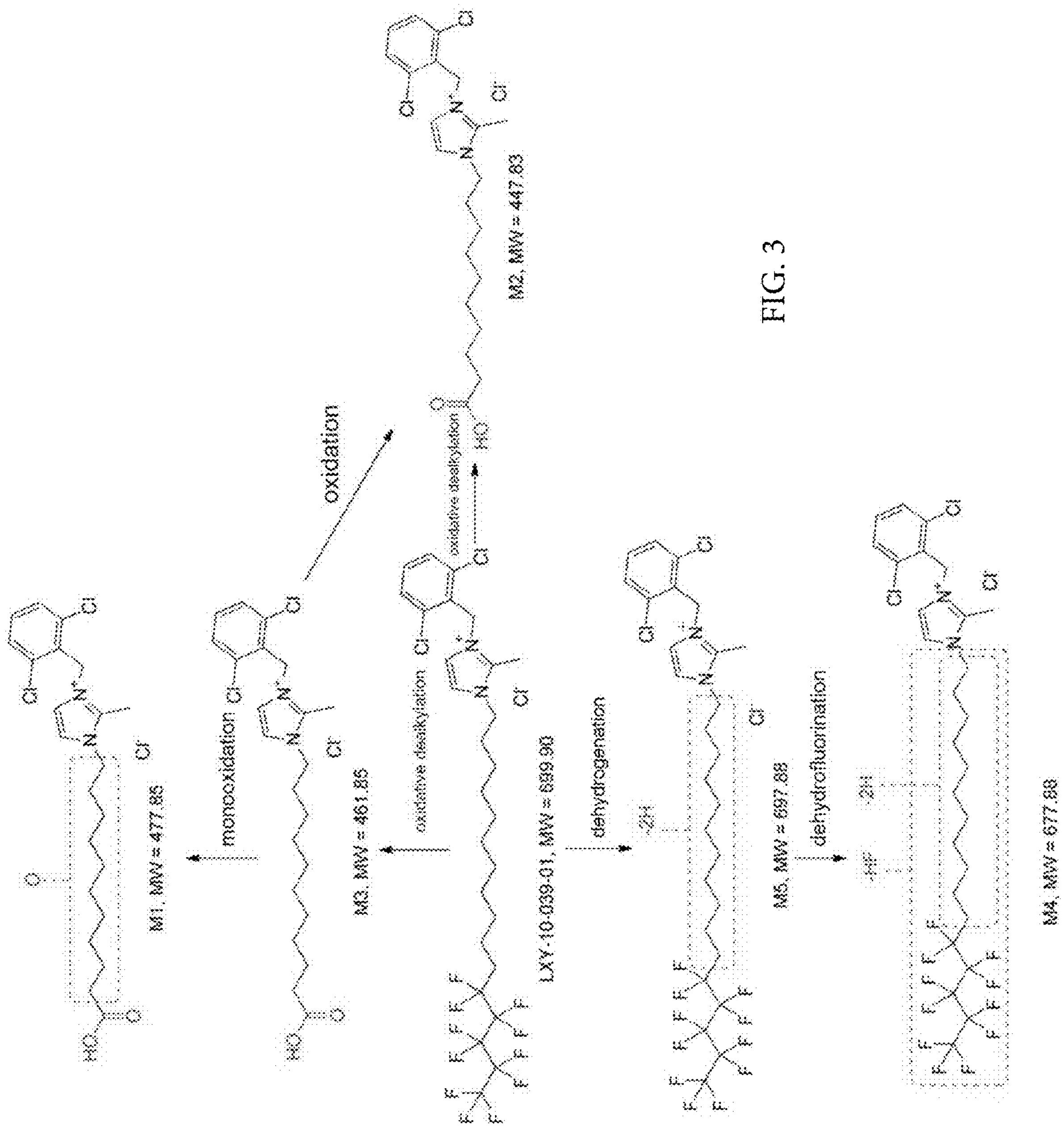
FIG. 3 shows possible metabolic pathways of IB-33 in human hepatocyte incubation systems. The results show that IB-33, i.e., a corresponding fluorine-substituted compound of LXY-CI, is relatively stable in human hepatocytes, and the relative content of original drug remained is 79% after incubation for 120 min. The comparison of the metabolite data of IB-33 and LXY-CI in hepatocytes shows that the metabolic stability of the fluorine-substituted compound is significantly improved.

Various specific embodiments, modes and examples are described herein, including exemplary embodiments and definitions, to understand the claimed invention. While the following detailed description sets forth specific preferred embodiments, those skilled in the art will appreciate that these embodiments are illustrative only, and that the present invention can be practiced in other ways. For the purpose of determining infringement, the scope of the present invention will cover any one or more of the appended claims, including equivalents thereof, and elements or limitations equivalent to those recited.

The present invention is achieved by the following technical solutions.

In one aspect, the present invention provides a compound having the general formula:

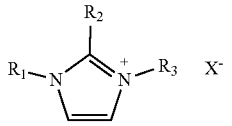

or a stereoisomer thereof, a prodrug thereof, a pharmaceutically acceptable salt thereof or a pharmaceutically acceptable solvate thereof, wherein, $R_1$ is selected from C10-C20 alkyl substituted by 1 to 15 fluorine atoms;

$R_2$ is selected from H, C1-C6 alkyl, C3-C6 cycloalkyl;

$R_3$ is selected from

1)

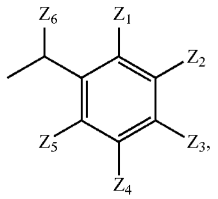

wherein $Z_1$, $Z_2$, $Z_3$, $Z_4$, $Z_5$ each are independently selected from:

(1) H, fluoro, chloro, bromo, iodo, nitro, cyano, amino, hydroxy, hydroxyformyl, methoxyformyl, ethoxyformyl, n-propoxyformyl, isopropoxyformyl, aminoformyl, N-methylformyl, N-ethylformyl, N-n-propylformyl, N-isopropylformyl, N-cyclopropylformyl, N-n-butylformyl, N-isobutylformyl, N-t-butylformyl, N-cyclobutylformyl, N-n-pentylformyl, N-isopentylformyl, N-cyclopentylformyl, N-n-hexylformyl, N-isohexylformyl, N-cyclohexylformyl, N,N-dimethylformyl, N,N-diethylformyl, N,N-di-n-propylformyl, N,N-diisopropylformyl, cyclopropylaminoformyl, cyclobutylaminoformyl, cyclopentylaminoformyl, cyclohexylaminoformyl, 4-hydroxypiperidinylformyl, piperazinylformyl, 4-N-methylpiperazinylformyl, 4-N-ethylpiperazinylformyl, 4-N-n-propylpiperazinylformyl, 4-N-isopropylpiperazinylformyl, methanesulfonyl, ethanesulfonyl, n-propylsulfonyl, isopropylsulfonyl, n-butylsulfonyl, isobutylsulfonyl, hydroxysulfonyl, aminosulfonyl, N-methylsulfonyl, N-ethylsulfonyl, N-n-propylsulfonyl, N-isopropylsulfonyl, N-cyclopropylsulfonyl, N-n-butylsulfonyl, N-isobutylsulfonyl, N-t-butylsulfonyl, N-cyclobutylsulfonyl, N-n-pentylsulfonyl, N-isopentylsulfonyl, N-cyclopentylsulfonyl, N-n-hexylsulfonyl, N-isohexylsulfonyl, N-cyclohexylsulfonyl, N,N-dimethylsulfonyl, N,N-diethylsulfonyl, N,N-di-n-propylsulfonyl, N,N-diisopropylsulfonyl, cyclopropylaminosulfonyl, cyclobutylaminosulfonyl, cyclopentylaminosulfonyl, cyclohexylaminosulfonyl, 4-hydroxypiperidinylsulfonyl, piperazinylsulfonyl, 4-N-methylpiperazinylsulfonyl, 4-N-ethylpiperazinylsulfonyl, 4-N-n-propylpiperazinylsulfonyl, 4-N-isopropylpiperazinylsulfonyl, formamido, acetylamino, propionamido, n-butyramido, isobutyramido, cyclopropylformamido, cyclobutylformamido, cyclopentylformamido, cyclohexylformamido, methanesulfonamido, ethanesulfonamido, n-propanesulfonamido, isopropanesulfonamido, n-butanesulfonamido, isobutanesulfonamido;

(2) C1-C6 alkyl, C1-C6 alkoxy, C1-C6 oxygen-containing alkyl, C1-C6 fluorine-containing alkyl, C1-C6 fluorine-containing alkoxy;

(3) $Z_2$ and $Z_3$ may form an oxygen-containing substituted or unsubstituted five- or six-membered ring; the substituent may be selected from the same substituents as $Z_1$;

(4) $Z_4$ and $Z_5$ may form a nitrogen-containing substituted or unsubstituted five- or six-membered ring; the substituent may be selected from the same substituents as $Z_1$;

$Z_6$ is selected from H, C1-C3 alkyl, C3-C6 cycloalkyl;

2)

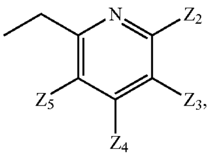

wherein $Z_2$, $Z_3$, $Z_4$, $Z_5$ are defined the same as in 1);

3)

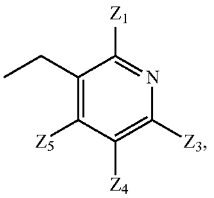

wherein $Z_2$, $Z_3$, $Z_4$, $Z_5$ are defined the same as in 1);

4)

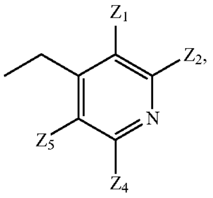

wherein $Z_2$, $Z_3$, $Z_4$, $Z_5$ are defined the same as in 1);

$X^-$ is an anion of a pharmaceutically acceptable inorganic or organic acid salt.

In some embodiments, $R_1$ is selected from: C14-C18 alkyl substituted by 1, 3, 5, 7, 9, 11, 13 or 15 fluorine atoms.

In some embodiments, $R_1$ is selected from: $C_{16}FH_{32}$—, $C_{14}F_7H_{22}$—, $C_{15}F_9H_{22}$—, $C_{16}F_{11}H_{22}$—, $C_{17}F_{13}H_{22}$—.

In some embodiments, $R_2$ is selected from: H, C1-C4 alkyl, C3-C4 cycloalkyl.

In some embodiments, $R_2$ is selected from: H, methyl, isopropyl, cyclopropyl.

In some embodiments, $R_3$ is

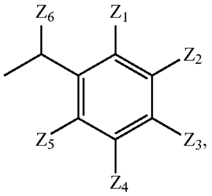

wherein any two of $Z_1$, $Z_2$, $Z_3$, $Z_4$, $Z_5$ each are independently selected from the following groups, the rest being H:

(1) H, fluoro, chloro, bromo, iodo, nitro, cyano, amino, hydroxy, hydroxyformyl, aminoformyl, methanesulfonyl, hydroxysulfonyl, aminosulfonyl, formamido, methanesulfonamido;

(2) C1-C6 alkyl, C1-C6 alkoxy, C1-C6 oxygen-containing alkyl, C1-C6 fluorine-containing alkyl, C1-C6 fluorine-containing alkoxy;

$Z_6$ is selected from H, C1-C3 alkyl, C3-C6 cycloalkyl; preferably $Z_6$ is H or methyl.

In some embodiments, $R_3$ is

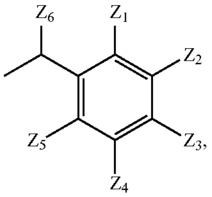

wherein any two of $Z_1$, $Z_2$, $Z_4$, $Z_5$ each are independently selected from the following groups, the rest and $Z_3$ being H:

(1) H, fluoro, chloro, bromo, iodo, nitro, cyano, amino, hydroxy, hydroxyformyl, aminoformyl, methanesulfonyl, hydroxysulfonyl, aminosulfonyl, formamido, methanesulfonamido;

(2) C1-C6 alkyl, C1-C6 alkoxy, C1-C6 oxygen-containing alkyl, C1-C6 fluorine-containing alkyl, C1-C6 fluorine-containing alkoxy;

$Z_6$ is selected from H, C1-C3 alkyl, C3-C6 cycloalkyl; preferably $Z_6$ is H or methyl.

In some embodiments, $R_3$ is

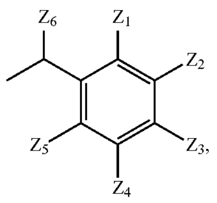

wherein, $Z_1$, $Z_5$, or $Z_2$, $Z_4$, or $Z_1$, $Z_4$ in $Z_1$, $Z_2$, $Z_3$, $Z_4$, $Z_5$ each are independently selected from the following groups, the rest being H:

(1) H, fluoro, chloro, bromo, iodo, nitro, cyano, amino, hydroxy, hydroxyformyl, aminoformyl, methanesulfonyl, hydroxysulfonyl, aminosulfonyl, formamido, methanesulfonamido;

(2) C1-C6 alkyl, C1-C6 alkoxy, C1-C6 oxygen-containing alkyl, C1-C6 fluorine-containing alkyl, C1-C6 fluorine-containing alkoxy;

$Z_6$ is selected from H, C1-C3 alkyl, C3-C6 cycloalkyl; preferably $Z_6$ is H or methyl.

In some embodiments, $X^-$ is chloride ion, bromide ion, iodide ion, sulfate ion, phosphate ion, maleate ion, fumarate ion, tartrate ion, palmitate ion, oxalate ion, citrate ion, succinate ion, methanesulfonate ion, benzenesulfonate ion, p-toluenesulfonate ion.

In some embodiments, $X^-$ is chloride ion, bromide ion, iodide ion, bisulfate ion, sulfate ion, phosphate ion, maleate ion, fumarate ion, tartrate ion, palmitate ion, oxalate ion, citrate ion, succinate ion, methanesulfonate ion, benzenesulfonate ion, p-toluenesulfonate ion.

In a second aspect, the present invention provides a compound having the general formula:

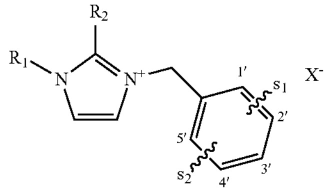

a stereoisomer thereof, a prodrug thereof, a pharmaceutically acceptable salt thereof or a pharmaceutically acceptable solvate thereof wherein, $R_1$ is selected from C10-C20 alkyl substituted by 1 to 15 fluorine atoms;

$R_2$ is selected from: H, C1-C6 alkyl, C3-C6 cycloalkyl;

$S_1$ is selected from: 1'-halogen, 1'-C1-C6 alkoxy (preferably 1'-C1-C3 alkoxy);

$S_2$ is selected from: 4'-halogen, 5'-halogen;

$X^-$ is an anion of a pharmaceutically acceptable inorganic or organic acid salt.

In some embodiments, $R_1$ is selected from: C14-C18 alkyl substituted by 1, 3, 5, 7, 9, 11, 13 or 15 fluorine atoms.

In some embodiments, $R_1$ is selected from: $C_{16}FH_{32}$—, $C_{14}F_7H_{22}$—, $C_{15}F_9H_{22}$—, $C_{16}F_{11}H_{22}$—, $C_{17}F_{13}H_{22}$—.

In some embodiments, $R_1$ is selected from: n-$C_{16}FH_{32}$—, n-$C_{14}F_7H_{22}$—, n-$C_{15}F_9H_{22}$—, n-$C_{16}F_{11}H_{22}$—, n-$C_{17}F_{13}H_{22}$—.

In some embodiments, preferably $R_2$ is selected from: H, C1-C3 alkyl, C3-C4 cycloalkyl.

In some embodiments, $R_2$ is selected from: H, methyl, isopropyl, cyclopropyl.

In some embodiments, $S_1$, $S_2$ each are selected from: 1'-halogen, 5'-halogen, or 1'-C1-C6 alkoxy (preferably 1'-C1-C3 alkoxy), 4'-halogen.

In some embodiments, $X^-$ is chloride ion, bromide ion, iodide ion, sulfate ion, phosphate ion, maleate ion, fumarate ion, tartrate ion, palmitate ion, oxalate ion, citrate ion, succinate ion, methanesulfonate ion, benzenesulfonate ion, p-toluenesulfonate ion.

In some embodiments, $X^-$ is chloride ion, bromide ion, iodide ion, bisulfate ion, sulfate ion, phosphate ion, maleate ion, fumarate ion, tartrate ion, palmitate ion, oxalate ion, citrate ion, succinate ion, methanesulfonate ion, benzenesulfonate ion, p-toluenesulfonate ion.

In a third aspect, the present invention provides compounds having the general formulas:

IA

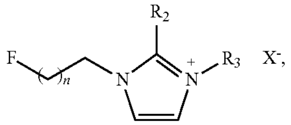

IB

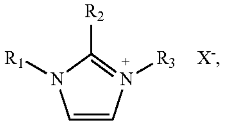

wherein, $R_1$, $R_2$, $R_3$ and $X^-$ are as defined above, n=9~19, or a stereoisomer thereof, a prodrug thereof, a pharmaceutically acceptable salt thereof or a pharmaceutically acceptable solvate thereof.

Unless otherwise indicated, the above groups and substituents have the ordinary meanings in the field of medicinal chemistry.

The term "$C_{10}$-$C_{20}$ alkyl" includes straight-chain or branched-chain groups having a number of carbon atoms within intervals of any two integers in the range of 10 to 20 as endpoints. For example, "$C_{10}$-$C_{20}$ alkyl" includes $C_{14}$-$C_{18}$ alkyl, $C_{10}$-$C_{18}$ alkyl, $C_{10}$-$C_{16}$ alkyl, $C_1$-$C_4$ alkyl, $C_2$-$C_{20}$ alkyl, $C_2$-$C_{16}$ alkyl, $C_6$-$C_{20}$ alkyl, $C_6$-$C_{16}$ alkyl, and etc. The above list is by way of example only and is not to limit the intervals.

The term "C10-C20 alkyl substituted by 1 to 15 fluorine atoms" refers to the above-mentioned "$C_{10}$-$C_{20}$ alkyl" substituted by 1, 2, 3, 4, 5, 6, 7, 8, 9, 10, 11, 12, 13, 14 or 15 fluorine atoms.

The term "$C_1$-$C_6$ alkyl" refers to any straight-chain or branched-chain group having 1 to 6 carbon atoms, such as methyl, ethyl, n-propyl, isopropyl, n-butyl, isobutyl, t-butyl, sec-butyl, n-pentyl, tert-amyl, n-hexyl and the like.

The term "$C_1$-$C_4$ alkyl" refers to any straight-chain or branched-chain group having 1 to 4 carbon atoms, such as methyl, ethyl, n-propyl, isopropyl, n-butyl, isobutyl, t-butyl, sec-butyl and the like.

The term "$C_1$-$C_3$ alkyl" refers to any straight-chain or branched-chain group having 1 to 3 carbon atoms, such as methyl, ethyl, n-propyl, isopropyl and the like.

The term "$C_3$-$C_6$ cycloalkyl" refers to a 3- to 6-membered all-carbon monocyclic ring that may contain zero, one or more double bonds, but does not have a fully conjugated π-electron system. Examples of cycloalkyl include, but are not limited to, cyclopropyl, cyclobutyl, cyclopentyl, cyclopentenyl, cyclohexyl, cyclohexenyl, cyclohexadienyl.

The term "$C_3$-$C_4$ cycloalkyl" refers to a 3- to 4-membered all-carbon monocyclic ring. Examples of cycloalkyl include, but are not limited to, cyclopropyl, cyclobutyl.

The term "halogen" refers to fluorine, chlorine, bromine, iodine.

The term "cyano" refers to —CN residue.

The term "nitro" refers to —$NO_2$ group.

The terms "alkoxy", "cycloalkoxy" and derivatives thereof refer to any of the above-mentioned alkyl (for example, $C_1$-$C_{24}$ alkyl, $C_1$-$C_6$ alkyl and the like), cycloalkyl (for example, $C_3$-$C_6$ cycloalkyl), which is attached to the remainder of molecules through oxygen atom (—O—).

From all of the above description, it will be apparent to those skilled in the art that any group whose name is a compound name, for example, "fluorine-containing oxygen-containing alkyl" shall mean a moiety constructed from a derived moiety, such as the oxygen-containing alkyl substituted by the fluoro, wherein the alkyl is as defined above.

The term "oxygen-containing substituted or unsubstituted five- or six-membered ring" or "nitrogen-containing substituted or unsubstituted five- or six-membered ring" refers to five- or six-membered saturated or partially unsaturated carbon ring, wherein one or more carbon atoms are reput by oxygen or nitrogen. Non-limiting examples are, for example, pyran, pyrrolidine, pyrroline, imidazoline, imidazolidine, pyrazolidine, pyrazoline, dihydrofuran, tetrahydrofuran, 1,3-dioxolan, piperidine, piperazine, morpholine, tetrahydropyrrole, etc.

In the above definitions of $Z_1$, $Z_2$, $Z_3$, $Z_4$, $Z_5$ for $R_3$, the expression "wherein, $Z_1$, $Z_5$, or $Z_2$, $Z_4$, or $Z_1$, $Z_4$ in $Z_1$, $Z_2$, $Z_3$, $Z_4$, $Z_5$ each are independently selected from the following groups, the rest being H: (1) H, F, Cl, Br, I, nitro, cyano; (2) C1-C6 alkyl, C1-C6 alkoxy, C1-C6 oxygen-containing alkyl, C1-C6 fluorine-containing alkyl, C1-C6 fluorine-containing alkoxy" is meant that: "$Z_1$, $Z_5$ each are independently selected from" includes that $Z_1$, $Z_5$ each are independently any combination of any groups listed in "(1) H, F, Cl, Br, I, nitro, cyano; (2) C1-C6 alkyl, C1-C6 alkoxy, C1-C6 oxygen-containing alkyl, C1-C6 fluorine-containing alkyl, C1-C6 fluorine-containing alkoxy", "$Z_2$, $Z_4$ each are independently selected from" includes that $Z_2$, $Z_4$ each are independently any combination of any groups listed in "(1) H, F, Cl, Br, I, nitro, cyano; (2) C1-C6 alkyl, C1-C6 alkoxy, C1-C6 oxygen-containing alkyl, C1-C6 fluorine-containing alkyl, C1-C6 fluorine-containing alkoxy", "$Z_1$, $Z_4$ each are independently selected from" includes that $Z_1$, $Z_4$ each are independently any combination of any groups listed in "(1) H, F, Cl, Br, I, nitro, cyano; (2) C1-C6 alkyl, C1-C6 alkoxy, C1-C6 oxygen-containing alkyl, C1-C6 fluorine-containing alkyl, C1-C6 fluorine-containing alkoxy".

As used herein, unless otherwise indicated, the term "prodrug" refers to a derivative that can be hydrolyzed, oxidized or otherwise reacted under biological conditions (in vitro or in vivo) to provide a compound of the invention. Prodrugs can become active compounds only by carrying out the reaction under biological conditions, or they are inactive in their non-reacted form. Prodrugs can be generally prepared using known methods, for example, those methods described in Burger's Medicinal Chemistry and Drug Discovery (1995) 172-178, 949-982 (Manfred E. Wolff, ed. $5^{th}$ edition).

As used herein, examples of the term "pharmaceutically acceptable salts of the compounds of formula (I)" are organic acid addition salts formed from organic acids that form pharmaceutically acceptable anions, including but not limited to formate, acetate, propionate, benzoate, maleate, fumarate, succinate, tartrate, citrate, ascorbate, α-ketoglutarate, α-glycerophosphate, alkyl sulfonate or aryl sulfonate; preferably, said alkyl sulfonate is methyl sulfonate or ethyl sulfonate; said aryl sulfonate is benzenesulfonate or p-toluenesulfonate. Suitable inorganic acid salts may also be formed, including but not limited to hydrochloride, hydrobromide, hydroiodide, nitrate, bicarbonate and carbonate, bisulfate, sulfate or phosphate and the like.

Pharmaceutically acceptable salts can be obtained using standard procedures well known in the art, for example, by reacting a sufficient amount of a basic compound with a suitable acid that provides a pharmaceutically acceptable anion.

The term "treatment" as used herein generally refers to obtaining the desired pharmacological and/or physiological effect. The effect may be preventive according to complete or partial prevention of disease or its symptoms; and/or may be therapeutic according to partial or complete stabilization or cure of disease and/or side effects due to the disease. The term "treatment" as used herein encompasses any treatment on a patient's disease, including: (a) preventing the disease or symptom that occurs in a patient who is susceptible to the disease or symptom but not yet diagnosed to suffer from the disease; (b) suppressing symptoms of the disease, i.e., stopping its development; or (c) relieving symptoms of the disease, i.e., causing degeneration of the disease or symptom.

According to a specific embodiment of the present invention relating to the compound, a stereoisomer thereof, a prodrug thereof, or a pharmaceutically acceptable salt thereof or a pharmaceutically acceptable solvate thereof, the compound is one of the compounds described in the examples below.

In another aspect, the present invention provides a pharmaceutical composition comprising the compound, a stereoisomer thereof, a prodrug thereof, or a pharmaceutically acceptable salt thereof or pharmaceutically acceptable solvate thereof according to any one of the above embodiments, and a pharmaceutically acceptable carrier, diluent or excipient.

Methods for preparing a pharmaceutical composition comprising a certain amount of an active ingredient, are known or are obvious for a person skilled in the art according to the contents as disclosed in the invention. For example, as described in REMINGTON'S PHARMACEUTICAL SCIENCES, Martin, E. W., ed., Mack Publishing Company, $19^{th}$ ed. (1995), methods for preparing a pharmaceutical composition comprise incorporating a suitable pharmaceutically acceptable excipient, carrier, diluent, etc.

The known methods for preparing a pharmaceutical preparation according to the invention include the conventional mixing, dissolving or freeze-drying methods. The compound according to the invention can be used to prepare into a pharmaceutical composition, which is administered to a patient by various routes suitable for the selected administration mode, for example, oral, or parenteral route (intravenous, intramuscular, topical, or subcutaneous route).

Therefore, the compound of the invention in combination with a pharmaceutically acceptable carrier (such as an inert diluent or an assimilable edible carrier) can be administered systemically, e.g., orally. They can be encapsulated into a hard or soft shell gelatin capsule, or pressed into a tablet. For the treatment by oral administration, an active compound may be combined with one or more excipients, and be used in a form of a deglutible tablet, a buccal tablet, a troche, a capsule, an elixir, a suspension, a syrup, a wafer, etc. The composition and preparation shall comprise at least 0.1% of an active compound. The ratio of the composition to the preparation can be varied certainly, and the composition may account for about 1 wt % to about 99 wt % of a given unit dosage form. In such a therapeutically active composition, the active compound is in an amount sufficient to obtain an effective dosage level.

A tablet, a troche, a pill, a capsule, and the like may include: a binder, such as tragacanth gum, arabic gum, maize starch or gelatin; an excipient, such as dicalcium phosphate; a disintegrant, such as maize starch, potato starch, and alginic acid etc; a lubricant, such as magnesium stearate; and a sweeting agent, such as sucrose, fructose, lactose or aspartame; or a flavoring agent, such as peppermint, winter green oil or cherry flavor. When the unit dosage form is a capsule, in addition to the above types of materials, it may comprise a liquid carrier, such as vegetable oil or polyethylene glycol. Various other materials may be present as a coating or change the physical form of a solid unit dosage form in other manners. For example, a tablet, a pill or a capsule may be coated with gelatin, wax, shellac or sugar etc. A syrup or elixir may comprise an active compound, sucrose or fructose as a sweeting agent, methyl p-hydroxybenzoate or propyl p-hydroxybenzoate as preservative, a dye and a flavoring agent (such as a cherry flavor or an orange flavor). Certainly, any material for preparing any unit dosage form should be pharmaceutically acceptable and be substantively not toxic in its applied amount. In addition, an active compound may be incorporated into a sustained release preparation and a sustained release device.

An active compound may also be administered intravenously or intraperitoneally by infusion or injection. An aqueous solution of an active compound or a salt thereof may be prepared, optionally, by mixing it with a non-toxic surfactant. A dispersible formulation in glycerol, liquid polyethylene glycol, glycerin triacetate and a mixture thereof and in oil may also be prepared. Under the common conditions of storage and use, the preparations may comprise a preservative in order to suppress the growth of microbes.

A pharmaceutical dosage form suitable for injection or infusion may include a sterile aqueous solution or a dispersible formulation or a sterile powder comprising an active ingredient (optionally encapsulated into a liposome) of an immediate preparation such as a solvent or a dispersible formulation suitable for sterile injection or infusion. Under all the conditions, the final dosage form shall be sterile, liquid and stable under the production and storage conditions. A liquid carrier may be a solution or a liquid disperse medium, including, for example, water, ethanol, polyols (such as glycerol, propylene glycol, and liquid macrogol, etc), vegetable oil, a non-toxic glyceride and a suitable mixture thereof. A suitable fluidity may be retained, for example, by the formation of liposome, by retaining the desired particle size in the presence of a dispersing agent, or by using a surfactant. The effect of suppressing microbes can be obtained by various antibacterial agents and antifungal agents (such as paraben, chlorbutol, phenol, sorbic acid, and thiomersal, etc). In many conditions, an isotonizing agent, such as sugar, buffer agent or NaCl, is preferably comprised. By the use of a composition of delayed absorbents (e.g., aluminium monostearate and gelatin), an extended absorption of an injectable composition can be obtained.

A sterile injectable solution can be prepared by mixing a desired amount of an active compound in a suitable solvent with the desired various other ingredients as listed above, and then performing filtration and sterilization. In the case of a sterile powder for the preparation of a sterile injectable solution, the preferred preparation method is vacuum drying and freeze drying techniques, which will result in the production of the powder of the active ingredient and any other desired ingredient present in the previous sterile filtration solution.

A useful solid carrier includes crushed solid (such as talc, clay, microcrystalline cellulose, silicon dioxide, and aluminum oxide etc). A useful liquid carrier includes water, ethanol or ethylene glycol or water-ethanol/ethylene glycol mixture, in which the compound of the invention may be dissolved or dispersed in an effective amount, optionally, with the aid of a non-toxic surfactant. An adjuvant (such as a flavor) and an additional antimicrobial agent may be added to optimize the property for a given use.

A thickener (such as synthetic polymer, fatty acid, fatty acid salt and ester, fatty alcohol, modified cellulose or modified inorganic material) may also be used with a liquid carrier to form a coatable paste, gel, ointment, soap and the like, and be directly applied to the skin of a user.

A therapeutically effective amount of a compound or an active salt or derivative thereof not only depends on the specific salt selected, but also depends on the administration mode, the nature of the disease to be treated and the age and state of a patient, and finally depends on the decision made by an attending physician or a clinical physician.

Above preparation may be present in a unit dosage form, which is a physical dispersion unit comprising a unit dose, suitable for administration to a human body and other mammalian body. A unit dosage form may be capsule(s) or tablet(s). Depending on the particular treatment involved, the amount of an active ingredient in a unit dose may be varied or adjusted between about 0.1 and about 1000 mg or more.

In addition, the present invention further includes use of various new drug dosage forms such as milk liposomes, microspheres and nanospheres, for example, medicaments prepared with the use of a particulate dispersion system including polymeric micelles, nanoemulsions, submicroemulsions, microcapsules, microspheres, liposomes and niosomes (also known as nonionic surfactant vesicles), etc.

In another aspect, the present invention further provides a preparation method of the compound according to any of the above embodiments, comprising the following steps:

Scheme I

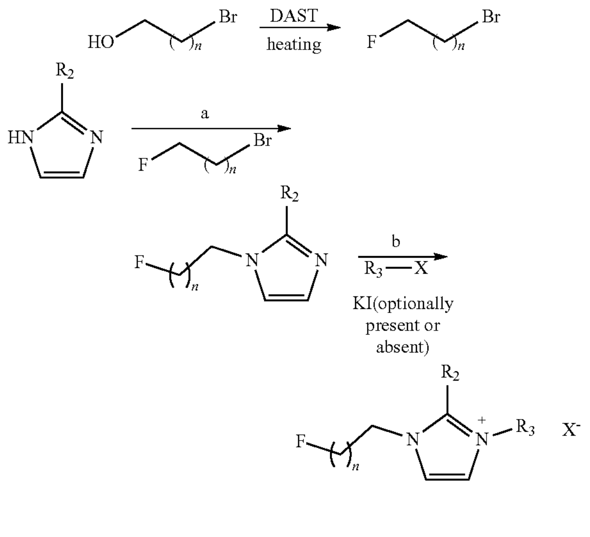

reaction conditions: (a) substitution reaction of brominated hydrocarbons; (b) substitution reaction of brominated hydrocarbons.

Scheme II

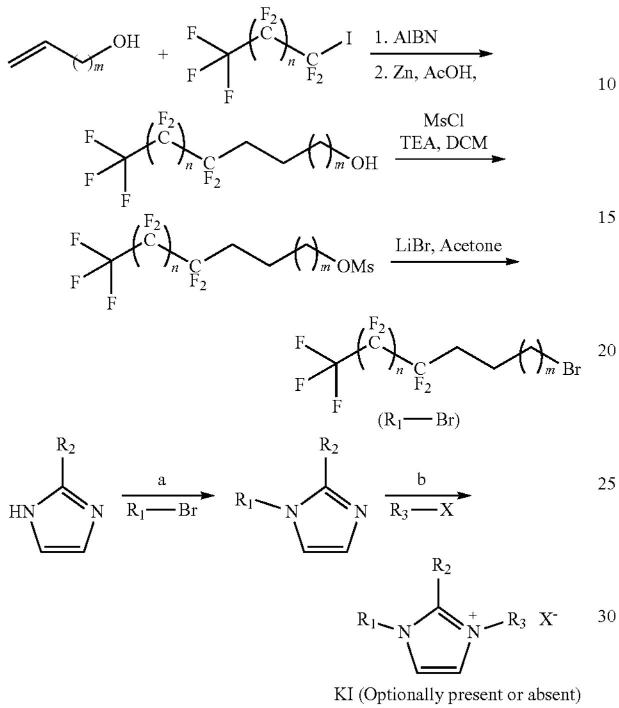

reaction conditions: (a) substitution reaction of brominated hydrocarbons under alkaline condition (such as sodium hydride, sodium t-butoxide and the like); (b) substitution reaction of brominated hydrocarbons.

In another aspect, the present invention further provides use of the compound according to any one of the above embodiments, a stereoisomer thereof, a prodrug thereof, or a pharmaceutically acceptable salt thereof or a pharmaceutically acceptable solvate thereof, and a pharmaceutical composition comprising the compound in the manufacture of a medicament for inhibiting cholesterol synthesis, for lowering fatty acid synthesis, for preventing and/or treating obesity, for preventing and/or treating diabetes, for preventing and/or treating tumor, for preventing and/or treating Parkinson's disease, for preventing and/or treating Alzheimer's disease or for prolonging the lifespan of mammals.

Experimental Section

Regarding the examples described below, the compounds of the present invention are synthesized using the methods described herein or other methods well known in the art.

General Methods of Purification and Analysis

Thin layer chromatography was carried out on a silica gel GF254 precoated plate (Qingdao Marine Chemical Plant). Column chromatography was carried out by silica gel (300-400 mesh, Yantai Zhihuangwu Silica Gel Development Reagent Factory) under medium pressure or by a pre-packed silica gel cartridge (ISCO or Welch) with the use of an ISCO Combiflash Rf200 rapid purification system. The ingredient was developed by UV light (λ: 254 nm) or iodine vapor. When necessary, the compound was prepared by preparative HPLC and purified by a Waters Symmetry C18 (19×50 mm, 5 μm) column or a Waters X Terra RP 18 (30×150 mm, 5 μm) column, wherein a Waters preparative HPLC 600 equipped with a 996 Waters PDA detector and Micromass mod. ZMD single quadrupole mass spectrometry (electrospray ionization, cationic mode) were used. Method 1: Phase A: 0.1% TFA/MeOH 95/5; Phase B: $MeOH/H_2O$ 95/5. Gradient: proceeding at 10 to 90% B for 8 min, keeping at 90% B for 2 min; flow rate 20 mL/min. Method 2: Phase A: 0.05% $NH_4OH/MeOH$ 95/5; Phase B: $MeOH/H_2O$ 95/5. Gradient: proceeding at 10 to 100% B for 8 min, keeping at 100% B for 2 min. Flow rate 20 mL/min.

$^1$H-NMR spectra were recorded in DMSO-$d_6$ or $CDCl_3$ via a Bruker Avance 600 spectrometer (for $^1$H) operated at 600 MHz. The residual solvent signal was used as a reference (δ=2.50 or 7.27 ppm). Chemical shift (δ) was reported in parts per million (ppm) and coupling constant (J) in Hz. The following abbreviations were used for peak splitting: s=single; br. s.=wide signal; d=double; t=triple; m=multiple; dd=double double.

Electrospray (ESI) Mass Spectra were Obtained Via Finnigan LCQ Ion Trap.

Unless otherwise indicated, all final compounds were homogeneous (with purity not less than 95%), as determined by high performance liquid chromatography (HPLC). HPLC-UV-MS analysis for evaluation of compound purity was performed by combining an ion trap MS device and an HPLC system SSP4000 (Thermo Separation Products) equipped with an autosampler LC Pal (CTC Analytics) and a UV6000LP diode array detector (UV detection 215-400 nm). Device control, data acquisition and processing were performed with Xcalibur 1.2 software (Finnigan). HPLC chromatography was carried out at room temperature and a flow rate of 1 mL/min using a Waters X Terra RP 18 column (4.6×50 mm; 3.5 μm). Mobile phase A was ammonium acetate 5 mM buffer (pH 5.5 with acetic acid): acetonitrile 90:10, mobile phase B was ammonium acetate 5 mM buffer (pH 5.5 with acetic acid): acetonitrile 10:90; proceeding at a gradient of 0 to 100% B for 7 min and then keeping at 100% B for 2 min before rebalancing.

Reagent purification was carried out in accordance with the book Purification of Laboratory Chemicals (Perrin, D. D., Armarego, W. L. F. and Perrins Eds, D. R.; Pergamon Press: Oxford, 1980). Petroleum ether was 60-90° C. fraction, ethyl acetate, methanol, dichloromethane were all analytically pure.

Mode of Carrying Out the Invention

The embodiments of the present invention are described in detail below by way of specific examples, but in any case they cannot be construed as limiting the present invention.

I

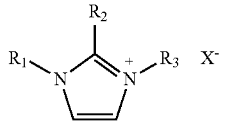

The above compound of formula was divided into two types for preparation.

IA

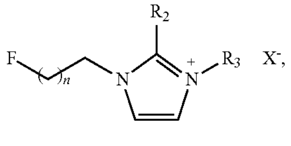

-continued

IB

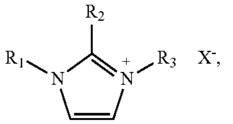

wherein, synthetic scheme I of compound IA is:

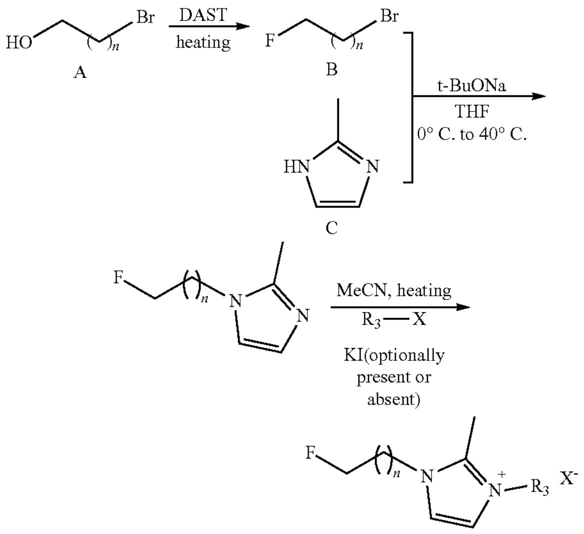

Diethylaminosulfur trifluoride DAST (2 eq) was weighed and put in a reaction bottle, compound A (1 eq) dissolved in dichoromethane was added to the reaction bottle at room temperature, then the reaction bottle was sealed, and purged with nitrogen, followed by stirring in an oil bath at 40° C. for 8 h. The reaction system was cooled to room temperature, poured into ice water, and extracted with dichoromethane. The resulting organic phase was washed once with saturated $NaHCO_3$ solution and saturated sodium chloride solution in sequence, dried with anhydrous sodium sulfate, filtered, concentrated, and then subjected to silica gel column chromatography (eluted with dichoromethane) to obtain compound B.

The compounds B (1 eq) and C (1 eq) were dissolved in THF, to which was added sodium tert-butoxide (2 eq) with stirring in an ice bath. After further stirring for 20 min, the reaction solution was stirred in an oil bath at 40° C. until complete reaction with TLC tracking. Then, the system was cooled to room temperature, to which were added saturated ammonium chloride solution and ethyl acetate for extraction. The resulting organic phase was washed once with water and saturated sodium chloride, dried with anhydrous sodium sulfate, filtered, concentrated, and then subjected to silica gel column chromatography (dichoromethane/methanol) to obtain compound D.

The compounds D (1 eq) and $R_3$—X (1.2 eq) were dissolved in acetonitrile, to which was optionally added potassium iodide (6 eq). After sealing, the reaction solution was stirred in an oil bath at 70° C. for 12 h. The system was cooled to room temperature, concentrated, and then subjected to silica gel column chromatography (dichoromethane/methanol) to obtain compound IA.

The implementation of the synthetic scheme I of compound IA is described as follows.

1. Compound IA-1:

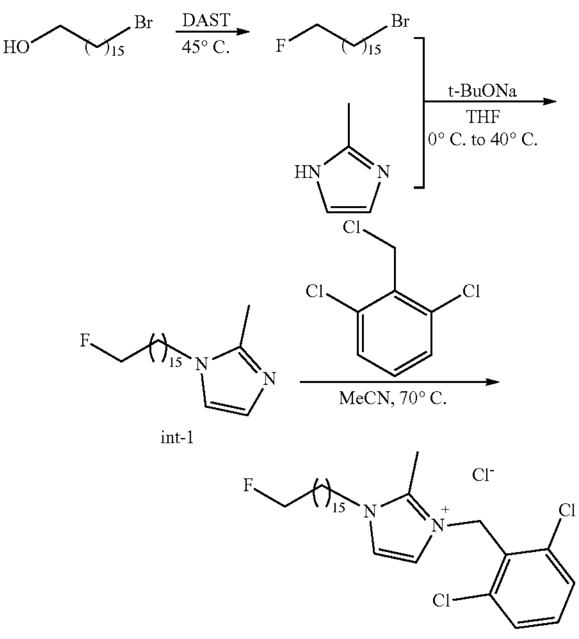

IA-1

16-bromo-1-hexadecanol (1606 mg, 5 mmol) (CAS: 59101-28-9, Aikon, Jiangsu) was dissolved in 4 mL of dichoromethane, and added dropwise to a microwave tube containing diethylaminosulfur trifluoride (1612 mg, 10 mmol) (CAS: 38078-09-0, Energy, Shanghai). The microwave tube was sealed, purged with nitrogen, and stirred in an oil bath at 40° C. for 8 h. The reaction system was cooled to room temperature, poured into ice water, and extracted with dichoromethane. The resulting organic phase was washed once with saturated $NaHCO_3$ solution and saturated sodium chloride solution in sequence, dried with anhydrous sodium sulfate, filtered, concentrated, and then subjected to silica gel column chromatography (eluted with dichoromethane). The resulting product was directly dissolved, together with 2-methylimidazole (410 mg, 5 mmol) as raw material A (Appendix 1), in 30 mL of THF, to which was added sodium tert-butoxide (960 mg, 10 mmol) (CAS: 865-48-5, Energy, Shanghai) with stirring in an ice bath. After further stirring for 20 min, the reaction solution was stirred in an oil bath at 40° C. until complete reaction with TLC tracking. Then, the system was cooled to room temperature, to which were added saturated ammonium chloride solution and ethyl acetate for extraction. The resulting organic phase was washed once with water and saturated sodium chloride, dried with anhydrous sodium sulfate, filtered, concentrated, and then subjected to silica gel column chromatography (dichoromethane/methanol) to obtain intermediate int-1 (106 mg, 0.326 mmol).

The intermediate int-1 (35.4 mg, 0.11 mmol) and 2,6-dichorobenzyl chloride (22.5 mg, 0.12 mmol) as raw material B (Appendix 1) were dissolved in acetonitrile. After sealing, the reaction solution was stirred in an oil bath at 70° C. for 12 h. The system was cooled to room temperature, concentrated, and then subjected gel to silica column chromatography (dichoromethane/methanol) to obtain compound IA-1 (21.6 mg).

2. Compounds IA-2~IA-3 could be Synthesized by a Similar Method.

Please see the corresponding raw materials in Appendix 1. Synthetic Scheme II of Compound I is:

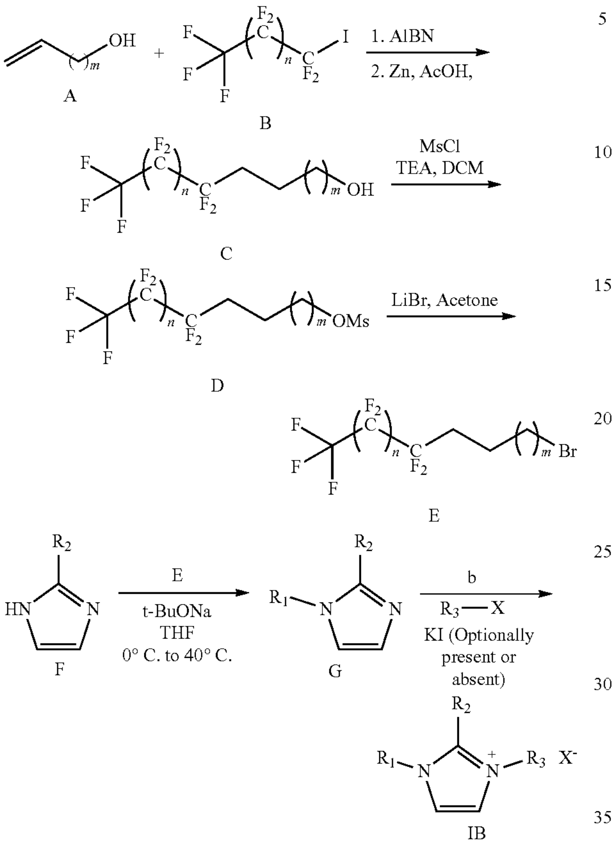

The compound A (1 eq), the compound B (1.2 eq) and AIBN (0.1 eq) were put in a microwave tube. The microwave tube was sealed, and purged with nitrogen three times, followed by reaction in an oil bath at 60° C. or 100° C. for 24 h. The reaction system was cooled to room temperature, to which were added glacial acetic acid and zinc powder (20 eq). After stirring at room temperature for 12 h, the reaction was stopped. The system was filtered, and concentrated, to which was added a proper amount of water. Then, the pH was adjusted to be neutral by using a 2N sodium hydroxide solution, and petroleum ether was added for extraction of aqueous phase. The resulting organic phase was concentrated to obtain compound C.

The compound C (1 eq) and triethylamine (3 eq) were dissolved in dichoromethane. The resulting solution was stirred in an ice bath, to which was added slowly dropwise methylsulfonyl chloride (2 eq). After completion of the addition, the solution was further stirred in an ice bath for 10 min, and then reacted at room temperature for 10 h. After quenching by adding water, the solution was extracted with dichoromethane/water. The resulting organic phase was washed once with water and saturated sodium chloride in sequence, dried with anhydrous sodium sulfate, concentrated, and then subjected to silica gel column chromatography (petroleum ether/ethyl acetate) to obtain compound D.

The compound D (1 eq) and lithium bromide (3 eq) were dissolved in acetone. The system was reacted under reflux at 60° C. for 12 h, filtered, concentrated, and subjected to silica gel column chromatography (eluted with petroleum ether) to obtain compound E.

The compounds F (1 eq) and E (1.2 eq) were dissolved in THF, to which was added sodium tert-butoxide (2 eq) with stirring in an ice bath. After further stirring for 20 min, the reaction solution was stirred in an oil bath at 40° C. until complete reaction with TLC tracking. Then, the system was cooled to room temperature, to which were added saturated ammonium chloride solution and ethyl acetate for extraction. The resulting organic phase was washed once with water and saturated sodium chloride, dried with anhydrous sodium sulfate, filtered, concentrated, and then subjected to silica gel column chromatography (dichoromethane/methanol) to obtain compound G.

The compound G (1 eq) and $R_3$—X (1.2 eq) were dissolved in acetonitrile, to which was optionally added potassium iodide (6 eq). After sealing, the reaction solution was stirred in an oil bath at 70° C. for 12 h. The system was cooled to room temperature, concentrated, and then subjected to silica gel column chromatography (dichoromethane/methanol) to obtain compound IB.

The implementation of the synthetic scheme I of compound IB is described as follows.

1. Compound IB-1:

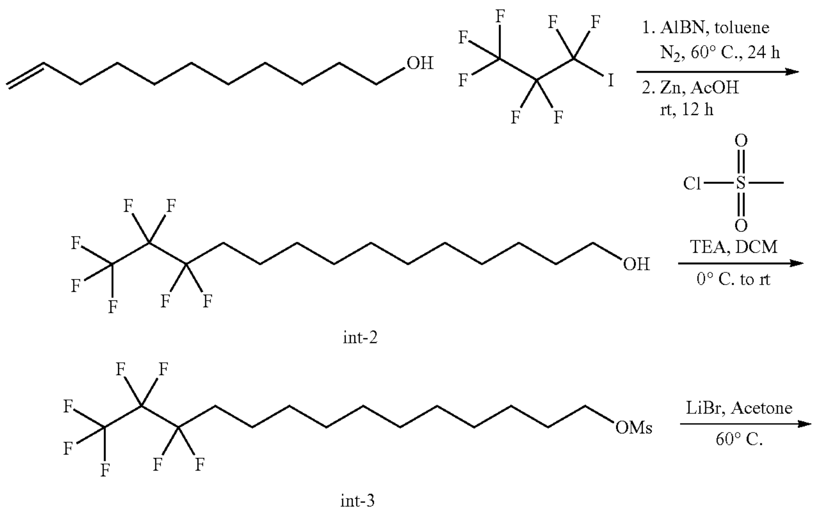

-continued

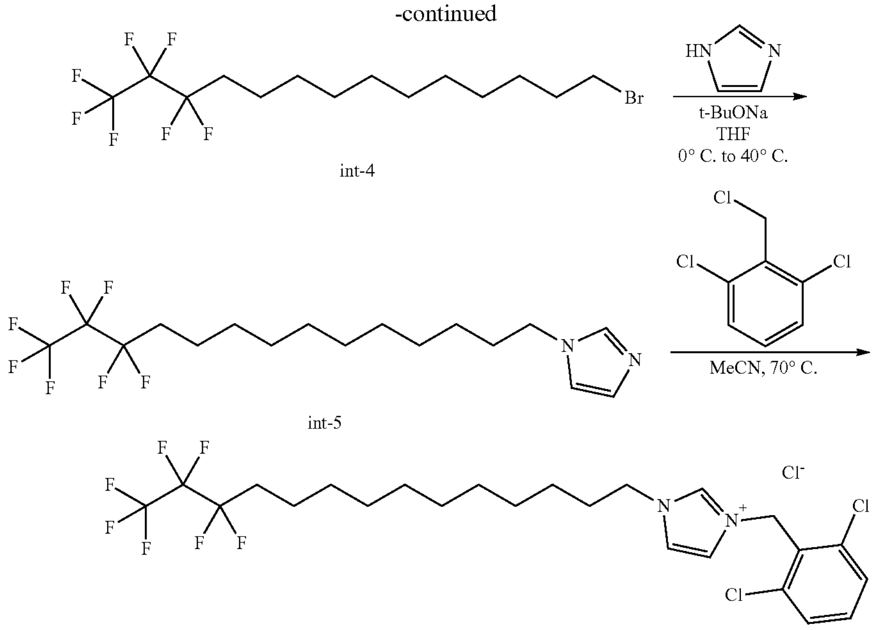

int-4 int-5

IB-1

10-Undecen-1-ol (3406 mg, 20 mmol) (CAS: 112-43-6, Aikon, Jiangsu), perfluoroiodopropane (7102 mg, 24 mmol) as raw material C (Appendix 1) and AIBN (328.4 mg, 2 mmol) (CAS: 78-67-1, Explore, Shanghai) were put in a microwave tube. The microwave tube was sealed, and purged with nitrogen three times, followed by reaction in an oil bath at 60° C. for 24 h. The reaction system was cooled to room temperature, to which were added 70 ml of glacial acetic acid and zinc powder (26 g, 400 mmol) (CAS: 7440-66-6, Greenfield, Xiamen, Fujian). After stirring at room temperature for 12 h, the reaction was stopped. The system was filtered, and concentrated, to which was added a proper amount of water. Then, the pH was adjusted to be neutral by using a 2N sodium hydroxide solution, and petroleum ether was added for extraction of aqueous phase. The resulting organic phase was concentrated to obtain intermediate int-2 (3820 mg, 11.25 mmol).

The int-2 (3820 mg, 11.25 mmol) and triethylamine (3408 mg, 33.75 mmol) (CAS: 121-44-8, Energy, Shanghai) were dissolved in 100 ml of dichoromethane. The resulting solution was stirred in an ice bath, to which was added slowly dropwise methylsulfonyl chloride (7735 mg, 67.5 mmol) (CAS: 124-63-0, Energy, Shanghai). After completion of the addition, the solution was further stirred in an ice bath for 10 min, and then reacted at room temperature for 10 h. After quenching by adding water, the solution was extracted with dichoromethane/water. The resulting organic phase was washed once with water and saturated sodium chloride in sequence, dried with anhydrous sodium sulfate, concentrated, and then subjected to silica gel column chromatography (petroleum ether/ethyl acetate) to obtain intermediate int-3 (4354 mg, 10.4 mmol).

The int-3 (4354 mg, 10.4 mmol) and lithium bromide (2709 mg, 31.2 mmol) (CAS: 7550-35-8, Energy, Shanghai) were dissolved in 50 ml of acetone. The system was reacted under reflux at 60° C. for 12 h, filtered, concentrated, and subjected to silica gel column chromatography (eluted with petroleum ether) to obtain intermediate int-4 (3715 mg, 9.2 mmol).

The int-4 (403.2 mg, 1 mmol) and imidazole (81.7 mg, 1.2 mmol) as raw material A (Appendix 1) were dissolved in 30 mL of THF, to which was added sodium tert-butoxide (192 mg, 2 mmol) with stirring in an ice bath. After further stirring for 20 min, the reaction solution was stirred in an oil bath at 40° C. until complete reaction with TLC tracking. Then, the system was cooled to room temperature, to which were added saturated ammonium chloride solution and ethyl acetate for extraction. The resulting organic phase was washed once with water and saturated sodium chloride, dried with anhydrous sodium sulfate, filtered, concentrated, and then subjected to silica gel column chromatography (dichoromethane/methanol) to obtain intermediate int-5 (295 mg, 0.75 mmol).

The int-5 (39 mg, 0.1 mmol) and 2,6-dichlorobenzyl chloride (23.4 mg, 0.12 mmol) as raw material B (Appendix 1) were dissolved in 1.5 ml of acetonitrile. After sealing, the reaction solution was stirred in an oil bath at 70° C. for 12 h. The system was cooled to room temperature, concentrated, and then subjected to silica gel column chromatography (dichoromethane/methanol) to obtain compound IB-1 (20.5 mg).

2. Compounds IB-1~IB-58 could be Synthesized by a Similar Method.

Please see the corresponding raw materials in Appendix 1.

Synthesis of Compounds IB-59 and IB-60

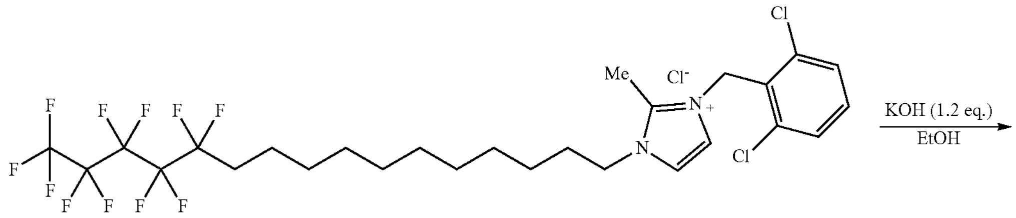

IB-33

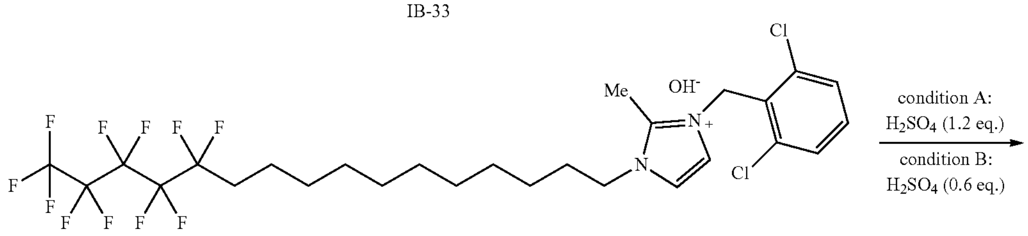

int-6

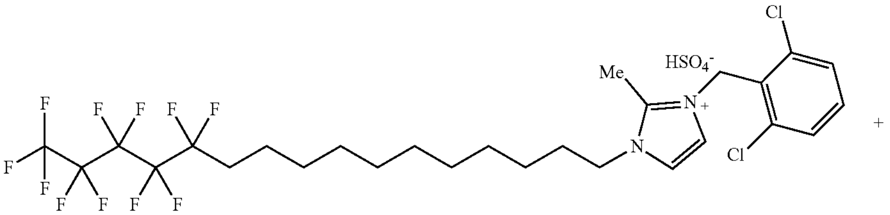

IB-59
(condition A, synthesis of compoundIB-59)

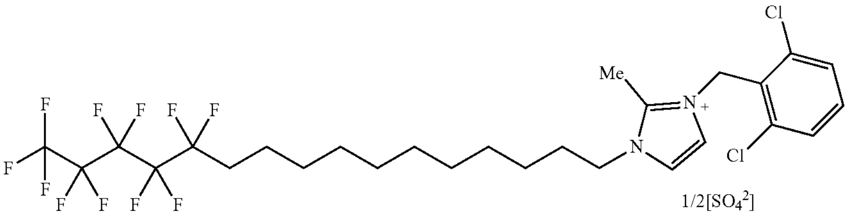

IB-60
(condition B, synthesis of compoundIB-60)

Compound IB-33 (10 g, 14.3 mmol) was dissolved in 50 ml of ethanol, cooled to 0° C., to which was added potassium hydroxide (0.96 g, 17.2 mmol). The reaction system was further stirred at 0~5° C. for 8 h. After completion of the reaction, the reaction system was filtered to give a clear filtrate.

Condition A: The filtrate was cooled to 0° C., to which was added dropwise 98% concentrated sulfuric acid (17.2 mmol, 1.2 Eq.). The reaction system was further stirred at 0~5° C. for 2 h. After completion of the reaction, the reaction system was concentrated, and recrystallized with methyl t-butyl ether to obtain compound IB-59, 6.6 g, yield 60.66%. The content of bisulfate, determined by titration, was 12.7% (theoretical value: 12.61%) therein.

Condition B: The filtrate was cooled to 0° C., to which was added dropwise 98% concentrated sulfuric acid (8.6 mmol, 0.6 Eq.). The reaction system was further stirred at 0~5° C. for 2 h. After completion of the reaction, the reaction system was concentrated, and recrystallized with methyl t-butyl ether to obtain compound IB-60, 6.2 g, yield 60.85%. The content of sulfate, determined by ion chromatography, was 6.7% (theoretical value: 6.74%) therein.

Appendix 1. Some Commercial Raw Materials Used for the Synthesis of Example Compounds

| Raw material A |
| --- |
| imidazole, CAS: 288-32-4, Macklin, Shanghai |
| 2-methylimidazole, CAS: 693-98-1, Acros Organics, Belgium |
| 2-ethylimidazole, CAS: 1072-62-4, Macklin, Shanghai |
| 2-isopropylimidazole, CAS: 36947-68-9, Bide, Shanghai |
| 2-t-butylimidazole, CAS: 36947-69-0, Accela ChemBio, Shanghai |
| 2-cyclopropyl-1H-imidazole, CAS: 89532-38-7, HWRK, Beijing |
| Raw material B |
| 2-chloro-6-fluorobenzyl bromide, CAS: 68220-26-8, Bide, Shanghai |
| 2-chloro-6-fluorobenzyl chloride, CAS: 55117-15-2, Energy, Shanghai |
| 2,6-dichlorobenzyl bromide, CAS: 20443-98-5, Energy, Shanghai |
| 2,6-dichlorobenzyl chloride, CAS: 2014-83-7, Energy, Shanghai |
| 5-fluoro-2-methoxybenzyl bromide, CAS: 20-3-560364, Energy, Shanghai |
| Raw material C |
| perfluoroiodopropane, CAS: 754-34-7, Aikon, Jiangsu |
| perfluoroiodobutane, CAS: 423-39-2, Aikon, Jiangsu |
| perfluoroiodopentane, CAS: 638-79-9, Aikon, Jiangsu |
| perfluoroiodohexane, CAS: 355-43-1, Energy, Shanghai |

TABLE 1

Structure and characterization of compounds IA-IB

| No. | Structure | $^1$H NMR and/or MS data |
| --- | --- | --- |
| IA-1 | 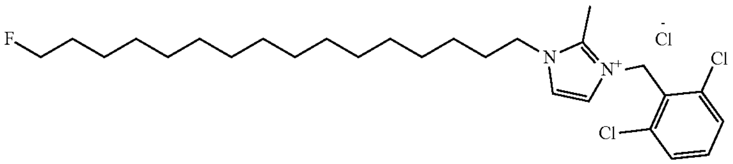 [SMILES: Cc1n(CCCCCCCCCCCCCCCCF)cc[n+]1Cc1c(Cl)cccc1Cl ; Cl] | $^1$H NMR (400 MHz, Methanol-$d_4$) δ 7.66-7.58 (m, 3H), 7.55 (dd, J = 9.2, 6.8 Hz, 1H), 7.17 (d, J = 2.3 Hz, 1H), 5.70 (s, 2H), 4.25 (t, J = 7.3 Hz, 2H), 3.58 (t, J = 6.6 Hz, 2H), 2.86 (s, 3H), 1.95-1.79 (m, 2H), 1.62-1.50 (m, 2H), 1.40-1.27 (m, 24H). MS (ESI) m/z: 483 $[M—Cl]^+$. |
| IA-2 | 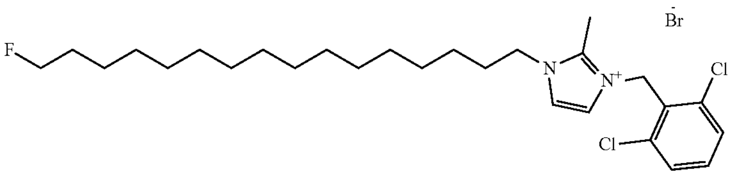 [SMILES: Cc1n(CCCCCCCCCCCCCCCCF)cc[n+]1Cc1c(Cl)cccc1Cl ; Br] | $^1$H NMR (400 MHz, Methanol-$d_4$) δ 7.66-7.60 (m, 3H), 7.56 (dd, J = 9.2, 6.7 Hz, 1H), 7.17 (d, J = 2.2 Hz, 1H), 5.71 (s, 2H), 4.27 (t, J = 7.3 Hz, 2H), 3.59 (t, J = 6.7 Hz, 2H), 2.88 (s, 3H), 1.95-1.83 (m, 2H), 1.64-1.51 (m, 2H), 1.44-1.32 (m, 24H). MS (ESI) m/z: 483 $[M—Br]^+$. |
| IA-3 | 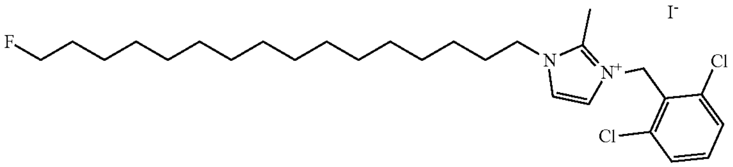 [SMILES: Cc1n(CCCCCCCCCCCCCCCCF)cc[n+]1Cc1c(Cl)cccc1Cl ; [I-]] | $^1$H NMR (400 MHz, Methanol-$d_4$) δ 7.64-7.60 (m, 3H), 7.58-7.53 (m, 1H), 7.17 (d, J = 2.2 Hz, 1H), 5.70 (s, 2H), 4.26 (t, J = 7.3 Hz, 2H), 3.58 (t, J = 6.6 Hz, 2H), 2.87 (s, 3H), 1.97-1.81 (m, 2H), 1.62-1.51 (m, 2H), 1.42-1.29 (m, 24H). MS (ESI) m/z: 483 $[M—I]^+$. |
| IB-1 | 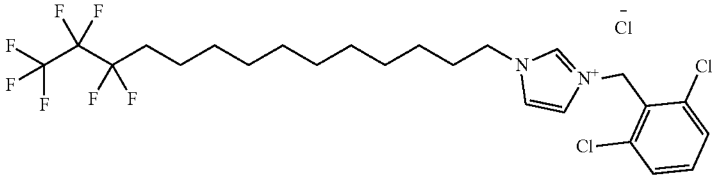 [SMILES: FC(F)(F)C(F)(F)C(F)(F)CCCCCCCCCCCn1cc[n+](Cc2c(Cl)cccc2Cl)c1 ; [Cl-]] | $^1$H NMR (600 MHz, Methanol-$d_4$) δ 9.20 (d, J = 1.7 Hz, 1H), 7.71 (t, J = 1.9 Hz, 1H), 7.60 (t, J = 1.9 Hz, 1H), 7.57 (d, J = 1.0 Hz, 1H), 7.56 (s, 1H), 7.51-7.47 (m, 1H), 5.76 (s, 2H), 4.24 (t, J = 7.2 Hz, 2H), 2.19-2.04 (m, 2H), 1.91-1.83 (m, 2H), 1.62-1.51 (m, 2H), 1.43-1.36 (m, 2H), 1.35-1.28 (m, 12H). MS (ESI) m/z: 549 $[M—Cl]^+$. |
| IB-2 | 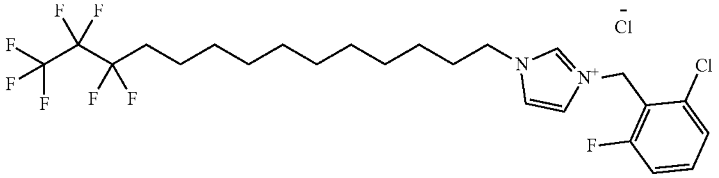 | $^1$H NMR (600 MHz, Methanol-$d_4$) δ 9.20 (s, 1H), 7.70-7.69 (m, 1H), 7.60-7.59 (m, 1H), 7.54-7.49 (m, 1H), 7.40 (d, J = 8.3 Hz, 1H), 7.30-7.25 (m, 1H), 5.64 (d, J = 1.7 Hz, 2H), 4.23 (t, J = 7.3 Hz, 2H), 2.15-2.05 (m, 2H), 1.90-1.83 (m, 2H), 1.74-1.66 (m, 2H), 1.60-1.54 (s, 2H), 1.33-1.27 (m, 12H). MS (ESI) m/z: 533 $[M—Cl]^+$ |
| IB-3 | 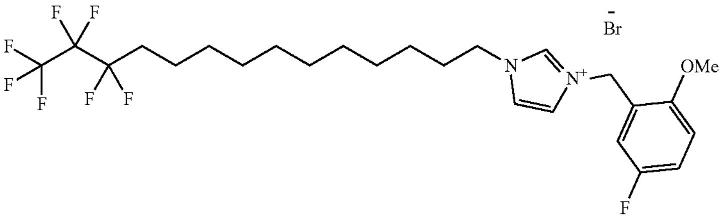 [SMILES: COc1ccc(F)cc1C[n+]1ccn(CCCCCCCCCCCC(F)(F)C(F)(F)C(F)(F)F)c1 ; [Br-]] | $^1$H NMR (600 MHz, Methanol-$d_4$) δ 9.14 (s, 1H), 7.64 (t, J = 1.8 Hz, 1H), 7.62 (t, J = 1.9 Hz, 1H), 7.29 (dd, J = 8.4, 3.1 Hz, 1H), 7.19-7.12 (m, 1H), 7.06 (dd, J = 9.1, 4.3 Hz, 1H), 5.39 (s, 2H), 4.24 (t, J = 7.3 Hz, 2H), 3.86 (s, 3H), 2.19-2.05 (m, 2H), 1.92-1.81 (m, 2H), 1.62-1.53 (m, 2H), 1.43-1.38 (m, 2H), 1.36-1.27 (m, 12H). MS (ESI) m/z: 529 $[M—Br]^+$. |
| IB-4 | 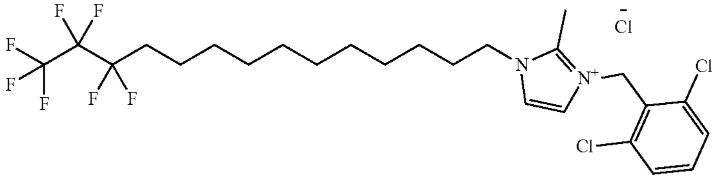 [SMILES: Cc1n(CCCCCCCCCCCC(F)(F)C(F)(F)C(F)(F)F)cc[n+]1Cc1c(Cl)cccc1Cl ; [Cl-]] | $^1$H NMR (600 MHz, Methanol-$d_4$) δ 7.59-7.57 (m, 2H), 7.57 (s, 1H), 7.51 (dd, J = 8.9, 7.3 Hz, 1H), 7.13 (d, J = 2.2 Hz, 1H), 5.65 (s, 2H), 4.22 (t, J = 7.4 Hz, 2H), 2.82 (s, 3H), 2.17-2.05 (m, 2H), 1.90-1.78 (m, 2H), 1.65-1.53 (m, 2H), 1.42-1.29 (m, 14H). MS (ESI) m/z: 563 $[M—Cl]^+$ |
| IB-5 | 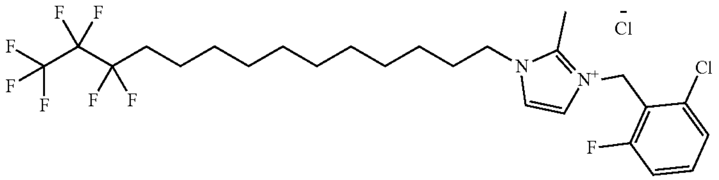 [SMILES: Cc1n(CCCCCCCCCCCC(F)(F)C(F)(F)C(F)(F)F)cc[n+]1Cc1c(F)cccc1Cl ; [Cl-]] | $^1$H NMR (600 MHz, Methanol-$d_4$) δ 7.58 (d, J = 2.2 Hz, 1H), 7.55-7.50 (m, 1H), 7.42 (d, J = 8.2 Hz, 1H), 7.35 (d, J = 1.9 Hz, 1H), 7.28-7.23 (m, 1H), 5.57 (d, J = 1.2 Hz, 2H), 4.21-4.15 (m, 2H), 2.77 (s, 3H), 2.18-2.03 (m, 2H), 1.85-1.77 (m, 2H), 1.62-1.52 (m, 2H), 1.43-1.38 (m, 2H), 1.37-1.29 (m, 12H). |

TABLE 1-continued

Structure and characterization of compounds IA-IB

| No. | Structure | $^1$H NMR and/or MS data |
|---|---|---|
| | | MS (ESI) m/z: 547 [M—Cl]$^+$. |
| IB-6 | 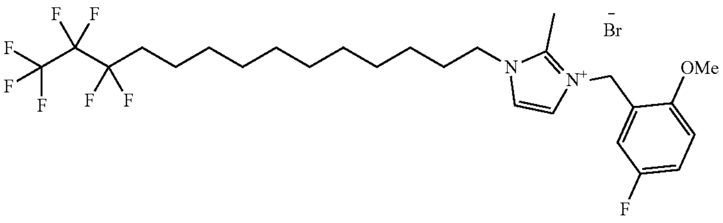 [SMILES: COc1ccc(F)cc1C[n+]1ccn(CCCCCCCCCCCC(F)(F)C(F)(F)C(F)(F)F)c1C ; [Br-]] | $^1$H NMR (600 MHz, Methanol-d$_4$) δ 7.56 (d, J = 2.2 Hz, 1H), 7.46 (d, J = 2.2 Hz, 1H), 7.20-7.13 (m, 2H), 7.07 (dd, J = 9.0, 4.3 Hz, 1H), 5.33 (s, 2H), 4.21-4.16 (m, 2H), 3.85 (s, 3H), 2.73 (s, 3H), 2.19-2.06 (m, 2H), 1.88-1.80 (m, 2H), 1.63-1.56 (m, 2H), 1.44-1.38 (m, 2H), 1.38-1.30 (m, 12H).<br>MS (ESI) m/z: 543 [M—Br]$^+$. |
| IB-7 | 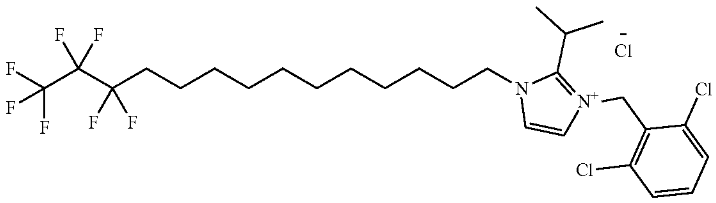 [SMILES: CC(C)c1n(CCCCCCCCCCCC(F)(F)C(F)(F)C(F)(F)F)cc[n+]1Cc1c(Cl)cccc1Cl ; [Cl-]] | $^1$H NMR (600 MHz, Methanol-d$_4$) δ 7.60 (d, 1.2 Hz, 1H), 7.59 (s, 1H), 7.57 (d, J = 2.2 Hz, 1H), 7.53 (dd, J = 8.9, 7.2 Hz, 1H), 6.98 (d, J = 2.2 Hz, 1H), 5.73 (s, 2H), 4.28-4.26 (m, 2H), 3.91-3.87 (m, 1H), 2.18-2.06 (m, 2H), 1.91-1.84 (m, 2H), 1.61-1.55 (m, 8H), 1.41-1.36 (m, 6H), 1.36-1.30 (m, 8H).<br>MS (ESI) m/z: 591 [M—Cl]$^+$. |
| IB-8 | 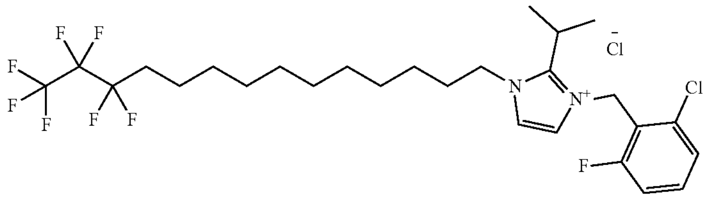 [SMILES: CC(C)c1n(CCCCCCCCCCCC(F)(F)C(F)(F)C(F)(F)F)cc[n+]1Cc1c(F)cccc1Cl ; [Cl-]] | $^1$H NMR (600 MHz, Methanol-d$_4$) δ 7.57 (d, J = 2.2 Hz, 1H), 7.56-7.53 (m, 1H), 7.45 (d, J = 8.2 Hz, 1H), 7.30-7.26 (m, 1H), 7.20 (d, J = 2.2 Hz, 1H), 5.65 (s, 2H), 4.27-4.23 (m, 2H), 3.85 (p, J = 7.3 Hz, 1H), 2.17-2.06 (m, 2H), 1.90-1.83 (m, 2H), 1.61-1.55 (m, 2H), 1.52 (d, J = 7.3 Hz, 6H), 1.41-1.36 (m, 6H), 1.35-1.29 (m, 8H).<br>MS (ESI) m/z: 575 [M—Cl]$^+$. |
| IB-9 | 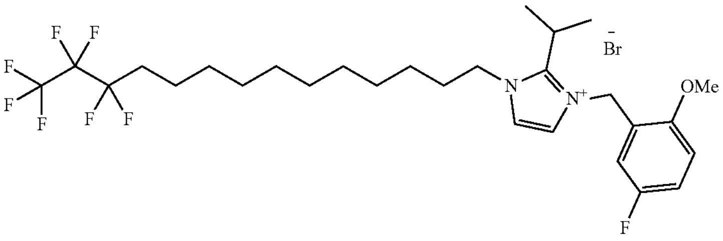 [SMILES: COc1ccc(F)cc1C[n+]1ccn(CCCCCCCCCCCC(F)(F)C(F)(F)C(F)(F)F)c1C(C)C ; [Br-]] | $^1$H NMR (600 MHz, Methanol-d$_4$) δ 7.60 (d, J = 2.2 Hz, 1H), 7.39 (d, J = 2.2 Hz, 1H), 7.22-7.16 (m, 1H), 7.11 (dt, J = 9.1, 3.3 Hz, 2H), 5.45 (s, 2H), 4.30-4.25 (m, 2H), 3.86 (s, 3H), 3.85-3.80 (m, 1H), 2.22-2.08 (m, 2H), 1.93-1.86 (m, 2H), 1.64-1.56 (m, 2H), 1.48 (d, J = 7.3 Hz, 6H), 1.44-1.39 (m, 6H), 1.39-1.33 (m, 8H).<br>MS (ESI) m/z: 571 [M—Br]$^+$. |
| IB-10 | 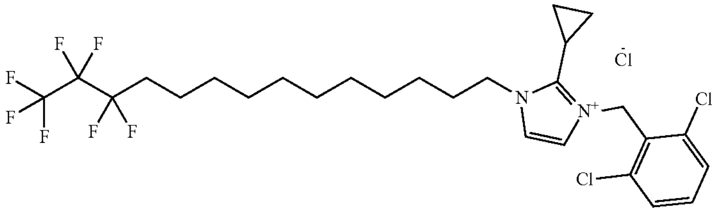 [SMILES: FC(F)(F)C(F)(F)C(F)(F)CCCCCCCCCCCn1cc[n+](Cc2c(Cl)cccc2Cl)c1C1CC1 ; Cl] | $^1$H NMR (600 MHz, Methanol-d$_4$) δ 7.58 (d, J = 0.9 Hz, 1H), 7.57 (s, 1H), 7.56 (d, J = 2.3 Hz, 1H), 7.50 (dd, J = 8.9, 7.3 Hz, 1H), 7.05 (d, J = 2.2 Hz, 1H), 5.79 (s, 2H), 4.33 (t, J = 7.4 Hz, 2H), 2.18-2.05 (m, 3H), 1.94-1.87 (m, 2H), 1.62-1.55 (m, 2H), 1.48-1.44 (m, 2H), 1.42-1.29 (m, 14H), 1.25-1.21 (m, 2H).<br>MS (ESI) m/z: 589 [M—Cl]$^+$. |
| IB-11 | 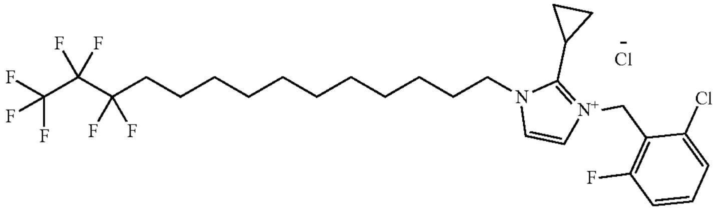 [SMILES: Fc1cccc(Cl)c1C[n+]1ccn(CCCCCCCCCCCC(F)(F)C(F)(F)C(F)(F)F)c1C1CC1 ; [Cl-]] | $^1$H NMR (600 MHz, Methanol-d$_4$) δ 7.58 (d, J = 2.2 Hz, 1H), 7.57-7.51 (m, 1H), 7.43 (d, J = 8.2 Hz, 1H), 7.31-7.26 (m, 1H), 7.25 (d, J = 2.2 Hz, 1H), 5.70 (s, 2H), 4.34-4.29 (m, 2H), 2.18-2.07 (m, 2H), 2.07-2.02 (m, 1H), 1.93-1.87 (m, 2H), 1.63-1.55 (m, 2H), 1.48-1.43 (m, 2H), 1.43-1.31 (m, 14H), 1.23-1.19 (m, 2H).<br>MS (ESI) m/z: 573 [M—Cl]$^+$. |

TABLE 1-continued

Structure and characterization of compounds IA-IB

| No. | Structure | $^1$H NMR and/or MS data |
| --- | --- | --- |
| IB-12 | 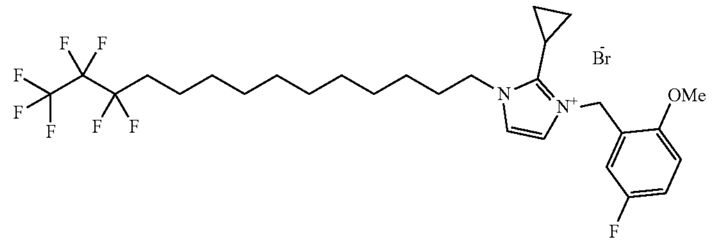 [SMILES: COc1ccc(F)cc1C[n+]1ccn(CCCCCCCCCCCC(F)(F)C(F)(F)C(F)(F)F)c1C1CC1 ; Br] | $^1$H NMR (600 MHz, Methanol-$d_4$) δ 7.56 (d, J = 2.2 Hz, 1H), 7.37 (d, J = 2.2 Hz, 1H), 7.19-7.12 (m, 2H), 7.08 (dd, J = 8.9, 4.3 Hz, 1H), 5.46 (s, 2H), 4.31 (t, J = 7.4 Hz, 2H), 3.84 (s, 3H), 2.19-2.08 (m, 2H), 2.01-1.95 (m, 1H), 1.94-1.87 (m, 2H), 1.64-1.56 (m, 2H), 1.44-1.31 (m, 16H), 1.19-1.14 (m, 2H). MS (ESI) m/z: 569 [M—Br]$^+$. |
| IB-13 | 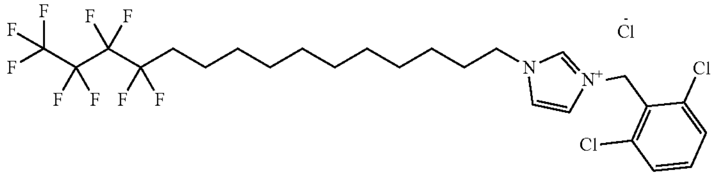 [SMILES: FC(F)(F)C(F)(F)C(F)(F)C(F)(F)CCCCCCCCCCCn1cc[n+](Cc2c(Cl)cccc2Cl)c1 ; Cl] | $^1$H NMR (600 MHz, Methanol-$d_4$) δ 9.23 (s, 1H), 7.74 (s, 1H), 7.62 (s, 1H), 7.59 (d, J = 8.0 Hz, 2H), 7.52 (dd, J = 8.8, 7.3 Hz, 1H), 5.79 (s, 2H), 4.27 (t, J = 7.1 Hz, 2H), 2.16 (tt, J = 18.7, 7.9 Hz, 2H), 1.90 (t, J = 7.3 Hz, 2H), 1.61 (p, J = 7.6 Hz, 2H), 1.37-1.29 (m, 14H). MS (ESI) m/z: 599 [M—Cl]$^+$. |
| IB-14 | 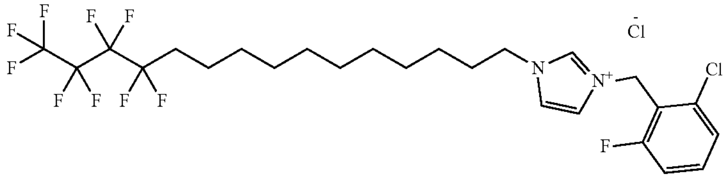 [SMILES: Fc1cccc(Cl)c1C[n+]1ccn(CCCCCCCCCCCC(F)(F)C(F)(F)C(F)(F)C(F)(F)F)c1 ; Cl] | $^1$H NMR (600 MHz, Methanol-$d_4$) δ 9.25 (s, 1H), 7.73 (d, J = 1.8 Hz, 1H), 7.63 (d, J = 1.8 Hz, 1H), 7.55 (td, J = 8.3, 6.1 Hz, 1H), 7.45-7.41 (m, 1H), 7.30 (ddd, J = 9.5, 8.4, 1.1 Hz, 1H), 5.68 (d, J = 1.7 Hz, 2H), 4.26 (t, J = 7.2 Hz, 2H), 2.22-2.09 (m, 2H), 1.90 (p, J = 7.4 Hz, 2H), 1.65-1.56 (m, 2H), 1.37-1.31 (m, 14H). MS (ESI) m/z: 583 [M—Cl]$^+$. |
| IB-15 | 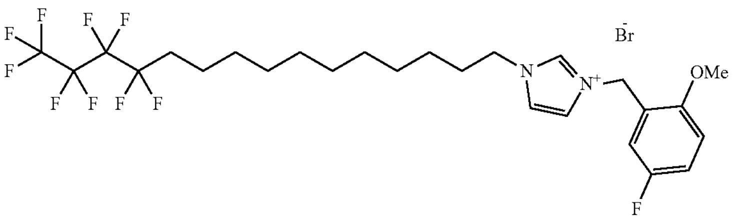 [SMILES: COc1ccc(F)cc1C[n+]1ccn(CCCCCCCCCCCC(F)(F)C(F)(F)C(F)(F)C(F)(F)F)c1 ; Br] | $^1$H NMR (600 MHz, Methanol-$d_4$) δ 9.17 (d, J = 1.7 Hz, 1H), 7.66 (t, J = 1.8 Hz, 1H), 7.64 (t, J = 1.9 Hz, 1H), 7.31 (dd, J = 8.4, 3.1 Hz, 1H), 7.18 (ddd, J = 9.1, 8.1, 3.1 Hz, 1H), 7.08 (dd, J = 9.1, 4.3 Hz, 1H), 5.41 (s, 2H), 4.26 (t, J = 7.2 Hz, 2H), 3.89 (s, 3H), 2.22-2.09 (m, 2H), 1.90 (p, J = 7.4 Hz, 2H), 1.65-1.57 (m, 2H), 1.40-1.29 (m, 14H). MS (ESI) m/z: 579 [M—Br]$^+$. |
| IB-16 | 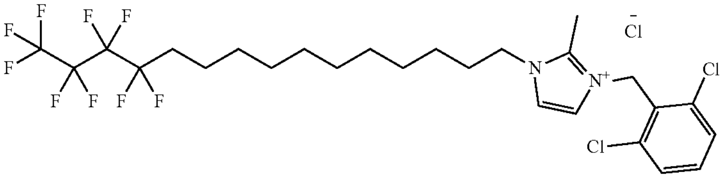 | $^1$H NMR (600 MHz, Methanol-$d_4$) δ 7.62-7.59 (m, 2H), 7.59 (d, J = 2.3 Hz, 1H), 7.53 (dd, J = 8.9, 7.3 Hz, 1H), 7.15 (d, J = 2.2 Hz, 1H), 5.67 (s, 2H), 4.23 (t, J = 7.3 Hz, 2H), 2.84 (s, 3H), 2.22-2.09 (m, 2H), 1.86 (p, J = 7.3 Hz, 2H), 1.68-1.57 (m, 2H), 1.39-1.34 (m, 14H). MS (ESI) m/z: 613 [M—Cl]$^+$. |
| IB-17 | 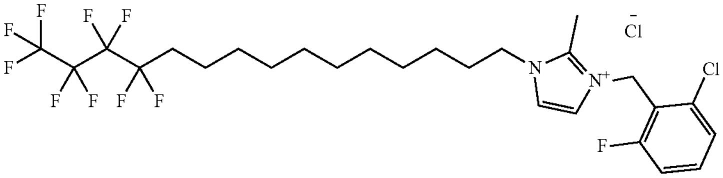 | $^1$H NMR (600 MHz, Methanol-$d_4$) δ 7.60 (d, J = 2.2 Hz, 1H), 7.55 (td, J = 8.3, 6.1 Hz, 1H), 7.45 (dt, J = 8.3, 1.1 Hz, 1H), 7.38 (d, J = 2.2 Hz, 1H), 7.30 (ddd, J = 9.7, 8.3, 1.1 Hz, 1H), 5.59 (d, J = 1.4 Hz, 2H), 4.21 (t, J = 7.4 Hz, 2H), 2.79 (s, 3H), 2.22-2.02 (m, 2H), 1.85 (p, J = 7.4 Hz, 2H), 1.68-1.55 (m, 2H), 1.44-1.30 (m, 14H). MS (ESI) m/z: 597 [M—Cl]$^+$. |
| IB-18 | 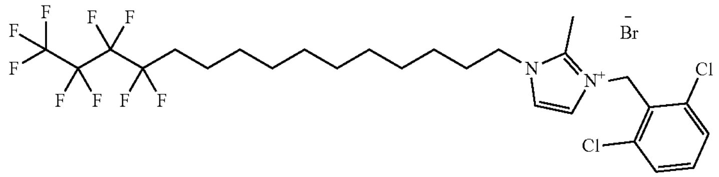 | $^1$H NMR (400 MHz, Methanol-$d_4$) δ 7.66-7.59 (m, 3H), 7.55 (dd, J = 9.2, 6.8 Hz, 1H), 7.17 (d, J = 2.2 Hz, 1H), 5.70 (s, 2H), 4.27 (t, J = 7.3 Hz, 2H), 2.87 (s, 3H), 2.27-2.02 (m, 2H), 1.89 (p, J = 7.2 Hz, 2H), 1.71-1.55 (m, 2H), 1.49-1.31 (m, 14H). MS (ESI) m/z: 613 [M—Br]$^+$. |

TABLE 1-continued

Structure and characterization of compounds IA-IB

| No. | Structure | $^1$H NMR and/or MS data |
|---|---|---|
| IB-19 | 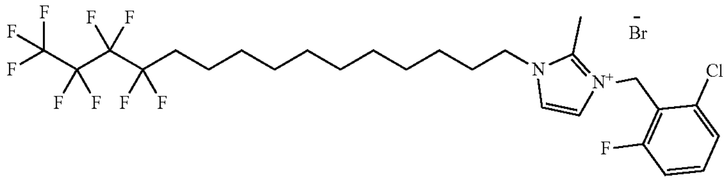 [SMILES: Cc1n(CCCCCCCCCCCC(F)(F)C(F)(F)C(F)(F)C(F)(F)F)cc[n+]1Cc1c(F)cccc1Cl ; [Br-]] | $^1$H NMR (600 MHz, Methanol-$d_4$) δ 7.62 (d, J = 2.3 Hz, 1H), 7.56 (td, J = 8.3, 6.1 Hz, 1H), 7.45 (dt, J = 8.3, 1.1 Hz, 1H), 7.39 (d, J = 2.2 Hz, 1H), 7.30 (ddd, J = 9.6, 8.4, 1.1 Hz, 1H), 5.61 (d, J = 1.4 Hz, 2H), 4.22 (t, J = 7.4 Hz, 2H), 2.81 (s, 3H), 2.24-2.09 (m, 2H), 1.92-1.80 (m, 2H), 1.62 (p, J = 7.6 Hz, 2H), 1.42-1.30 (m, 14H). MS (ESI) m/z: 597 [M—Br]$^+$. |
| IB-20 | 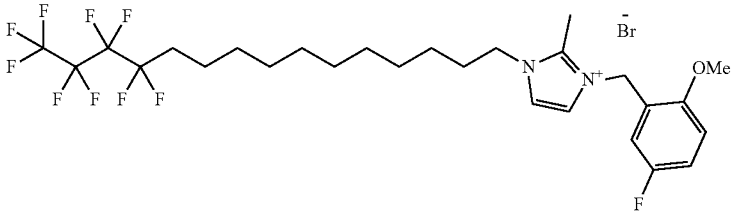 [SMILES: COc1ccc(F)cc1C[n+]1ccn(CCCCCCCCCCCC(F)(F)C(F)(F)C(F)(F)C(F)(F)F)c1C ; [Br-]] | $^1$H NMR (600 MHz, Methanol-$d_4$) δ 7.57 (d, J = 2.2 Hz, 1H), 7.47 (d, J = 2.2 Hz, 1H), 7.21-7.14 (m, 2H), 7.08 (dd, J = 8.8, 4.3 Hz, 1H), 5.35 (s, 2H), 4.19 (t, J = 7.4 Hz, 2H), 3.86 (s, 3H), 2.74 (s, 3H), 2.22-2.02 (m, 2H), 1.89-1.77 (m, 2H), 1.66-1.56 (m, 2H), 1.43-1.29 (m, 14H). MS (ESI) m/z: 593 [M—Br]$^+$. |
| IB-21 | 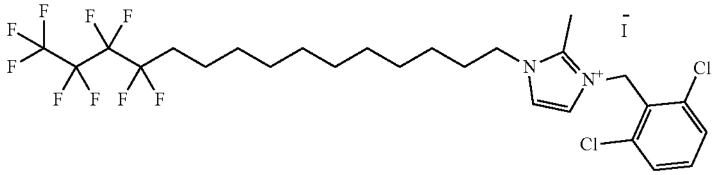 [SMILES: Cc1n(CCCCCCCCCCCC(F)(F)C(F)(F)C(F)(F)C(F)(F)F)cc[n+]1Cc1c(Cl)cccc1Cl ; [I-]] | MS (ESI) m/z: 613 [M—I]$^+$. |
| IB-22 | 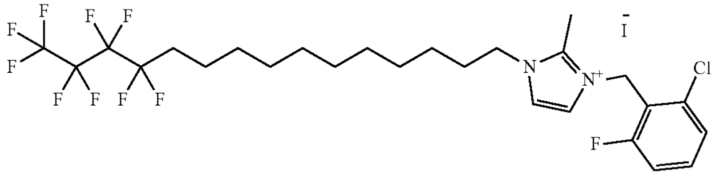 [SMILES: Cc1n(CCCCCCCCCCCC(F)(F)C(F)(F)C(F)(F)C(F)(F)F)cc[n+]1Cc1c(F)cccc1Cl ; [I-]] | $^1$H NMR (600 MHz, Methanol-$d_4$) δ 7.67 (d, J = 2.1 Hz, 1H), 7.60 (td, J = 8.1, 5.9 Hz, 1H), 7.49 (d, J = 8.2 Hz, 1H), 7.43 (d, J = 2.1 Hz, 1H), 7.34 (t, J = 9.0 Hz, 1H), 5.65 (s, 2H), 4.27 (t, J = 7.4 Hz, 2H), 2.87 (s, 3H), 2.28-2.08 (m, 2H), 1.95-1.86 (m, 2H), 1.71-1.61 (m, 2H), 1.47-1.34 (m, 14H). MS (ESI) m/z: 597 [M—I]$^+$. |
| IB-23 | 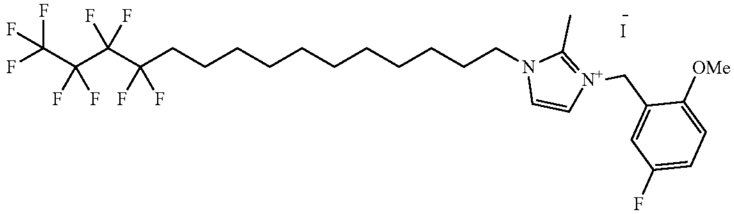 [SMILES: COc1ccc(F)cc1C[n+]1ccn(CCCCCCCCCCCC(F)(F)C(F)(F)C(F)(F)C(F)(F)F)c1C ; [I-]] | $^1$H NMR (600 MHz, Methanol-$d_4$) δ 7.57 (d, J = 2.0 Hz, 1H), 7.47 (d, J = 2.1 Hz, 1H), 7.23-7.14 (m, 2H), 7.08 (dd, J = 9.0, 4.3 Hz, 1H), 5.35 (s, 2H), 4.20 (t, J = 7.4 Hz, 2H), 3.87 (s, 3H), 2.76 (s, 3H), 2.24-2.01 (m, 2H), 1.90-1.78 (m, 2H), 1.66-1.52 (m, 2H), 1.41-1.29 (m, 14H). MS (ESI) m/z: 593 [M—I]$^+$. |
| IB-24 | 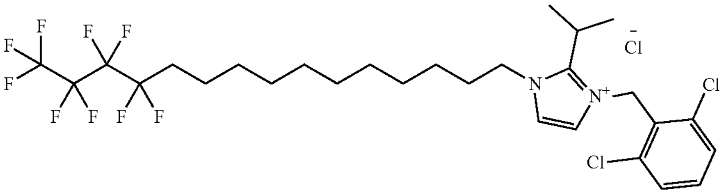 | $^1$H NMR (600 MHz, Methanol-$d_4$) δ 7.65-7.60 (m, 2H), 7.59 (d, J = 2.3 Hz, 1H), 7.56 (dd, J = 8.9, 7.2 Hz, 1H), 7.01 (d, J = 2.3 Hz, 1H), 5.76 (s, 2H), 4.30 (dd, J = 8.3, 6.8 Hz, 2H), 3.92 (p, J = 7.3 Hz, 1H), 2.22-2.08 (m, 2H), 1.94-1.85 (m, 2H), 1.61 (d, J = 7.3 Hz, 8H), 1.49-1.26 (m, 14H). MS (ESI) m/z: 641 [M—Cl]$^+$. |
| IB-25 | 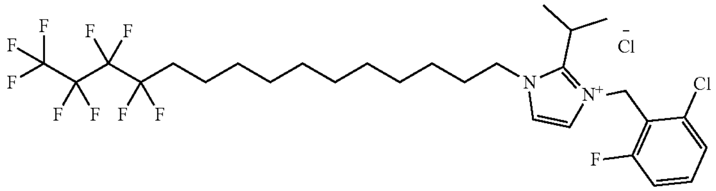 | $^1$H NMR (600 MHz, Methanol-$d_4$) δ 7.60 (d, J = 2.4 Hz, 1H), 7.59-7.55 (m, 1H), 7.49-7.45 (m, 1H), 7.31 (ddd, J = 9.6, 8.3, 1.0 Hz, 1H), 7.23 (d, J = 2.2 Hz, 1H), 5.68 (d, J = 1.3 Hz, 2H), 4.31-4.24 (m, 2H), 3.88 (p, J = 7.3 Hz, 1H), 2.23-2.08 (m, 2H), 1.94-1.85 (m, 2H), 1.66-1.58 (m, 2H), 1.55 (d, J = 7.2 Hz, 6H), 1.43-1.33 (m, 14H). MS (ESI) m/z: 625 [M—Cl]$^+$. |

TABLE 1-continued

Structure and characterization of compounds IA-IB

| No. | Structure | $^1$H NMR and/or MS data |
|---|---|---|
| IB-26 | 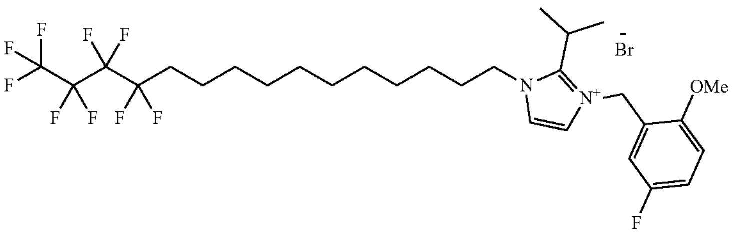 [SMILES: COc1ccc(F)cc1C[n+]1ccn(CCCCCCCCCCCC(F)(F)C(F)(F)C(F)(F)C(F)(F)F)c1C(C)C ; [Br-]] | $^1$H NMR (600 MHz, Methanol-$d_4$) δ 7.60 (d, J = 2.3 Hz, 1H), 7.39 (d, J = 2.3 Hz, 1H), 7.19 (td, J = 8.6, 3.1 Hz, 1H), 7.11 (dt, J = 8.6, 3.8 Hz, 2H), 5.45 (s, 2H), 4.28 (t, J = 7.6 Hz, 2H), 3.86 (s, 3H), 3.85-3.79 (m, 1H), 2.23-2.09 (m, 2H), 1.95-1.83 (m, 2H), 1.67-1.57 (m, 2H), 1.48 (d, J = 7.3 Hz, 6H), 1.43-1.35 (m, 14H).<br>MS (ESI) m/z: 621 [M—Br]$^+$. |
| IB-27 | 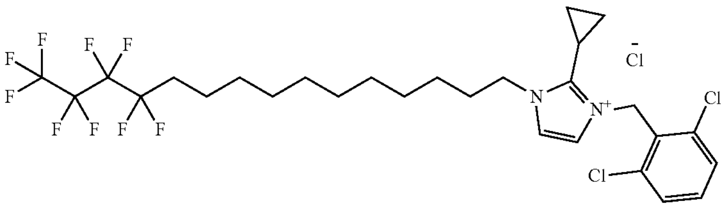 [SMILES: FC(F)(F)C(F)(F)C(F)(F)C(F)(F)CCCCCCCCCCCn1cc[n+](Cc2c(Cl)cccc2Cl)c1C1CC1 ; [Cl-]] | $^1$H NMR (600 MHz, Methanol-$d_4$) δ 7.62-7.59 (m, 3H), 7.53 (dd, J = 8.9, 7.3 Hz, 1H), 7.07 (d, J = 2.2 Hz, 1H), 5.81 (s, 2H), 4.35 (t, J = 7.4 Hz, 2H), 2.23-2.08 (m, 3H), 1.98-1.89 (m, 2H), 1.67-1.57 (m, 2H), 1.54-1.46 (m, 2H), 1.46-1.29 (m, 14H), 1.27-1.21 (m, 2H).<br>MS (ESI) m/z: 639 [M—Cl]$^+$. |
| IB-28 | 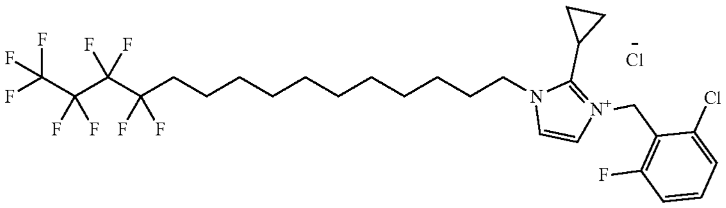 | $^1$H NMR (600 MHz, Methanol-$d_4$) δ 7.60 (d, J = 2.3 Hz, 1H), 7.56 (td, J = 8.3, 6.1 Hz, 1H), 7.45 (d, J = 8.2 Hz, 1H), 7.31 (t, J = 9.0 Hz, 1H), 7.26 (d, J = 2.3 Hz, 1H), 5.72 (s, 2H), 4.34 (t, J = 7.4 Hz, 2H), 2.22-2.10 (m, 2H), 2.10-2.02 (m, 1H), 1.96-1.88 (m, 2H), 1.67-1.58 (m, 2H), 1.50-1.45 (m, 2H), 1.45-1.26 (m, 14H), 1.26-1.21 (m, 2H).<br>MS (ESI) m/z: 623 [M—Cl]$^+$. |
| IB-29 | 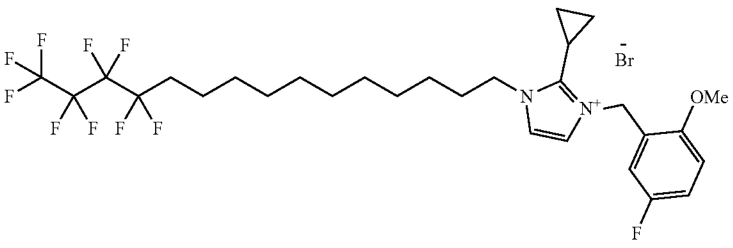 [SMILES: COc1ccc(F)cc1C[n+]1ccn(CCCCCCCCCCCC(F)(F)C(F)(F)C(F)(F)C(F)(F)F)c1C1CC1 ; [Br-]] | $^1$H NMR (600 MHz, Methanol-$d_4$) δ 7.57 (d, J = 2.2 Hz, 1H), 7.37 (d, J = 2.2 Hz, 1H), 7.20-7.14 (m, 2H), 7.09 (dd, J = 8.6, 4.2 Hz, 1H), 5.47 (s, 2H), 4.32 (t, J = 7.5 Hz, 2H), 3.85 (s, 3H), 2.22-2.10 (m, 2H), 2.03-1.96 (m, 1H), 1.93 (p, J = 7.5 Hz, 2H), 1.66-1.56 (m, 2H), 1.49-1.26 (m, 16H), 1.20-1.14 (m, 2H).<br>MS (ESI) m/z: 619 [M—Br]$^+$. |
| IB-30 | 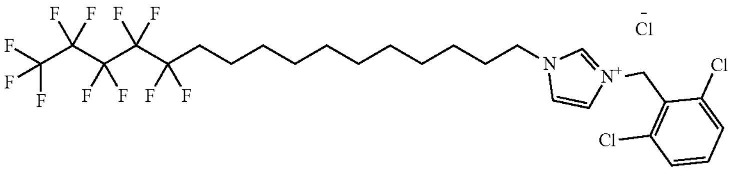 [SMILES: FC(F)(F)C(F)(F)C(F)(F)C(F)(F)C(F)(F)CCCCCCCCCCCn1cc[n+](Cc2c(Cl)cccc2Cl)c1 ; [Cl-]] | $^1$H NMR (600 MHz, Methanol-$d_4$) δ 9.24 (s, 1H), 7.74 (d, J = 1.8 Hz, 1H), 7.63 (d, J = 1.9 Hz, 1H), 7.59 (d, J = 8.1 Hz, 2H), 7.52 (dd, J = 8.8, 7.3 Hz, 1H), 5.79 (s, 2H), 4.27 (t, J = 7.2 Hz, 2H), 2.16 (tt, J = 18.7, 7.9 Hz, 2H), 1.94-1.84 (m, 2H), 1.68-1.57 (m, 2H), 1.43-1.29 (m, 14H).<br>MS (ESI) m/z: 649 [M—Cl]$^+$. |
| IB-31 | 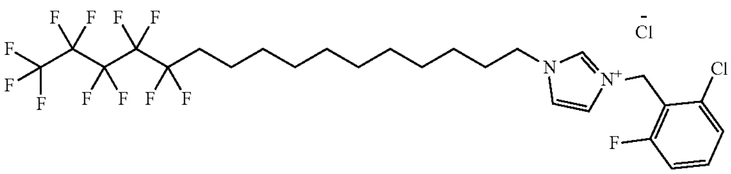 [SMILES: Fc1cccc(Cl)c1C[n+]1ccn(CCCCCCCCCCCC(F)(F)C(F)(F)C(F)(F)C(F)(F)C(F)(F)F)c1 ; [Cl-]] | $^1$H NMR (600 MHz, Methanol-$d_4$) δ 9.23 (s, 1H), 7.73 (t, J = 1.9 Hz, 1H), 7.64 (t, J = 2.0 Hz, 1H), 7.55 (td, J = 8.3, 6.2 Hz, 1H), 7.44 (d, J = 8.2 Hz, 1H), 7.34-7.27 (m, 1H), 5.68 (d, J = 1.6 Hz, 2H), 4.26 (t, J = 7.3 Hz, 2H), 2.22-2.08 (m, 2H), 1.90 (p, J = 7.3 Hz, 2H), 1.67-1.54 (m, 2H), 1.43-1.29 (m, 14H).<br>MS (ESI) m/z: 633 [M—Cl]$^+$. |
| IB-32 | 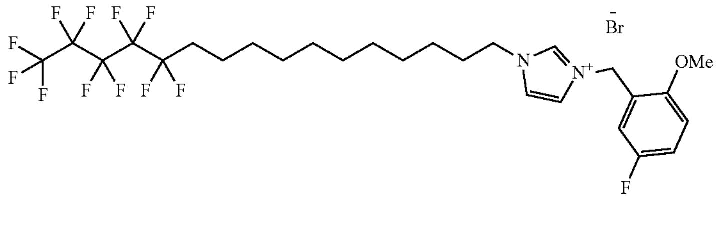 [SMILES: COc1ccc(F)cc1C[n+]1ccn(CCCCCCCCCCCC(F)(F)C(F)(F)C(F)(F)C(F)(F)C(F)(F)F)c1 ; [Br-]] | $^1$H NMR (600 MHz, Methanol-$d_4$) δ 9.17 (s, 1H), 7.67 (t, J = 1.9 Hz, 1H), 7.64 (t, J = 1.9 Hz, 1H), 7.31 (dd, J = 8.4, 3.1 Hz, 1H), 7.18 (td, J = 8.6, 3.1 Hz, 1H), 7.08 (dd, J = 9.1, 4.3 Hz, 1H), 5.41 (s, 2H), 4.26 (t, J = 7.3 Hz, 2H), 3.89 (s, 3H), 2.16 (s, 2H), 1.90 (p, J = 7.4 Hz, 2H), 1.66-1.56 (m, 2H), 1.42-1.29 (m, 14H).<br>MS (ESI) m/z: 629 [M—Br]$^+$. |

TABLE 1-continued

Structure and characterization of compounds IA-IB

| No. | Structure | $^{1}$H NMR and/or MS data |
| --- | --- | --- |
| IB-33 | 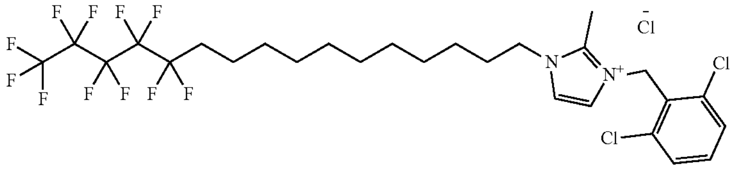 | $^{1}$H NMR (600 MHz, Methanol-$d_4$) δ 7.62-7.57 (m, 3H), 7.53 (dd, J = 8.9, 7.3 Hz, 1H), 7.15 (d, J = 2.3 Hz, 1H), 5.68 (s, 2H), 4.24 (t, J = 7.3 Hz, 2H), 2.84 (s, 3H), 2.22-2.02 (m, 2H), 1.86 (p, J = 7.5 Hz, 2H), 1.65-1.56 (m, 2H), 1.39-1.33 (m, 14H). MS (ESI) m/z: 633 $[M—Cl]^+$. |
| IB-34 | 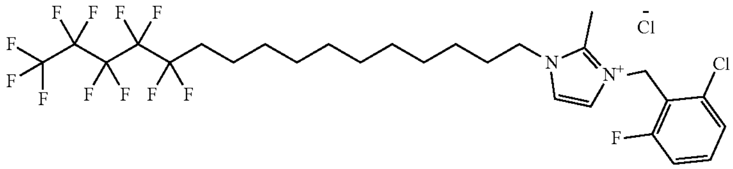 [SMILES: Cc1n(CCCCCCCCCCCC(F)(F)C(F)(F)C(F)(F)C(F)(F)C(F)(F)F)cc[n+]1Cc1c(F)cccc1Cl ; [Cl-]] | $^{1}$H NMR (600 MHz, Methanol-$d_4$) δ 7.60 (d, J = 2.3 Hz, 1H), 7.56 (td, J = 8.3, 6.1 Hz, 1H), 7.45 (dt, J = 8.1, 1.1 Hz, 1H), 7.38 (d, J = 2.2 Hz, 1H), 7.30 (ddd, J = 9.6, 8.4, 1.1 Hz, 1H), 5.60 (d, J = 1.4 Hz, 2H), 4.21 (t, J = 7.4 Hz, 2H), 2.79 (s, 3H), 2.22-2.03 (m, 2H), 1.85 (p, J = 7.5 Hz, 2H), 1.67-1.56 (m, 2H), 1.41-1.27 (m, 14H). MS (ESI) m/z: 647 $[M—Cl]^+$. |
| IB-35 | 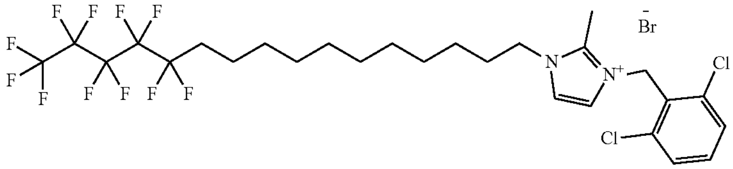 | $^{1}$H NMR (600 MHz, Methanol-$d_4$) δ 7.64-7.57 (m, 3H), 7.53 (dd, J = 8.9, 7.3 Hz, 1H), 7.15 (d, J = 2.2 Hz, 1H), 5.68 (s, 2H), 4.24 (t, J = 7.4 Hz, 2H), 2.85 (s, 3H), 2.24-2.03 (m, 2H), 1.87 (p, J = 7.4 Hz, 2H), 1.67-1.56 (m, 2H), 1.38-1.33 (m, 14H). MS (ESI) m/z: 663 $[M—Br]^+$ |
| IB-36 | 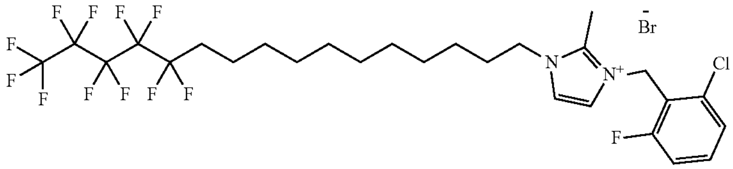 [SMILES: Cc1n(CCCCCCCCCCCC(F)(F)C(F)(F)C(F)(F)C(F)(F)C(F)(F)F)cc[n+]1Cc1c(F)cccc1Cl ; [Br-]] | $^{1}$H NMR (600 MHz, Methanol-$d_4$) δ 7.61 (d, J = 2.3 Hz, 1H), 7.56 (td, J = 8.3, 6.1 Hz, 1H), 7.48-7.43 (m, 1H), 7.38 (d, J = 2.2 Hz, 1H), 7.30 (ddd, J = 9.5, 8.3, 1.1 Hz, 1H), 5.60 (d, J = 1.4 Hz, 2H), 4.22 (t, J = 7.4 Hz, 2H), 2.81 (s, 3H), 2.23-2.10 (m, 2H), 1.91-1.82 (m, 2H), 1.67-1.56 (m, 2H), 1.42-1.30 (m, 14H). MS (ESI) m/z: 647 $[M—Br]^+$. |
| IB-37 | 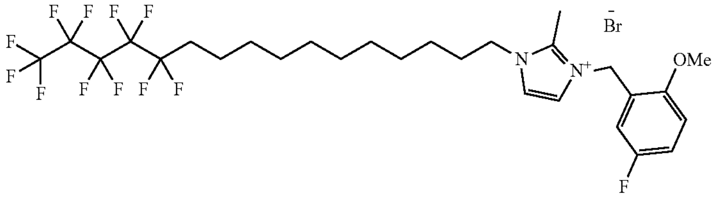 [SMILES: COc1ccc(F)cc1C[n+]1ccn(CCCCCCCCCCCC(F)(F)C(F)(F)C(F)(F)C(F)(F)C(F)(F)F)c1C ; [Br-]] | $^{1}$H NMR (600 MHz, Methanol-$d_4$) δ 7.57 (d, J = 2.2 Hz, 1H), 7.48 (d, J = 2.1 Hz, 1H), 7.22-7.14 (m, 2H), 7.08 (dd, J = 9.0, 4.3 Hz, 1H), 5.35 (s, 2H), 4.20 (t, J = 7.4 Hz, 2H), 3.86 (s, 3H), 2.75 (s, 3H), 2.23-2.09 (m, 2H), 1.85 (p, J = 7.5 Hz, 2H), 1.66-1.54 (m, 2H), 1.41-1.30 (m, 14H). MS (ESI) m/z: 643 $[M—Br]^+$. |
| IB-38 | 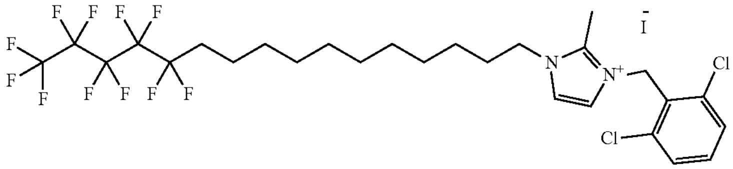 [SMILES: Cc1n(CCCCCCCCCCCC(F)(F)C(F)(F)C(F)(F)C(F)(F)C(F)(F)F)cc[n+]1Cc1c(Cl)cccc1Cl ; [I-]] | $^{1}$H NMR (600 MHz, Methanol-$d_4$) δ 7.63-7.57 (m, 3H), 7.53 (dd, J = 8.9, 7.3 Hz, 1H), 7.15 (d, J = 2.3 Hz, 1H), 5.68 (s, 2H), 4.24 (t, J = 7.4 Hz, 2H), 2.86 (s, 3H), 2.22-2.10 (m, 2H), 1.87 (p, J = 7.7 Hz, 2H), 1.66-1.57 (m, 2H), 1.41-1.30 (m, 14H). MS (ESI) m/z: 663 $[M—I]^+$. |
| IB-39 | 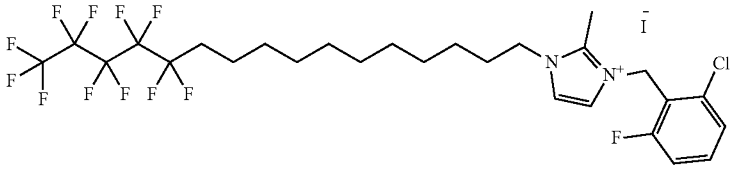 [SMILES: Cc1n(CCCCCCCCCCCC(F)(F)C(F)(F)C(F)(F)C(F)(F)C(F)(F)F)cc[n+]1Cc1c(F)cccc1Cl ; [I-]] | $^{1}$H NMR (600 MHz, Methanol-$d_4$) δ 6.09 (d, J = 2.3 Hz, 1H), 6.02 (td, J = 8.3, 6.1 Hz, 1H), 5.91 (dt, J = 8.3, 1.1 Hz, 1H), 5.84 (d, J = 2.1 Hz, 1H), 5.76 (ddd, J = 9.5, 8.3, 1.1 Hz, 1H), 4.07 (d, J = 1.4 Hz, 2H), 2.69 (t, J = 7.4 Hz, 2H), 1.29 (s, 3H), 0.68-0.57 (m, 2H), 0.37-0.27 (m, 2H), 0.13-0.03 (m, 2H), −0.13-−0.22 (m, 14H). MS (ESI) m/z: 647 $[M—I]^+$. |

TABLE 1-continued

Structure and characterization of compounds IA-IB

| No. | Structure | $^1H$ NMR and/or MS data |
| --- | --- | --- |
| IB-40 | 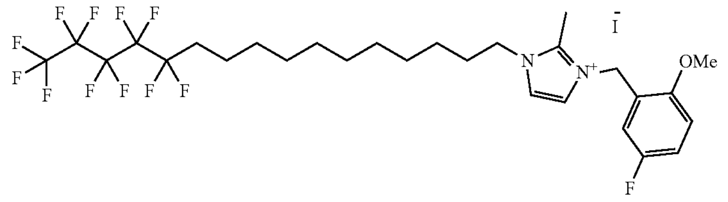 [SMILES: COc1ccc(F)cc1C[n+]1ccn(CCCCCCCCCCCC(F)(F)C(F)(F)C(F)(F)C(F)(F)C(F)(F)F)c1C ; [I-]] | $^1H$ NMR (600 MHz, Methanol-$d_4$) δ 7.58 (t, J = 1.8 Hz, 1H), 7.47 (d, J = 2.2 Hz, 1H), 7.21 (dd, J = 8.5, 3.1 Hz, 1H), 7.17 (td, J = 8.6, 3.1 Hz, 1H), 7.08 (dd, J = 9.1, 4.3 Hz, 1H), 5.36 (s, 2H), 4.21 (t, J = 7.5 Hz, 2H), 2.76 (s, 3H), 2.22-2.10 (m, 2H), 1.90-1.79 (m, 2H), 1.67-1.56 (m, 2H), 1.43-1.30 (m, 14H). MS (ESI) m/z: 643 $[M—I]^+$. |
| IB-41 | 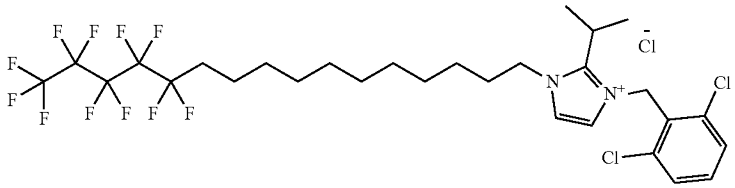 [SMILES: CC(C)c1n(CCCCCCCCCCCC(F)(F)C(F)(F)C(F)(F)C(F)(F)C(F)(F)F)cc[n+]1Cc1c(Cl)cccc1Cl ; [Cl-]] | $^1H$ NMR (600 MHz, Methanol-$d_4$) δ 7.65-7.61 (m, 2H), 7.58 (d, J = 2.3 Hz, 1H), 7.57-7.53 (m, 1H), 7.00 (d, J = 2.3 Hz, 1H), 5.76 (s, 2H), 4.33-4.25 (m, 2H), 3.91 (p, J = 7.3 Hz, 1H), 2.23-2.09 (m, 2H), 1.89 (q, J = 7.3 Hz, 2H), 1.66-1.56 (m, 8H), 1.47-1.33 (m, 14H). MS (ESI) m/z: 691 $[M—Cl]^+$. |
| IB-42 | 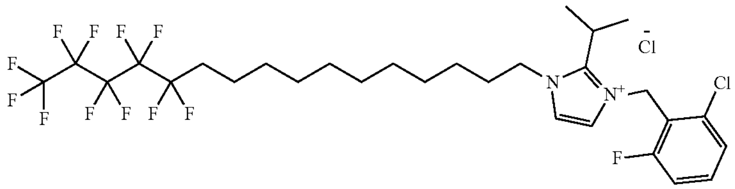 [SMILES: CC(C)c1n(CCCCCCCCCCCC(F)(F)C(F)(F)C(F)(F)C(F)(F)C(F)(F)F)cc[n+]1Cc1c(F)cccc1Cl ; [Cl-]] | $^1H$ NMR (600 MHz, Methanol-$d_4$) δ 7.60-7.55 (m, 2H), 7.48 (dt, J = 8.2, 1.1 Hz, 1H), 7.31 (ddd, J = 9.7, 8.4, 1.1 Hz, 1H), 7.23 (d, J = 2.1 Hz, 1H), 5.68 (d, J = 1.3 Hz, 2H), 4.33-4.25 (m, 2H), 3.87 (p, J = 7.3 Hz, 1H), 2.23-2.09 (m, 2H), 1.93-1.83 (m, 2H), 1.68-1.57 (m, 2H), 1.55 (d, J = 7.3 Hz, 6H), 1.47-1.32 (m, 14H). MS (ESI) m/z: 675 $[M—Cl]^+$. |
| IB-43 | 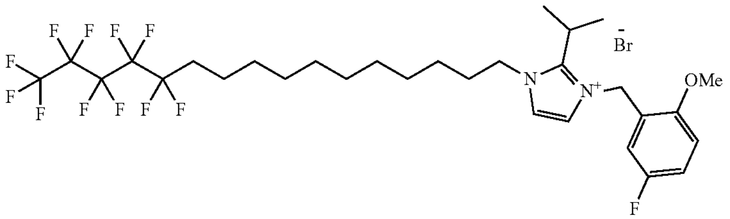 [SMILES: COc1ccc(F)cc1C[n+]1ccn(CCCCCCCCCCCC(F)(F)C(F)(F)C(F)(F)C(F)(F)C(F)(F)F)c1C(C)C ; [Br-]] | $^1H$ NMR (600 MHz, Methanol-$d_4$) δ 7.60 (d, J = 2.3 Hz, 1H), 7.39 (d, J = 2.2 Hz, 1H), 7.19 (ddd, J = 9.1, 8.1, 3.1 Hz, 1H), 7.11 (dt, J = 9.0, 3.6 Hz, 2H), 5.45 (s, 2H), 4.31-4.25 (m, 2H), 3.86 (s, 3H), 3.85-3.79 (m, 1H), 2.23-2.10 (m, 2H), 1.90 (p, J = 8.2 Hz, 2H), 1.66-1.58 (m, 2H), 1.48 (d, J = 7.3 Hz, 6H), 1.46-1.28 (m, 14H). MS (ESI) m/z: 671 $[M—Br]^+$. |
| IB-44 | 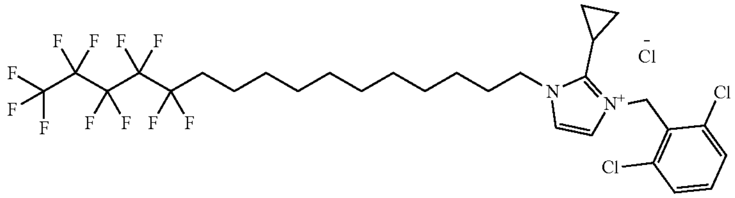 [SMILES: FC(F)(F)C(F)(F)C(F)(F)C(F)(F)C(F)(F)CCCCCCCCCCCn1cc[n+](Cc2c(Cl)cccc2Cl)c1C1CC1 ; [Cl-]] | $^1H$ NMR (600 MHz, Methanol-$d_4$) δ 7.63-7.56 (m, 3H), 7.53 (dd, J = 8.9, 7.3 Hz, 1H), 7.24 (d, J = 2.6 Hz, 0H), 7.07 (d, J = 2.2 Hz, 1H), 5.81 (s, 2H), 4.35 (t, J = 7.3 Hz, 2H), 2.24-2.09 (m, 3H), 1.93 (p, J = 7.3 Hz, 2H), 1.65-1.57 (m, 2H), 1.52-1.46 (m, 2H), 1.42-1.27 (m, 14H), 1.27-1.21 (m, 2H). MS (ESI) m/z: 689 $[M—Cl]^+$. |
| IB-45 | 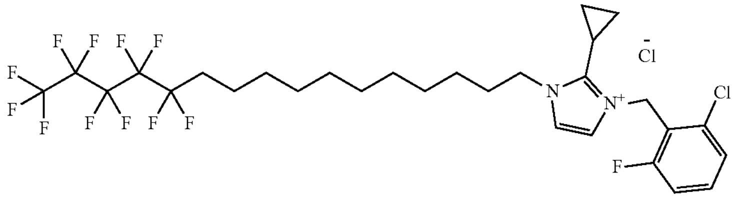 [SMILES: Fc1cccc(Cl)c1C[n+]1ccn(CCCCCCCCCCCC(F)(F)C(F)(F)C(F)(F)C(F)(F)C(F)(F)F)c1C1CC1 ; [Cl-]] | MS (ESI) m/z: 673 $[M—Cl]^+$. |
| IB-46 | 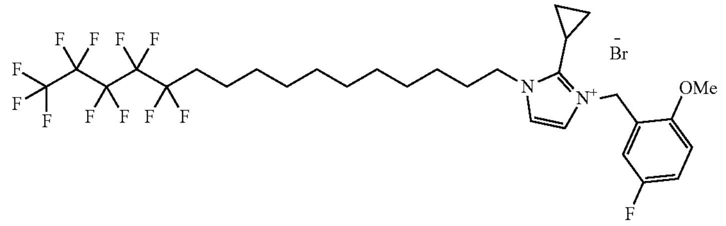 [SMILES: COc1ccc(F)cc1C[n+]1ccn(CCCCCCCCCCCC(F)(F)C(F)(F)C(F)(F)C(F)(F)C(F)(F)F)c1C1CC1 ; [Br-]] | $^1H$ NMR (600 MHz, Methanol-$d_4$) δ 7.57 (d, J = 2.2 Hz, 1H), 7.38 (d, J = 2.2 Hz, 1H), 7.21-7.13 (m, 2H), 7.09 (dd, J = 8.9, 4.3 Hz, 1H), 5.47 (s, 2H), 4.32 (t, J = 7.5 Hz, 2H), 3.85 (s, 3H), 2.23-2.09 (m, 2H), 1.99 (tt, J = 8.5, 5.6 Hz, 1H), 1.96-1.84 (m, 2H), 1.67-1.57 (m, 2H), 1.43-1.32 (m, 16H), 1.19-1.14 (m, 2H). MS (ESI) m/z: 669 $[M—Br]^+$. |

TABLE 1-continued

Structure and characterization of compounds IA-IB

| No. | Structure | $^1H$ NMR and/or MS data |
| --- | --- | --- |
| IB-47 | 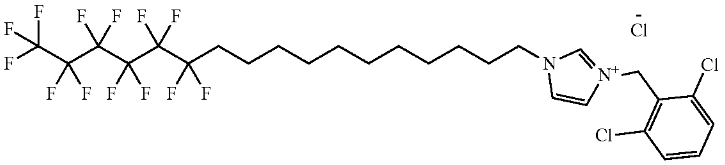 [SMILES: FC(F)(F)C(F)(F)C(F)(F)C(F)(F)C(F)(F)C(F)(F)CCCCCCCCCCCn1cc[n+](Cc2c(Cl)cccc2Cl)c1 ; [Cl-]] | $^1H$ NMR (600 MHz, Methanol-$d_4$) δ 9.19 (s, 1H), 7.70-7.69 (m, 1H), 7.59 (d, J = 2.2 Hz, 1H), 7.57 (d, J = 0.9 Hz, 1H), 7.55 (s, 1H), 7.48 (dd, J = 8.8, 7.3 Hz, 1H), 5.75 (s, 2H), 4.23 (t, J = 7.2 Hz, 2H), 2.18-2.06 (m, 2H), 1.91-1.81 (m, 2H), 1.63-1.54 (m, 2H), 1.42-1.36 (m, 2H), 1.34-1.25 (m, 12H). MS (ESI) m/z: 699 [M—Cl]$^+$. |
| IB-48 | 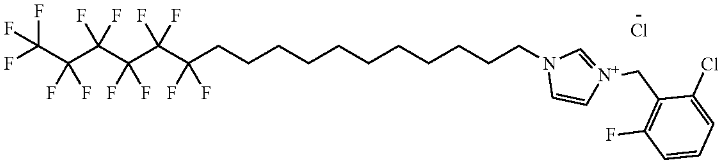 [SMILES: Fc1cccc(Cl)c1C[n+]1ccn(CCCCCCCCCCCC(F)(F)C(F)(F)C(F)(F)C(F)(F)C(F)(F)C(F)(F)F)c1 ; [Cl-]] | $^1H$ NMR (600 MHz, Methanol-$d_4$) δ 7.70 (d, J = 2.0 Hz, 1H), 7.61 (d, J = 2.1 Hz, 1H), 7.55-7.51 (m, 1H), 7.43-7.40 (m, 1H), 7.30-7.26 (m, 1H), 5.66 (d, J = 1.6 Hz, 2H), 4.24 (t, J = 7.3 Hz, 2H), 2.20-2.05 (m, 2H), 1.88 (p, J = 7.4 Hz, 2H), 1.63-1.56 (m, 2H), 1.44-1.37 (m, 2H), 1.36-1.29 (m, 12H). MS (ESI) m/z: 683 [M—Cl]$^+$. |
| IB-49 | 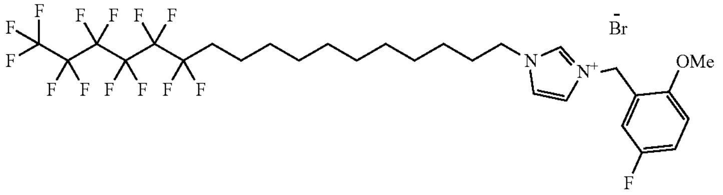 [SMILES: COc1ccc(F)cc1C[n+]1ccn(CCCCCCCCCCCC(F)(F)C(F)(F)C(F)(F)C(F)(F)C(F)(F)C(F)(F)F)c1 ; [Br-]] | $^1H$ NMR (600 MHz, Methanol-$d_4$) δ 9.10 (s, 1H), 7.62 (t, J = 1.9 Hz, 1H), 7.60 (t, J = 1.8 Hz, 1H), 7.26 (dd, J = 8.4, 3.1 Hz, 1H), 7.18-7.12 (m, 1H), 7.05 (dd, J = 9.0, 4.3 Hz, 1H), 5.37 (s, 2H), 4.22 (t, J = 7.2 Hz, 2H), 3.85 (s, 3H), 2.22-2.03 (m, 2H), 1.87 (p, J = 7.4 Hz, 2H), 1.62-1.54 (m, 2H), 1.42-1.37 (m, 2H), 1.34-1.27 (m, 12H). MS (ESI) m/z: 679 [M—Br]$^+$. |
| IB-50 | 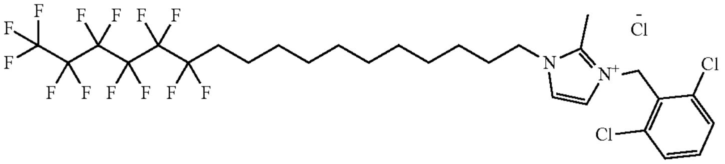 [SMILES: Cc1n(CCCCCCCCCCCC(F)(F)C(F)(F)C(F)(F)C(F)(F)C(F)(F)C(F)(F)F)cc[n+]1Cc1c(Cl)cccc1Cl ; [Cl-]] | $^1H$ NMR (600 MHz, Chloroform-d) δ 7.74 (d, J = 2.1 Hz, 1H), 7.41 (d, J = 1.5 Hz, 1H), 7.40 (s, 1H), 7.35 (dd, J = 9.1, 7.0 Hz, 1H), 6.95 (d, J = 2.2 Hz, 1H), 5.64 (s, 2H), 4.32 (t, J = 7.4 Hz, 2H), 2.99 (s, 3H), 2.07-1.91 (m, 2H), 1.85-1.74 (m, 2H), 1.61-1.49 (m, 2H), 1.35-1.31 (m, 2H), 1.29-1.19 (m, 12H). MS (ESI) m/z: 713 [M—Cl]$^+$. |
| IB-51 | 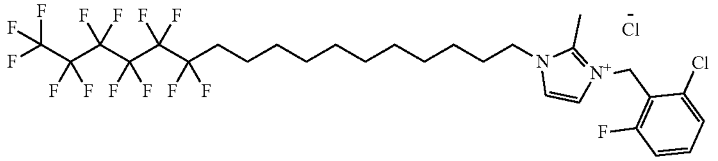 [SMILES: Cc1n(CCCCCCCCCCCC(F)(F)C(F)(F)C(F)(F)C(F)(F)C(F)(F)C(F)(F)F)cc[n+]1Cc1c(F)cccc1Cl ; [Cl-]] | $^1H$ NMR (600 MHz, Chloroform-d) δ 7.61 (d, J = 2.1 Hz, 1H), 7.38 (td, J = 8.3, 6.1 Hz, 1H), 7.28 (d, J = 8.1 Hz, 1H), 7.22 (d, J = 1.9 Hz, 1H), 7.10 (t, J = 8.8 Hz, 1H), 5.58 (s, 2H), 4.27 (t, J = 7.5 Hz, 2H), 2.92 (s, 3H), 2.02 (dq, J = 17.5, 9.1 Hz, 2H), 1.79 (p, J = 7.7 Hz, 2H), 1.60-1.52 (m, 2H), 1.34-1.21 (m, 14H). MS (ESI) m/z: 697 [M—Cl]$^+$. |
| IB-52 | 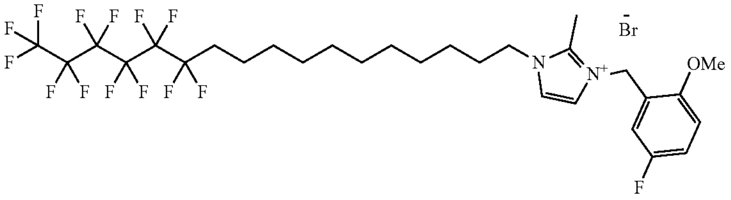 | $^1H$ NMR (600 MHz, Methanol-$d_4$) δ 7.54 (d, J = 2.2 Hz, 1H), 7.45 (d, J = 2.2 Hz, 1H), 7.17 (dd, J = 8.7, 2.9 Hz, 1H), 7.15-7.12 (m, 1H), 7.05 (dd, J = 8.9, 4.3 Hz, 1H), 5.32 (s, 2H), 4.17 (t, J = 7.4 Hz, 2H), 3.84 (s, 3H), 2.71 (s, 3H), 2.21-2.06 (m, 2H), 1.83 (p, J = 7.5 Hz, 2H), 1.59 (p, J = 7.7 Hz, 2H), 1.43-1.37 (m, 2H), 1.37-1.30 (m, 12H). MS (ESI) m/z: 693 [M—Br]$^+$. |
| IB-53 | 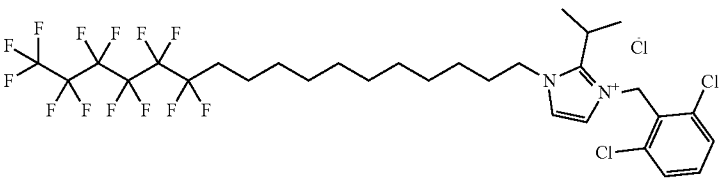 [SMILES: CC(C)c1n(CCCCCCCCCCCC(F)(F)C(F)(F)C(F)(F)C(F)(F)C(F)(F)C(F)(F)F)cc[n+]1Cc1c(Cl)cccc1Cl ; Cl] | $^1H$ NMR (600 MHz, Chloroform-d) δ 8.10 (d, J = 2.3 Hz, 1H), 7.45-7.37 (m, 3H), 6.77 (d, J = 2.1 Hz, 1H), 5.62 (s, 2H), 4.39 (t, J = 7.7 Hz, 2H), 3.91-3.82 (m, 1H), 2.07-1.91 (m, 2H), 1.87-1.77 (m, 2H), 1.54 (d, J = 7.2 Hz, 6H), 1.35-1.20 (m, 16H). MS (ESI) m/z: 741 [M—Cl]$^+$. |
| IB-54 | 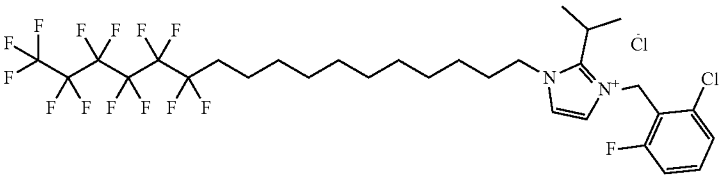 [SMILES: CC(C)c1n(CCCCCCCCCCCC(F)(F)C(F)(F)C(F)(F)C(F)(F)C(F)(F)C(F)(F)F)cc[n+]1Cc1c(F)cccc1Cl ; Cl] | $^1H$ NMR (600 MHz, Chloroform-d) δ 8.04 (d, J = 2.1 Hz, 1H), 7.44-7.38 (m, 1H), 7.29 (d, J = 8.2 Hz, 1H), 7.18-7.14 (m, 1H), 7.12-7.07 (m, 1H), 5.60 (s, 2H), 4.34 (t, J = 7.8 Hz, 2H), 3.86-3.79 (m, 1H), 2.06-1.93 (m, 2H), 1.87-1.79 (m, 2H), 1.57-1.50 (m, 2H), 1.48 (d, J = 7.2 Hz, 6H), 1.34-1.21 (m, 14H). |

TABLE 1-continued

Structure and characterization of compounds IA-IB

| No. | Structure | $^1$H NMR and/or MS data |
|---|---|---|
| | | MS (ESI) m/z: 7.25 $[M—Cl]^+$. |
| IB-55 | 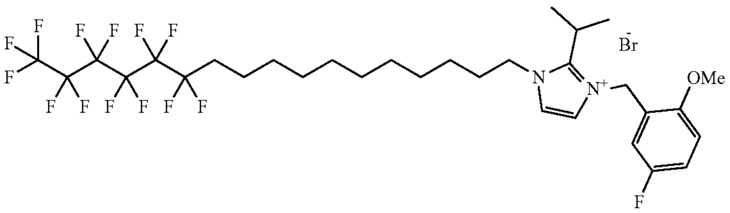 [SMILES: COc1ccc(F)cc1C[n+]1ccn(CCCCCCCCCCCC(F)(F)C(F)(F)C(F)(F)C(F)(F)C(F)(F)C(F)(F)F)c1C(C)C ; Br] | $^1$H NMR (600 MHz, Chloroform-d) δ 7.75 (d, J = 1.9 Hz, 1H), 7.42 (d, J = 1.9 Hz, 1H), 7.10 (dd, J = 8.2, 3.1 Hz, 1H), 7.07-7.01 (m, 1H), 6.85 (dd, J = 9.0, 4.2 Hz, 1H), 5.48 (s, 2H), 4.28 (t, J = 7.8 Hz, 2H), 3.78 (s, 3H), 3.76 (t, J = 7.2 Hz, 1H), 2.07-1.95 (m, 2H), 1.85 (s, 2H), 1.60-1.51 (m, 2H), 1.43 (d, J = 7.2 Hz, 6H), 1.33-1.22 (m, 14H). MS (ESI) m/z: 721 $[M—Br]^+$. |
| IB-56 | 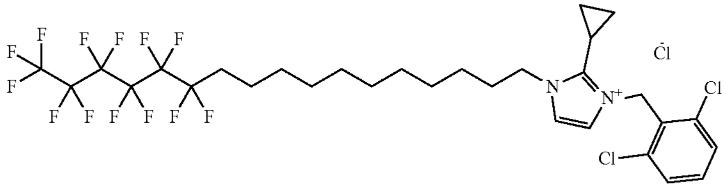 [SMILES: FC(F)(F)C(F)(F)C(F)(F)C(F)(F)C(F)(F)C(F)(F)CCCCCCCCCCCn1cc[n+](Cc2c(Cl)cccc2Cl)c1C1CC1 ; Cl] | $^1$H NMR (600 MHz, Chloroform-d) δ 7.93 (s, 1H), 7.44 (d, J = 1.3 Hz, 1H), 7.43 (s, 1H), 7.38 (dd, J = 9.0, 6.9 Hz, 1H), 6.82 (s, 1H), 5.71 (s, 2H), 4.43 (t, J = 7.4 Hz, 2H), 2.09-2.05 (m, 1H), 2.04-1.96 (m, 2H), 1.88 (brs, 2H), 1.59-1.53 (m, 2H), 1.46 (d, J = 8.0 Hz, 2H), 1.37-1.32 (m, 4H), 1.31-1.28 (m, 4H), 1.26-1.21 (m, 8H). MS (ESI) m/z: 739 $[M—Cl]^+$. |
| IB-57 | 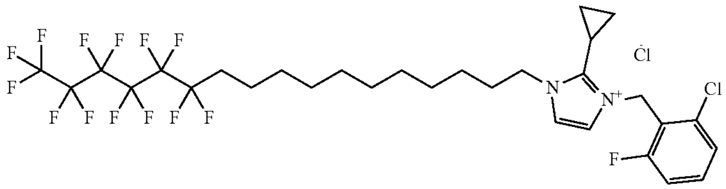 [SMILES: Fc1cccc(Cl)c1C[n+]1ccn(CCCCCCCCCCCC(F)(F)C(F)(F)C(F)(F)C(F)(F)C(F)(F)C(F)(F)F)c1C1CC1 ; Cl] | $^1$H NMR (600 MHz, Chloroform-d) δ 7.80 (d, J = 2.2 Hz, 1H), 7.40-7.35 (m, 1H), 7.27 (d, J = 8.1 Hz, 1H), 7.11-7.05 (m, 2H), 5.64 (s, 2H), 4.35 (t, J = 7.6 Hz, 2H), 2.08-1.96 (m, 3H), 1.84 (t, J = 7.4 Hz, 2H), 1.58-1.50 (m, 2H), 1.45-1.39 (m, 2H), 1.33-1.24 (m, 12H), 1.22-1.20 (m, 4H). MS (ESI) m/z: 723 $[M—Cl]^+$. |
| IB-58 | 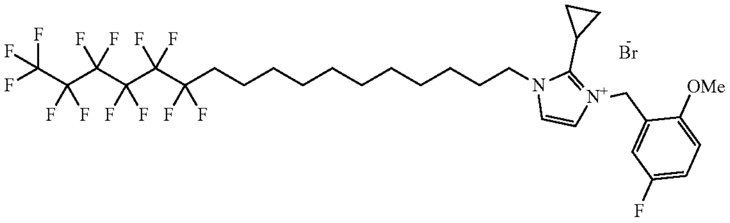 [SMILES: COc1ccc(F)cc1C[n+]1ccn(CCCCCCCCCCCC(F)(F)C(F)(F)C(F)(F)C(F)(F)C(F)(F)C(F)(F)F)c1C1CC1 ; Br] | $^1$H NMR (600 MHz, Chloroform-d) δ 7.57 (d, J = 2.2 Hz, 1H), 7.22 (d, J = 2.2 Hz, 1H), 7.13 (dd, J = 8.2, 3.1 Hz, 1H), 7.07-7.02 (m, 1H), 6.84 (dd, J = 9.0, 4.3 Hz, 1H), 5.49 (s, 2H), 4.32 (t, J = 7.7 Hz, 2H), 3.77 (s, 3H), 2.06-1.96 (m, 3H), 1.90-1.83 (m, 2H), 1.60-1.52 (m, 2H), 1.41-1.36 (m, 2H), 1.36-1.29 (m, 6H), 1.29-1.21 (m, 11H). MS (ESI) m/z: 719 $[M—Br]^+$. |
| IB-59 | 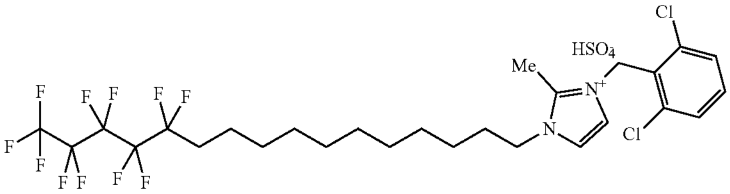 [SMILES: Cc1n(CCCCCCCCCCCC(F)(F)C(F)(F)C(F)(F)C(F)(F)C(F)(F)F)cc[n+]1Cc1c(Cl)cccc1Cl ; "HSO4"] | $^1$H NMR (600 MHz, Methanol-$d_4$) δ 7.60-7.54 (m, 3H), 7.51 (dd, J = 8.9, 7.3 Hz, 1H), 7.13 (d, J = 2.3 Hz, 1H), 5.65 (s, 2H), 4.21 (t, J = 7.4 Hz, 2H), 2.82 (s, 3H), 2.14 (tt, J = 18.7, 8.0 Hz, 2H), 1.84 (p, J = 7.0 Hz, 2H), 1.60 (p, J = 8.0 Hz, 2H), 1.45-1.29 (m, 14H). MS (ESI) m/z: 663 $[M—HSO_4]^+$ |
| IB-60 | 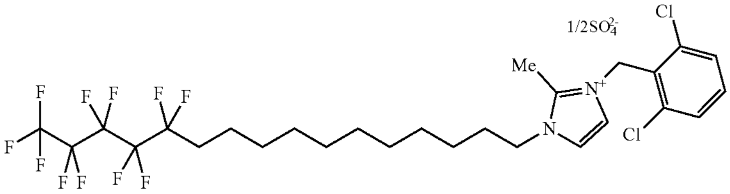 [SMILES: Cc1n(CCCCCCCCCCCC(F)(F)C(F)(F)C(F)(F)C(F)(F)C(F)(F)F)cc[n+]1Cc1c(Cl)cccc1Cl] | $^1$H NMR (600 MHz, Methanol-$d_4$) δ 7.60-7.55 (m, 3H), 7.51 (dd, J = 8.8, 7.3 Hz, 1H), 7.13 (d, J = 2.3 Hz, 1H), 5.66 (s, 2H), 4.22 (t, J = 7.3 Hz, 2H), 2.82 (s, 3H), 2.14 (tt, J = 18.8, 8.0 Hz, 2H), 1.84 (p, J = 7.3 Hz, 2H), 1.60 (p, J = 7.8 Hz, 2H), 1.45-1.28 (m, 14H). MS (ESI) m/z: 663 $[M—½SO_4]^+$ |

Test Examples

Biological Activity Assay:

I. AMPK Activity Assay at Cell Level

The ability of compounds to activate AMPK in mouse embryonic fibroblasts (MEFs) was determined, which could be specifically carried out by detecting the phosphorylation level (p-AMPKα) of threonine at the 172$^{nd}$ position of AMPK and the phosphorylation level (p-ACC) of serine at the 79$^{th}$ position of the susbtrate ACC1/ACC2 of AMPK (FIG. 1 and Table I) by western blot.

The specific method was as follows:

(1) MEFs with loxP insertion sequences or of wild-type were plated in a 6-well plate and cultured in DMEM containing 10% serum. If a gene needed to be knocked out at this time, when the density of the corresponding MEFs with loxP insertion sequences reached about 30%, an adenovirus capable of expressing cre should be added to the culture well followed by further culture for more than 24 h;

(2) When the cell density was close to 90%, the cells were provided with fresh DMEM, at the same time, a compound (final concentration 10 nM) was added to the cells, followed by culture for 2 h, with an equal volume of DMSO as the negative control, and the cells treated with the addition of AICAR (3 mM) as the positive control;

(3) After sucking up the culture solution, the cells were lysed with 200 μL of a cell lysate (its formulation was given below), then the cells were scraped from the culture dish, ultrasonicated, and subjected to low temperature centrifugation at 20000 g for 10 min;

(4) The supernatant and an equal volume of 2*SDS solution (its formulation was given below) were mixed, and subjected to SDS-PAGE in a concentration of 8%, then the protein was transferred to PVDF membrane; each PVDF membrane was blocked with 25 mL of skim milk for 1 h, and then rinsed with TBST buffer (its formulation was given below) 3 times for 10 min each time;

(5) AMPKα subunit primary antibody (Cell Signaling Technology, #2532), primary antibody of phosphothreonine at the $172^{nd}$ position of AMPK (Cell Signaling Technology, #2535), ACC primary antibody (Cell Signaling Technology, #3662), or primary antibody of phosphoserine at the $79^{th}$ position of ACC (Cell Signaling Technology, #3661) was diluted in a ratio of 1:1000 with a primary antibody dilution (its formulation was given below), reacted with the PVDF membrane at room temperature for 12 h, and then rinsed 3 times with TBST buffer;

(6) A 1:1000 dilution of HRP-conjugated goat anti-rabbit secondary antibody (Jackson ImmunoResearch, 111-035-003) was added, reacted at room temperature for 1 h, and then rinsed 3 times with TBST buffer;

(7) The PVDF membrane was dried, reacted in an ECL mixture (WesternBright ECL HRP substrate, Advansta) and subjected to exposure with medical X-ray, developed, finally rinsed, dried, and then scanned to obtain data related to AMPK activation.

The formulations of reagents used were:

Cell lysate: 20 mM Tris-base, pH 7.5, 150 mM NaCl, 1 mM EDTA, 1 mM EGTA, 2.5 mM Sodium pyrophosphate, 1 mM β-glycerolphosphate, 1% Triton X-100 (v/v);

2*SDS solution: 20% Glycerol (v/v), 4% SDS (m/v), 10% β-mecaptoethanol (v/v), 0.01% Bromophenol blue (m/v);

TBST buffer: 4.84% Tris-base (m/v), 8% NaCl (m/v), 0.1% Tween-20 (v/v);

Primary antibody dilution: TBST buffer containing 5% BSA (v/v).

TABLE 1

The ability of compounds to activate AMPK in MEF cells

| No. | Degree of AMPK activation[a] p-AMPKα/AMPK | p-ACC/ACC |
|---|---|---|
| IA-1 | 1.01 | 0.42 |
| IA-2 | 1.00 | 0.73 |
| IA-3 | 0.69 | 0.83 |
| IB-1 | 0.99 | 0.71 |
| IB-2 | 1.45 | 0.82 |
| IB-3 | 1.70 | 0.64 |
| IB-4 | 1.66 | 0.80 |
| IB-5 | 1.85 | 0.70 |
| IB-7 | 1.93 | 0.87 |
| IB-8 | 1.23 | 0.90 |
| IB-9 | 1.07 | 0.27 |
| IB-10 | 1.94 | 0.35 |
| IB-11 | 1.11 | 0.41 |
| IB-12 | 1.18 | 0.50 |
| IB-13 | 1.31 | 0.57 |
| IB-14 | 1.57 | 0.50 |
| IB-16 | 2.28 | 0.77 |
| IB-17 | 1.42 | 0.72 |
| IB-18 | 1.45 | 0.65 |
| IB-20 | 1.22 | 0.82 |
| IB-21 | 0.35 | 1.73 |
| IB-22 | 0.44 | 1.08 |
| IB-23 | 0.49 | 1.50 |
| IB-24 | 0.64 | 1.60 |
| IB-25 | 0.58 | 1.10 |
| IB-26 | 0.94 | 1.04 |
| IB-27 | 0.95 | 1.06 |
| IB-29 | 0.76 | 0.81 |
| IB-33 | 0.54 | 0.94 |
| IB-34 | 0.98 | 0.63 |
| IB-35 | 1.02 | 1.15 |
| IB-38 | 2.06 | 1.34 |
| IB-39 | 1.50 | 1.51 |
| IB-40 | 1.06 | 1.65 |
| IB-41 | 0.94 | 1.49 |
| IB-42 | 1.03 | 1.50 |
| IB-44 | 0.59 | 1.56 |
| IB-45 | 0.54 | 2.22 |
| IB-46 | 0.57 | 1.73 |
| IB-50 | 0.65 | 1.09 |
| IB-52 | 0.83 | 0.98 |
| IB-53 | 0.76 | 1.23 |
| IB-55 | 0.87 | 1.98 |
| IB-56 | 0.85 | 0.99 |
| IB-59 | 0.98 | 1.04 |
| IB-60 | 0.94 | 1.01 |

[a] Degree of compounds to activate AMPK in MEF cells, expressed as a multiple of the ratio of p-AMPKα/AMPKα and p-ACC/ACC after treatment with compound (10 nM) relative to the positive control AICAR (3 mM) (quantification of corresponding brightness of bands using Image J) (FIG. 1).

II. Liver Microsome Stability Test

The experimental steps were as follows:

1. Preparation of working solution 1.1 Intermediate solution: 5 μL of a 10 mM stock solution of sample or control was taken out, and diluted with 495 μl of methanol (Conc.: 100 μM, 99% MeOH).

1.2 Working solution: 50 μL of the intermediate solution was taken out, and diluted with 450 μL of a 100 mM potassium phosphate buffer (Conc.: 10 μM, 9.9% MeOH).

2. Preparation of NADPH cofactor

An appropriate amount of NADPH powder was weighed, and dissolved with a $MgCl_2$ (10 mM) solution.

3. Liver microsome 3.1 Liver microsome information

| Liver microsome | Porduct information | Source | Abbreviation |
|---|---|---|---|
| Human | Cat No. 452117<br>Lot No. 38292 | Corning | HLM |
| Beagle dog | Cat No. D1000 | Xenotech | DLM |

-continued

| Liver microsome | Porduct information | Source | Abbreviation |
|---|---|---|---|
| | Lot No. 1310086 | | |

3.2 Preparation: a microsome working solution with an appropriate concentration was prepared by using a 100 mM potassium phosphate buffer.

4. Stop solution

Glacial acetonitrile, comprising 100 ng/ml Tolbutamide and 100 ng/ml Labetalol as internal standards.

5. Experimental procedures 5.1 10 μL of the working solution of sample or control was added per well to all plates (T0, T5, T10, T20, T30, T60, NCF60), except for the blank group;

5.2 80 μL of the working solution of microsome was added per well to all plates, followed by incubation for 10 min at 37° C.;

5.3 10 μL of a 100 mM potassium phosphate buffer was added per well to NCF60, followed by incubation at 37° C. and starting timer 1;

| Time point | Start time | End time |
|---|---|---|
| NCF60 | 1:00:00 | 0:00:00 |

5.4 After preheating, 10 μL of NADPH was added per well to each plate, and reaction was started;

Final concentration of each component in the incubation medium:

| Component | Final concentration |
|---|---|
| Microsome | 0.5 mg protein/mL |
| Tested compound | 1 μM |
| Control | 1 μM |
| MeOH | 0.99% |
| DMSO | 0.01% |

5.5 Incubating at 37° C., starting timer 1;

| Time point | Start time | End time |
|---|---|---|
| Blank | 1:00:00 | 0:00:00 |
| T60 | 1:00:00 | 0:00:00 |
| T30 | 0:30:00 | 0:00:00 |
| T20 | 0:20:00 | 0:00:00 |
| T10 | 0:10:00 | 0:00:00 |
| T5 | 0:05:00 | 0:00:00 |
| T0 | The stop solution was added first, followed by the microsomal solution and the NADPH working solution | |

5.6 300 μL of the stop solution was added per well to stop the reaction;

5.7 The system was shaken for about 10 min;

5.8 The samples were centrifuged (4000 rpm) at 4° C. for 20 min;

5.9 To 8 new 96-well plates, 300 μL of HPLC water was added per well, then 100 μL of the supernatant was added, mixed and subjected to LC/MS/MS.

| Fluorine-free compound | | | Fluorine substituted compound | | |
|---|---|---|---|---|---|
| ID | HLM 0.5 $T_{1/2}$ (min) | DLM 0.5 $T_{1/2}$ (min) | ID | HLM 0.5 $T_{1/2}$ (min) | DLM 0.5 $T_{1/2}$ (min) |
| 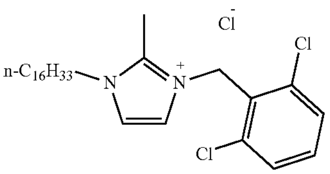 | 53.7 | 33.7 | IA-1 | 22.3 | 8.5 |
| 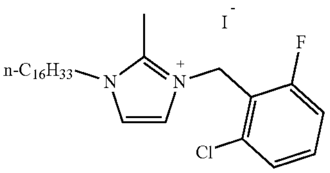 | 33.2 | 47.2 | IB-34 | 191.6 | 110.0 |
| 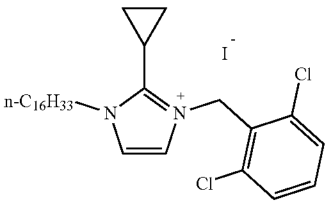 | 38.2 | 38.2 | IB-44 | 93.0 | 126.8 |

-continued

| Fluorine-free compound | | | Fluorine substituted compound | | |
|---|---|---|---|---|---|
| ID | HLM 0.5 $T_{1/2}$ (min) | DLM 0.5 $T_{1/2}$ (min) | ID | HLM 0.5 $T_{1/2}$ (min) | DLM 0.5 $T_{1/2}$ (min) |
| 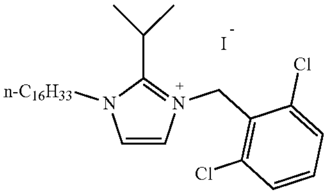 | 47.9 | 36.9 | IB-41 | 85.3 | 79.7 |
| | | | IB-4 | >145 | >145 |
| | | | IB-16 | >145 | >145 |
| | | | IB-33 | >145 | >145 |
| | | | IB-38 | >145 | >145 |
| | | | IB-50 | >145 | 122.2 |

In the above table, HLM 0.5 $T_{1/2}$ (min) refers to half life (min) of compounds in human liver microsome, DLM 0.5 $T_{1/2}$ (min) refers to half life (min) of compounds in Beagle dog liver microsome.

III. Hepatocyte Metabolism Assay

Experimental procedures: a test sample (concentration: 10 μM) or a positive control (concentration: 30 μM) was co-incubated with hepatic cells of various genera (cell density: $1.0\times10^6$ cells/mL) for 120 min under the conditions of 37° C./5% $CO_2$/saturated humidity. The sample was centrifuged after protein precipitation by using acetonitrile solution containing 0.1% formic acid according to the proportion of 1:2, the supernatant was blown dry by nitrogen, and then redissolved by using 200 μl of a 10% acetonitrile/water (containing 0.1% formic acid) solution. 15 μL of the obtained solution was introduced each time to an LC-MS instrument system for analysis.

Possible Metabolites of LXY-CI Detected in Human Hepatocytes

| Metabolite No. | $[M-Cl^-]^+$ m/z | Retention time (min) | Relative abundance (MS peak area %) | Metabolic pathway |
|---|---|---|---|---|
| M1 | 327.07 | 3.58 | 6.64 | Oxidative dealkylation ($P - C_{12}H_{26} + 2O$) |
| M2 | 341.08 | 3.85 | 0.85 | Oxidative dealkylation ($P - C_{11}H_{24} + 2O$) |
| M3 | 355.10 | 4.23 | 29.31 | Oxidative dealkylation ($P - C_{10}H_{22} + 2O$) |
| M4 | 427.16 | 4.51 | 0.13 | Oxidative dealkylation and monooxidation ($P - C_6H_{16} + 2O + O$) |
| M5 | 369.11 | 4.66 | 2.09 | Oxidative dealkylation ($P - C_9H_{20} + 2O$) |
| M7 | 383.13 | 5.13 | 19.24 | Oxidative dealkylation ($P - C_8H_{18} + 2O$) |
| M8 | 468.18 | 5.27 | 1.22 | Oxidative dealkylation and glycine binding ($P - C_6H_{14} + 20 + C_2H_3NO$) |
| M9 | 455.19 | 5.30 | 0.22 | Oxidative dealkylation and monooxidation ($P - C_4H_{10} + 2O + O$) |
| M10 | 397.14 | 5.58 | 1.18 | Oxidative dealkylation ($P - C_7H_{16} + 2O$) |
| M11 | 483.22 | 5.98 | 0.16 | Oxidative dealkylation and monooxidation ($P - C_2H_6 + 2O + O$) |
| M12 | 483.22 | 6.03 | 0.19 | Oxidative dealkylation and monooxidation ($P - C_2H_6 + 2O + O$) |
| M13 | 411.16 | 6.04 | 15.15 | Oxidative dealkylation ($P - C_6H_{14} + 2O$) |
| M14 | 483.22 | 6.13 | 0.21 | Oxidative dealkylation and monooxidation ($P - C_2H_6 + 2O + O$) |
| M15 | 481.20 | 6.21 | 0.21 | Oxidative dealkylation, monooxidation and dehydrogenation ($P - C_2H_6 + 2O + O - 2H$) |
| M16 | 481.20 | 6.28 | 0.17 | Oxidative dealkylation, monooxidation and dehydrogenation ($P - C_2H_6 + 2O + O - 2H$) |
| M17 | 425.18 | 6.50 | 0.61 | Oxidative dealkylation ($P - C_5H_{12} + 2O$) |
| M18 | 511.25 | 6.75 | 0.35 | Oxidation ($P + 2O - 2H + O$) |
| M19 | 439.19 | 6.95 | 0.71 | Oxidative dealkylation ($P - C_4H_{10} + 2O$) |
| M20 | 467.22 | 7.79 | 0.51 | Oxidative dealkylation ($P - C_2H_6 + 2O$) |
| LXY-Cl (parent drug) | 465.28 | 10.97 | 20.85 | NA |

Possible Metabolites of IB-33 Detected in Human Hepatocytes

| Metabolite No. | $[M - CL^-]^+$ m/z | Retention time (min) | Relative abundance (MS peak area %) | MS peak area | Metabolic pathway |
|---|---|---|---|---|---|
| M1 | 441.17 | 5.53 | 1.73 | 2845.8 | Oxidative dealkylation and monooxidation ($P + 3O - C_5HF_{11}$) |
| M2 | 411.16 | 5.98 | 2.71 | 4466.2 | Oxidative dealkylation ($P + 2O - C_6H_3F_{11}$) |
| M3 | 425.18 | 6.44 | 1.38 | 2281.3 | Oxidative dealkylation ($P + 2O - C_5HF_{11}$) |
| M4 | 641.15 | 10.10 | 7.80 | 12850.1 | dehydrofluorination |

-continued

| Metabolite No. | [M - CL⁻]⁺ m/z | Retention time (min) | Relative abundance (MS peak area %) | MS peak area | Metabolic pathway |
|---|---|---|---|---|---|
| | | | | | and dehydrogenation (P − HF − 2H) |
| M5 | 661.16 | 10.17 | 7.06 | 11635.1 | dehydrogenation (P − 2H) |
| IB-33 (parent drug) | 663.18 | 10.41 | 79.31 | 130654.0 | Not applicable |

The above results of liver microsome stability and hepatocyte metabolism demonstrated that the metabolic stability of the fluorine-substituted compounds was significantly improved.

IV. In Vivo Efficacy Assay of Compound IB-33

Figure 4:
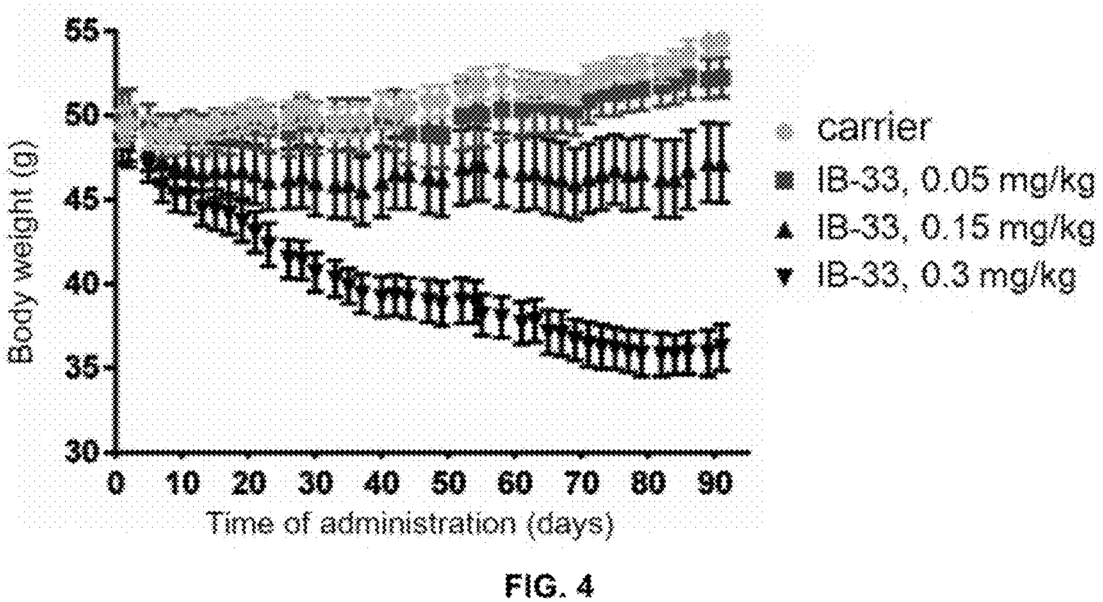
FIG. 4 shows that IB-33 is effective in reducing body weight in high-fat-fed obese mice.
Figure 5:
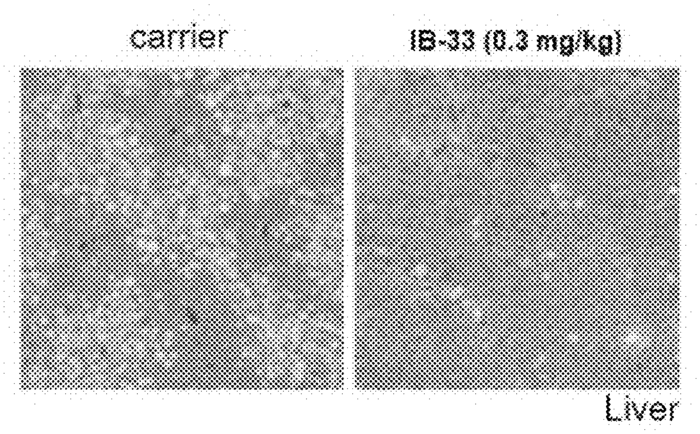
FIG. 5 shows that IB-33 is effective in reducing fat accumulation in the liver in high-fat-fed obese mice.
Figure 6:
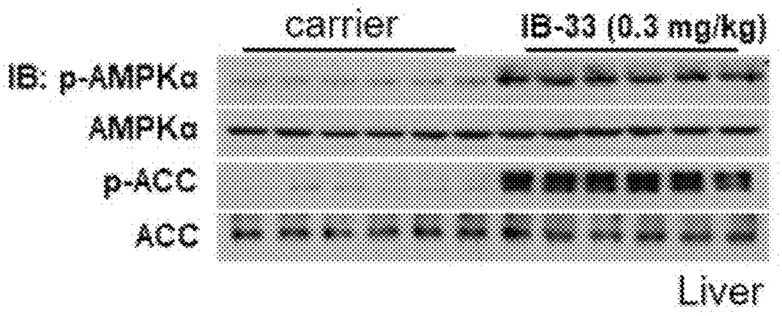
FIG. 6 shows that IB-33 is effective in lowering blood sugar in sugar tolerance test of mice.

After administration by subcutaneous injection (s.c.), the compound IB-33 could significantly reduce the body weight and improve the fat accumulation level in the liver in high-fat-fed obese mice model. The detection of the body weight of the mice after the administration (FIG. 4) and the morphology of the liver slice (FIG. 5) showed that the compound IB-33 had good effects of reducing body weight and treating fatty liver, and the detection of the phosphorylation level of threonine at the $172^{nd}$ position of AMPK and the phosphorylation level of serine at the $79^{th}$ position of the susbtrate ACC1/ACC2 of AMPK by western blot showed that the compound IB-33 could effectively activate AMPK in the mice (FIG. 6).

The specific method was as follows:

1) 6-week wild-type C57BL/6J male mice were high-fat fed with 60% fat, after 10 weeks, the body weight reached 50 g, and then, drug treatment was started, and the high-fat diet was maintained during the drug treatment.

(2) At 5 μm every day, the mice were weighed, and administered with IB-33 by subcutaneous injection (s.c.) at a concentration of 0.05, 0.15, 0.3 mg/kg once every two days, and administered with vehicle by subcutaneous injection in the same proportion.

(3) 90 days after continuous feeding, with the weight being weighed and recorded every day, some mice were euthanized on the 90th day, the livers of the mice were taken out, fixed, sliced and HE stained, and then the histological characteristics were directly observed.

(4) 90 days after administration, some mice were killed by cervical dislocation, the livers of the mice were quickly taken out, put in a 1.5 ml tube and quenched in liquid nitrogen.

(5) About 50 mg of the liver was cut, and a cell lysate (its formulation was given below) was added at a ratio of 1 mg/μL, followed by homogenization and ultrasonication, and low temperature centrifugation at 20000 g for 10 min.

(6) The supernatant and an equal volume of 2*SDS solution (its formulation was given below) were mixed, subjected to SDS-PAGE in a concentration of 8%, and then the protein was transferred to PVDF membrane; each PVDF membrane was blocked with 25 mL of skim milk for 1 h, and then rinsed with TBST buffer (its formulation was given below) 3 times for 10 min each time;

(7) AMPKα subunit primary antibody (Cell Signaling Technology, #2532), primary antibody of phosphothreonine at the $172^{nd}$ position of AMPK (Cell Signaling Technology, #2535), ACC primary antibody (Cell Signaling Technology, #3662) or primary antibody of phosphoserine at the $79^{th}$ position of ACC (Cell Signaling Technology, #3661) was diluted in a ratio of 1:1000 with a primary antibody dilution (its formulation was given below), reacted with the PVDF membrane at room temperature for 12 h, and then rinsed 3 times with TBST buffer;

(8) A 1:1000 dilution of HRP-conjugated goat anti-rabbit secondary antibody (Jackson ImmunoResearch, 111-035-003) was added, reacted at room temperature for 1 h, and then rinsed 3 times with TBST buffer;

(9) The PVDF membrane was dried, reacted in an ECL mixture (WesternBright ECL HRP substrate, Advansta) and subjected to exposure with medical X-ray, developed, finally rinsed, dried, and then scanned to obtain data related to AMPK activation.

The formulations of reagents used were:

Cell lysate: 20 mM Tris-base, pH 7.5, 150 mM NaCl, 1 mM EDTA, 1 mM EGTA, 2.5 mM Sodium pyrophosphate, 1 mM β-glycerolphosphate, 1% Triton X-100 (v/v);

2*SDS solution: 20% Glycerol (v/v), 4% SDS (m/v), 10% β-mecaptoethanol (v/v), 0.01% Bromophenol blue (m/v); TBST buffer: 4.84% Tris-base (m/v), 8% NaCl (m/v), 0.1% Tween-20 (v/v);

Primary antibody dilution: TBST buffer containing 5% BSA (v/v).

Figure 7:
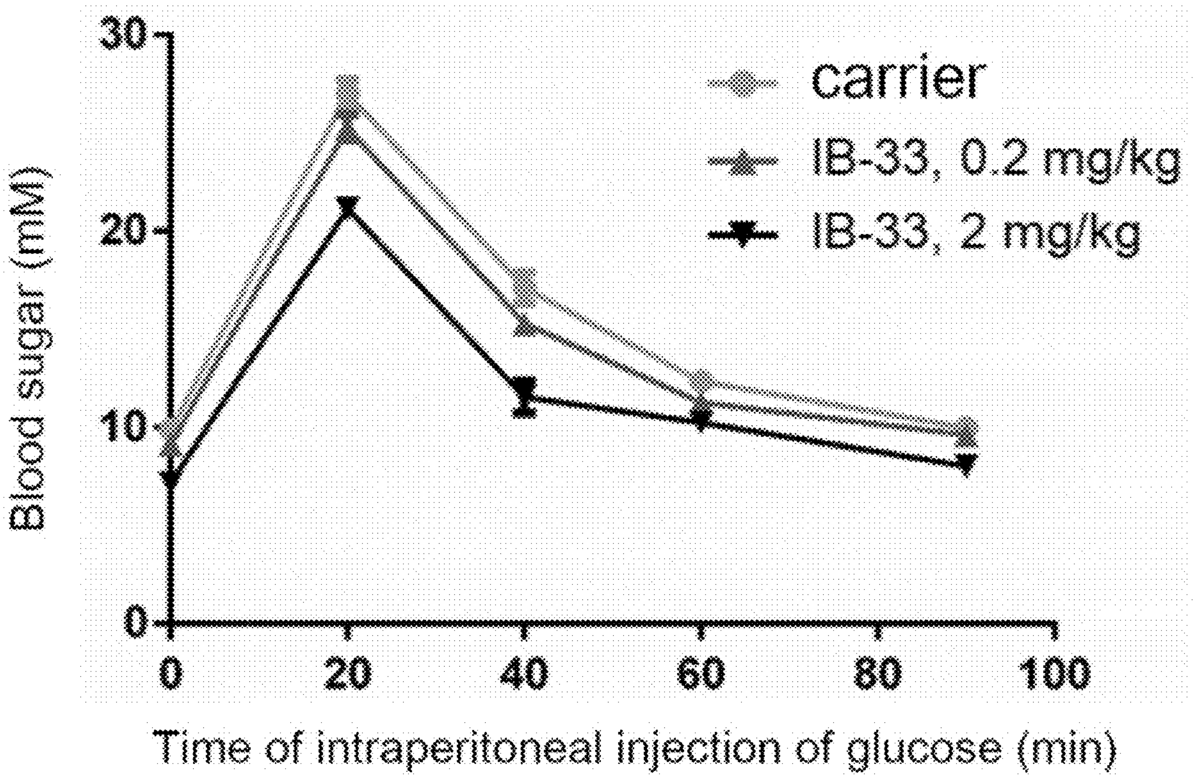
FIG. 7 shows the performance of the compound IB-33 in sugar tolerance test of mice, which is effective in lowering blood sugar.

Compound IB-33 could significantly lower blood sugar in sugar tolerance test of mice; FIG. 7 showed that the compound (IB-33) could significantly lower blood sugar in ip-GTT.

(14) 6-week wild-type C57BL/6J male mice started to fast at 6:00 am; after 4 h, the blood sugar (−120 min) and the body weight were measured, the mice were intragastrically administered with IB-33 at a dose of 0.2, 2 mg/kg, and intragastrically administered with vehicle in the same proportion.

(15) After 2 h, the blood sugar (0 min) was measured, the mice were intraperitoneally injected with 20% (v/v) glucose solution at a concentration of 1 g/kg, and then the blood sugar was measured respectively at 20, 40, 60, and 90 min after the injection.

What is claimed is:

1. A compound of a formula

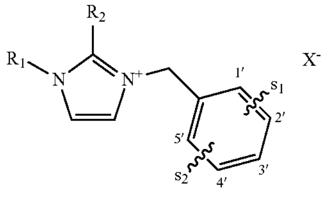

wherein, $R_1$ is a C16-C18 alkyl substituted by 11, 13 or 15 fluorine atoms;

$R_2$ is selected from H, C1-C6 alkyl, and C3-C6 cycloalkyl;

$S_1$ is selected from 1'-halogen and 1'-C1-C6 alkoxy;

$S_2$ is selected from: 4'-halogen and 5'-halogen; and $X^-$ is an anion of a pharmaceutically acceptable inorganic or organic acid salt;

or a pharmaceutically acceptable salt thereof.

2. The compound according to claim 1, which is selected from:
| No. | Structure |
| --- | --- |
| IB-30 | 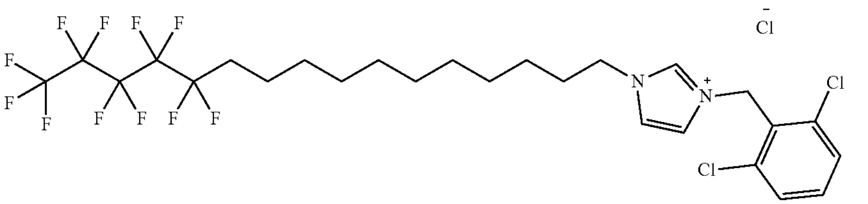 [SMILES: FC(F)(F)C(F)(F)C(F)(F)C(F)(F)C(F)(F)CCCCCCCCCCCn1cc[n+](Cc2c(Cl)cccc2Cl)c1 ; [Cl-]] |
| IB-31 | 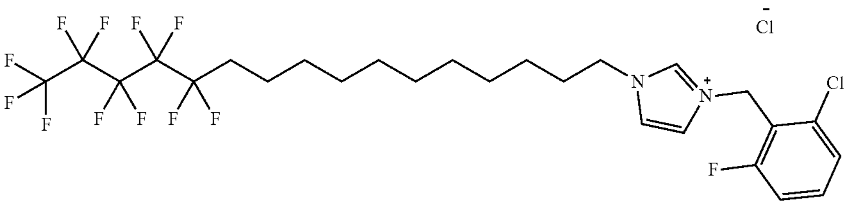 [SMILES: Fc1cccc(Cl)c1C[n+]1ccn(CCCCCCCCCCCC(F)(F)C(F)(F)C(F)(F)C(F)(F)C(F)(F)F)c1 ; [Cl-]] |
| IB-32 | 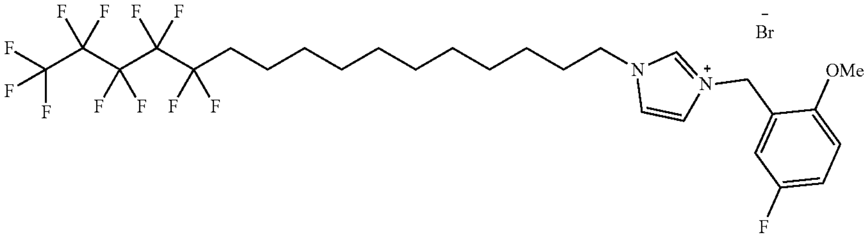 [SMILES: COc1ccc(F)cc1C[n+]1ccn(CCCCCCCCCCCC(F)(F)C(F)(F)C(F)(F)C(F)(F)C(F)(F)F)c1 ; [Br-]] |
| IB-33 | 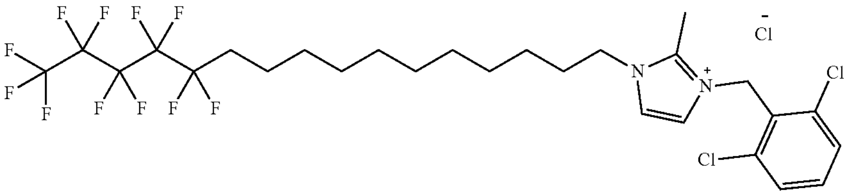 [SMILES: Cc1n(CCCCCCCCCCCC(F)(F)C(F)(F)C(F)(F)C(F)(F)C(F)(F)F)cc[n+]1Cc1c(Cl)cccc1Cl ; [Cl-]] |
| IB-34 | 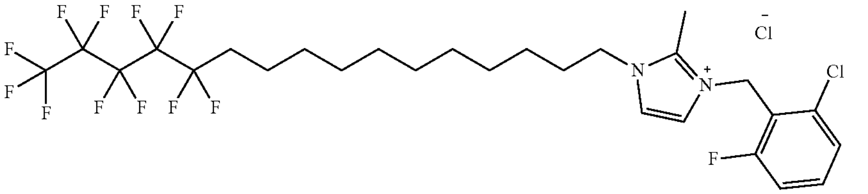 [SMILES: Cc1n(CCCCCCCCCCCC(F)(F)C(F)(F)C(F)(F)C(F)(F)C(F)(F)F)cc[n+]1Cc1c(F)cccc1Cl ; [Cl-]] |
| IB-35 | 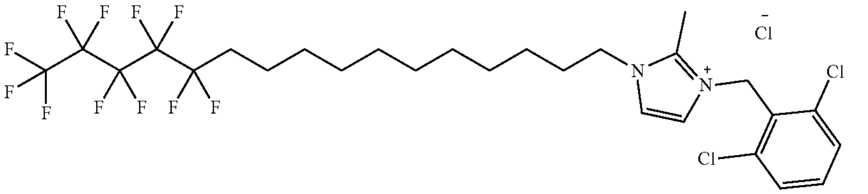 [SMILES: Cc1n(CCCCCCCCCCCC(F)(F)C(F)(F)C(F)(F)C(F)(F)C(F)(F)F)cc[n+]1Cc1c(Cl)cccc1Cl ; [Cl-]] |
| IB-36 | 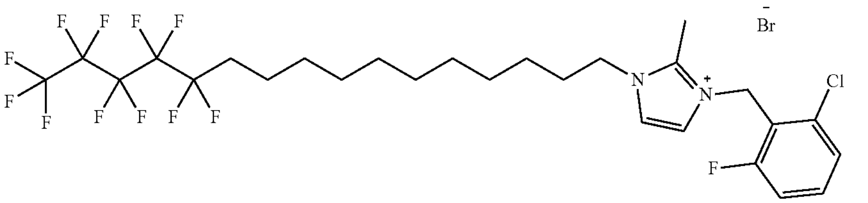 [SMILES: Cc1n(CCCCCCCCCCCC(F)(F)C(F)(F)C(F)(F)C(F)(F)C(F)(F)F)cc[n+]1Cc1c(F)cccc1Cl ; [Br-]] |

-continued
| No. | Structure |
| --- | --- |
| IB-37 | 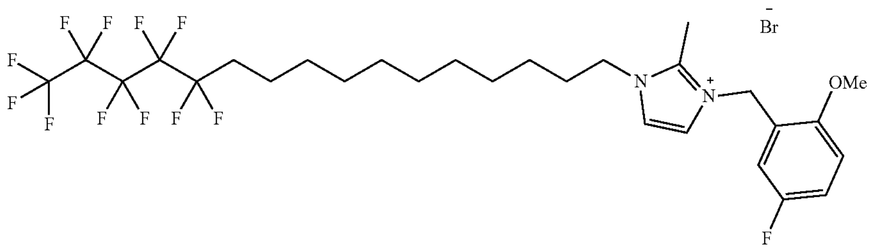 [SMILES: COc1ccc(F)cc1C[n+]1ccn(CCCCCCCCCCCC(F)(F)C(F)(F)C(F)(F)C(F)(F)C(F)(F)F)c1C ; [Br-]] |
| IB-38 | 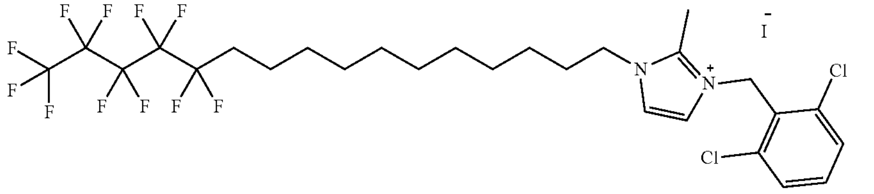 [SMILES: Cc1n(CCCCCCCCCCCC(F)(F)C(F)(F)C(F)(F)C(F)(F)C(F)(F)F)cc[n+]1Cc1c(Cl)cccc1Cl ; [I-]] |
| IB-39 | 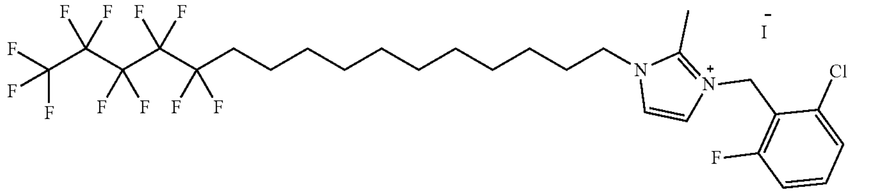 [SMILES: Cc1n(CCCCCCCCCCCC(F)(F)C(F)(F)C(F)(F)C(F)(F)C(F)(F)F)cc[n+]1Cc1c(F)cccc1Cl ; [I-]] |
| IB-40 | 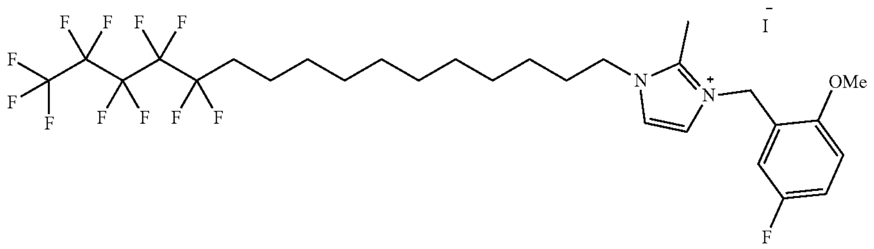 [SMILES: COc1ccc(F)cc1C[n+]1ccn(CCCCCCCCCCCC(F)(F)C(F)(F)C(F)(F)C(F)(F)C(F)(F)F)c1C ; [I-]] |
| IB-41 | 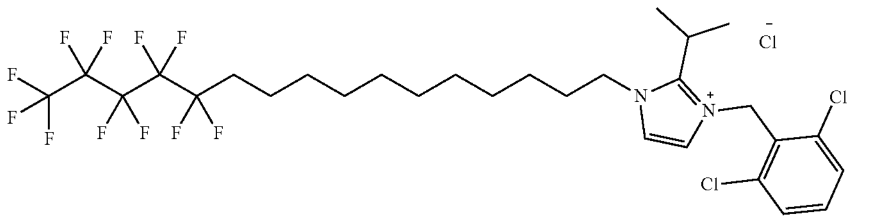 [SMILES: CC(C)c1n(CCCCCCCCCCCC(F)(F)C(F)(F)C(F)(F)C(F)(F)C(F)(F)F)cc[n+]1Cc1c(Cl)cccc1Cl ; [Cl-]] |
| IB-42 | 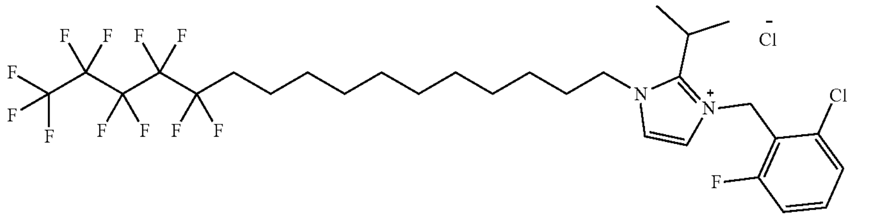 [SMILES: CC(C)c1n(CCCCCCCCCCCC(F)(F)C(F)(F)C(F)(F)C(F)(F)C(F)(F)F)cc[n+]1Cc1c(F)cccc1Cl ; [Cl-]] |

-continued
| No. | Structure |
|---|---|
| IB-43 | 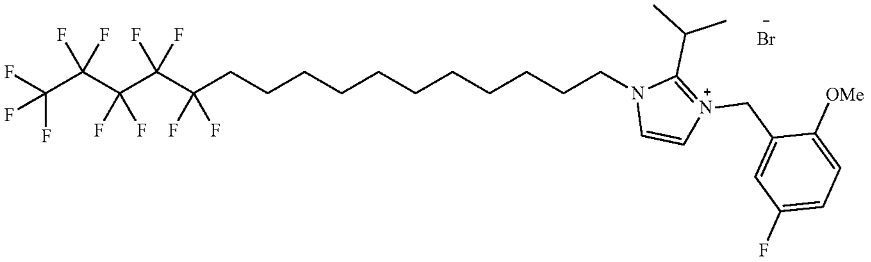 [SMILES: COc1ccc(F)cc1C[n+]1ccn(CCCCCCCCCCCC(F)(F)C(F)(F)C(F)(F)C(F)(F)C(F)(F)F)c1C(C)C ; [Br-]] |
| IB-44 | 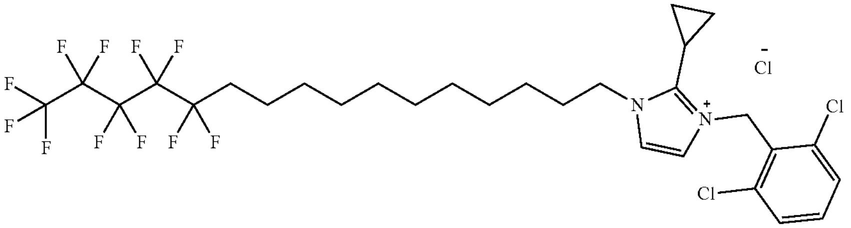 [SMILES: FC(F)(F)C(F)(F)C(F)(F)C(F)(F)C(F)(F)CCCCCCCCCCCn1cc[n+](Cc2c(Cl)cccc2Cl)c1C1CC1 ; [Cl-]] |
| IB-45 | 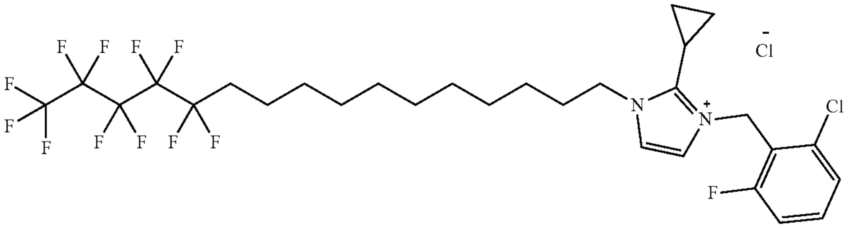 [SMILES: Fc1cccc(Cl)c1C[n+]1ccn(CCCCCCCCCCCC(F)(F)C(F)(F)C(F)(F)C(F)(F)C(F)(F)F)c1C1CC1 ; [Cl-]] |
| IB-46 | 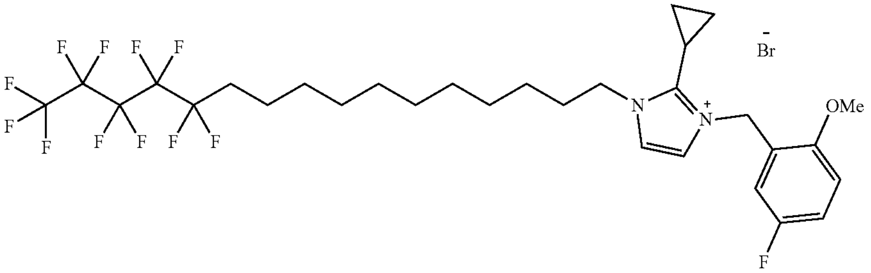 [SMILES: COc1ccc(F)cc1C[n+]1ccn(CCCCCCCCCCCC(F)(F)C(F)(F)C(F)(F)C(F)(F)C(F)(F)F)c1C1CC1 ; [Br-]] |
| IB-47 | 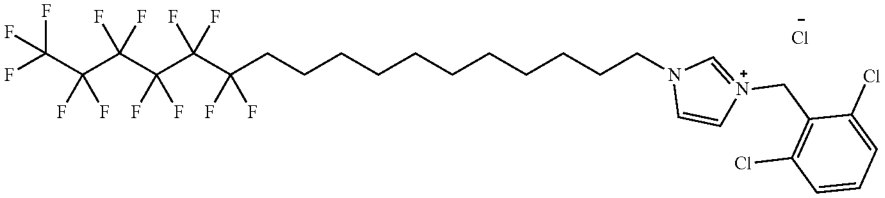 [SMILES: FC(F)(F)C(F)(F)C(F)(F)C(F)(F)C(F)(F)C(F)(F)CCCCCCCCCCCn1cc[n+](Cc2c(Cl)cccc2Cl)c1 ; [Cl-]] |
| IB-48 | 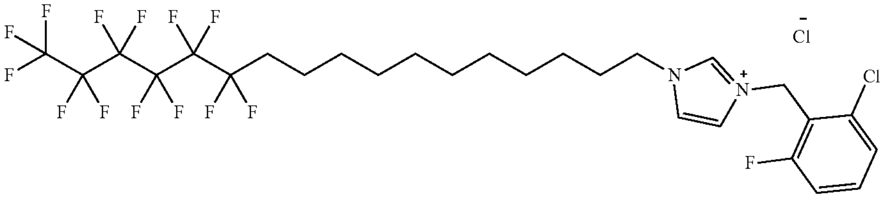 [SMILES: Fc1cccc(Cl)c1C[n+]1ccn(CCCCCCCCCCCC(F)(F)C(F)(F)C(F)(F)C(F)(F)C(F)(F)C(F)(F)F)c1 ; [Cl-]] |

-continued
| No. | Structure |
| --- | --- |
| IB-49 | 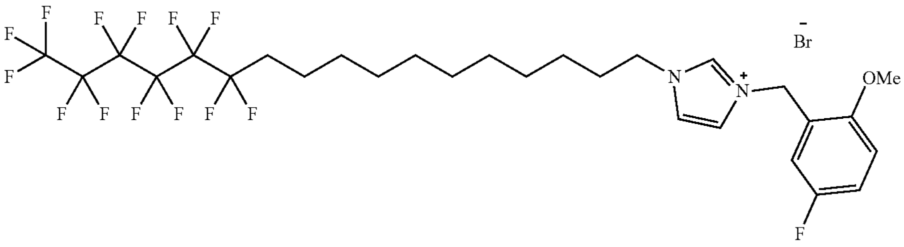 [SMILES: COc1ccc(F)cc1C[n+]1ccn(CCCCCCCCCCCC(F)(F)C(F)(F)C(F)(F)C(F)(F)C(F)(F)C(F)(F)F)c1 ; [Br-]] |
| IB-50 | 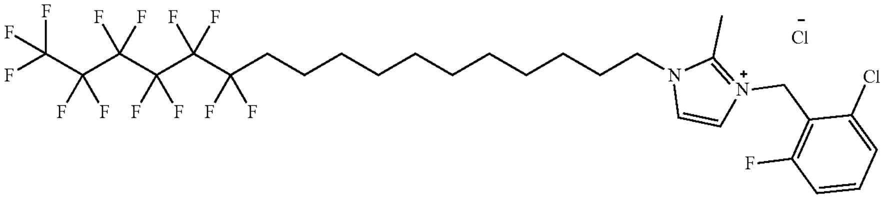 [SMILES: Cc1n(CCCCCCCCCCCC(F)(F)C(F)(F)C(F)(F)C(F)(F)C(F)(F)C(F)(F)F)cc[n+]1Cc1c(F)cccc1Cl ; [Cl-]] |
| IB-51 | 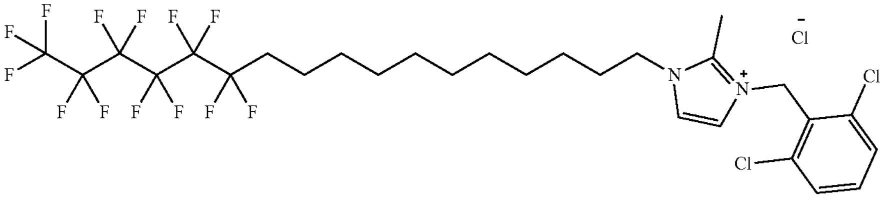 [SMILES: Cc1n(CCCCCCCCCCCC(F)(F)C(F)(F)C(F)(F)C(F)(F)C(F)(F)C(F)(F)F)cc[n+]1Cc1c(Cl)cccc1Cl ; [Cl-]] |
| IB-52 | 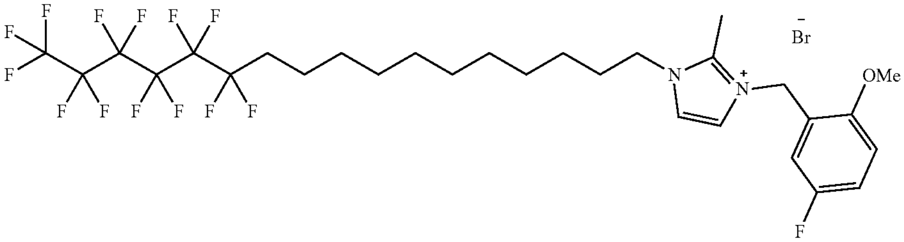 [SMILES: COc1ccc(F)cc1C[n+]1ccn(CCCCCCCCCCCC(F)(F)C(F)(F)C(F)(F)C(F)(F)C(F)(F)C(F)(F)F)c1C ; [Br-]] |
| IB-53 | 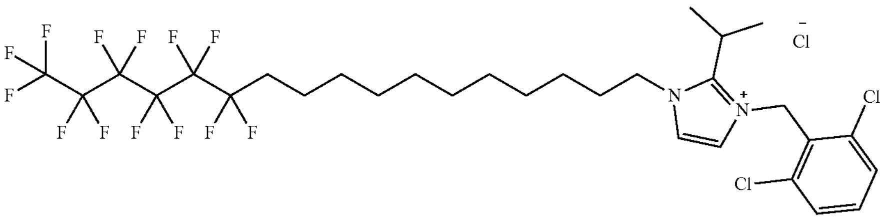 [SMILES: CC(C)c1n(CCCCCCCCCCCC(F)(F)C(F)(F)C(F)(F)C(F)(F)C(F)(F)C(F)(F)F)cc[n+]1Cc1c(Cl)cccc1Cl ; [Cl-]] |
| IB-54 | 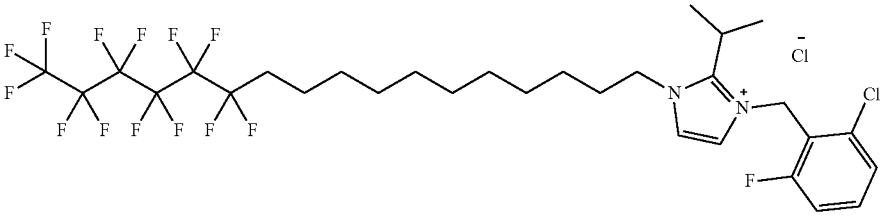 [SMILES: CC(C)c1n(CCCCCCCCCCCC(F)(F)C(F)(F)C(F)(F)C(F)(F)C(F)(F)C(F)(F)F)cc[n+]1Cc1c(F)cccc1Cl ; [Cl-]] |

-continued
| No. | Structure |
|---|---|
| IB-55 | 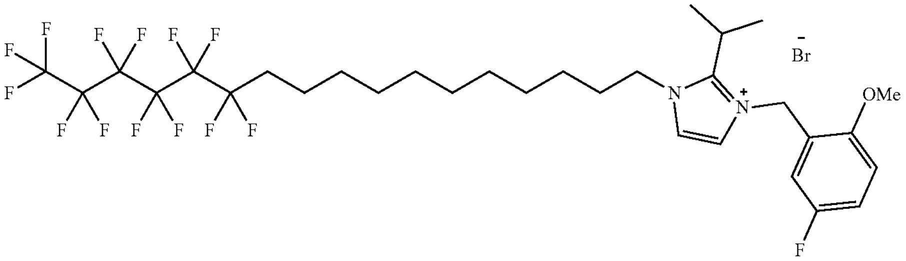 [SMILES: COc1ccc(F)cc1C[n+]1ccn(CCCCCCCCCCCC(F)(F)C(F)(F)C(F)(F)C(F)(F)C(F)(F)C(F)(F)F)c1C(C)C ; [Br-]] |
| IB-56 | 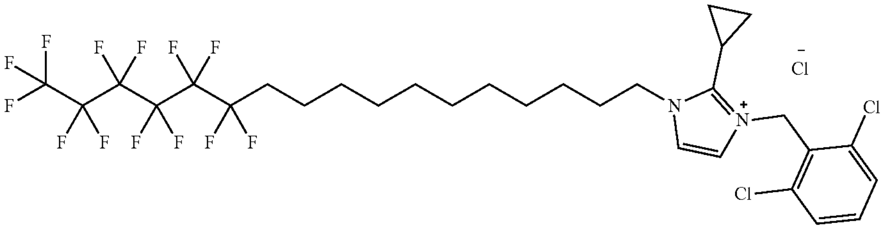 [SMILES: FC(F)(F)C(F)(F)C(F)(F)C(F)(F)C(F)(F)C(F)(F)CCCCCCCCCCCn1cc[n+](Cc2c(Cl)cccc2Cl)c1C1CC1 ; [Cl-]] |
| IB-57 | 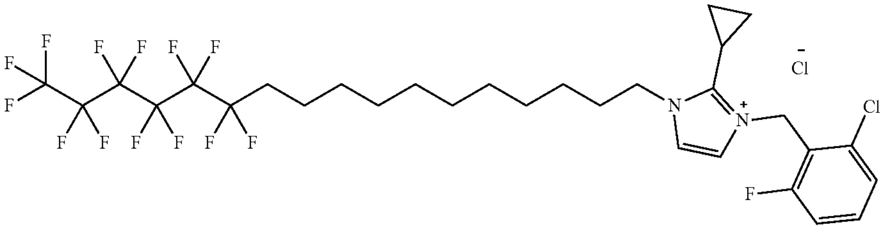 [SMILES: Fc1cccc(Cl)c1C[n+]1ccn(CCCCCCCCCCCC(F)(F)C(F)(F)C(F)(F)C(F)(F)C(F)(F)C(F)(F)F)c1C1CC1 ; [Cl-]] |
| IB-58 | 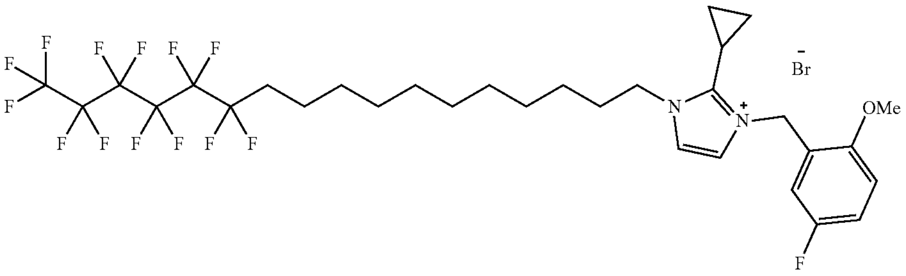 [SMILES: COc1ccc(F)cc1C[n+]1ccn(CCCCCCCCCCCC(F)(F)C(F)(F)C(F)(F)C(F)(F)C(F)(F)C(F)(F)F)c1C1CC1 ; [Br-]] |
| IB-59 | 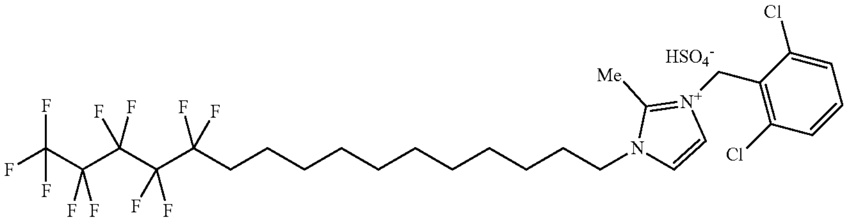 |
| and IB-60 | 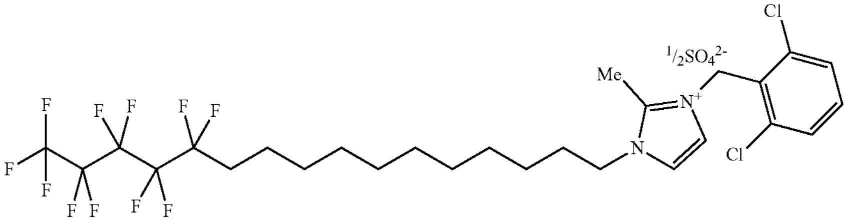 |
or a prodrug thereof, a pharmaceutically acceptable salt thereof.
3. A pharmaceutical composition comprising the compound according to claim 1, or a pharmaceutically acceptable salt thereof.

4. A pharmaceutical composition comprising the compound according to claim 2, or a pharmaceutically acceptable salt thereof and optionally a pharmaceutically acceptable excipient.

5. The compound according to claim 1, wherein $R_2$ is H, a C1-C3 alkyl, or a C3-C4 cycloalkyl; or wherein $X^-$ is selected from a group consisting of chloride ion, bromide ion, iodide ion, bisulfate ion, sulfate ion, phosphate ion, maleate ion, fumarate ion, tartrate ion, palmitate ion, oxalate ion, citrate ion, succinate ion, methanesulfonate ion, benzenesulfonate ion, and p-toluenesulfonate ion.

6. The compound according to claim 1, wherein $R_1$ is selected from the group consisting of $C_{16}F_{11}H_{22}$—, and $C_{17}F_{13}H_{22}$—; or wherein $R_2$ is selected from the group consisting of H, methyl, isopropyl, and cyclopropyl; or wherein $S_1$ is a 1'-C1-C3 alkoxy.

7. The compound according to claim 1, wherein $R_1$ is selected from the group consisting of n-$C_{16}F_{11}H_{22}$—, and n-$C_{17}F_{13}H_{22}$—.

8. The composition according to claim 3, wherein the composition further comprises a pharmaceutically acceptable excipient.

9. The composition according to claim 1, wherein $S_1$ is selected from 1'-halogen, and 1'-C1-C3 alkoxy.

* * * * *